(12) United States Patent
Clark et al.

(10) Patent No.: US 7,220,546 B2
(45) Date of Patent: May 22, 2007

(54) METHODS FOR DIAGNOSING GLAUCOMA AND DISCOVERING ANTI-GLAUCOMA DRUGS

(75) Inventors: Abbot F. Clark, Arlington, TX (US); Robert J. Wordinger, Euless, TX (US)

(73) Assignees: Alcon Manufacturing, Ltd., Fort Worth, TX (US); University of North Texas Health Science Center, Fort Worth, TX (US)

( * ) Notice: Subject to any disclaimer, the term of this patent is extended or adjusted under 35 U.S.C. 154(b) by 596 days.

(21) Appl. No.: 10/658,986

(22) Filed: Sep. 10, 2003

(65) Prior Publication Data

US 2005/0255476 A1 Nov. 17, 2005

Related U.S. Application Data

(63) Continuation-in-part of application No. 09/308,295, filed as application No. PCT/US97/21054 on Nov. 14, 1997, now abandoned.

(60) Provisional application No. 60/033,227, filed on Dec. 5, 1996.

(51) Int. Cl.
*C12Q 1/68* (2006.01)
*C07K 14/72* (2006.01)
*A61K 38/18* (2006.01)

(52) U.S. Cl. .................. 435/6; 435/69.1; 435/325; 435/320.1; 530/350

(58) Field of Classification Search .................. None
See application file for complete search history.

(56) References Cited

FOREIGN PATENT DOCUMENTS

| | | |
|---|---|---|
| AU | 728438 | 4/2001 |
| WO | WO 96/14411 A1 | 5/1996 |
| WO | WO 96/33287 A1 | 10/1996 |
| WO | WO 98/24932 A1 | 6/1998 |

OTHER PUBLICATIONS

Bamberger, et al., The Journal of Clinical Investigation, "Glucocorticoid Receptor β, a Potential endogenous Inhibitor of Glucocorticoid Action in Humans," 95:2435-2441, 1995.
Caskey, C.T., J.A.M.A., "Molecular Medicine. A Spin-off From the Helix," 269:15, 1986-1992, 1993.
Clark, A.F. Journal of Glaucoma, "Steroids, Ocular Hypertension, and Glaucoma", 4:354-369, 1995.
Encio, et al., Journal of Biological Chemistry, "The Genomic Structure of the Human Glucocorticoid Receptor," 266(11):7182-7188, 1991.
Giguère et al., "Functional Domains of the Human Glucocorticoid Receptor," Cell, 46:645-652, 1986.
Hernandez, et al., Invest. Ophthalmol. Vis. Sci., "Glucocorticoid Target Cells in Human Outflow Pathway: Autopsy and Surgical Specimens," 24:1612-1616, 1983.
Hollenberg et al., "Primary structure and expression of a functional human glucocorticoid receptor cDNA," Nature, 318:635-641, 1985.
Leung, et al., "Association of Glucocorticoid Insensitivity with Increased Expression of Glucocorticoid Receptor β," Journal of Experimental Medicine, 186(9):1567-1574, 1997.
Myers, R.M., et al., "Detection of DNA Variation", Genome Analysis, Birren (eds) 2:287-384, 1998.
Oakley et al., "Expression and Subcellular Distribution of the β-Isoform of the Human Glucocorticoid Receptor," Endocrinology, 138(11):5028-5038, 1997.
Oakley, et al., The Journal of Biological Chemistry, "The Human Glucocorticoid Receptor β Isoform," 271:16, 9550-9559, 1996.
Weinreb, et al., Invest. Ophthalmol. Vis. Sci., "Detection of Glucocorticoid Receptors in Cultured Human Trabecular Cells," 21:3, 403-407, 1981.
Wordinger, et al., "Effects of Glucocorticoids on the Trabecular Meshwork: Towards a Better Understanding of Glaucoma," Progress in Retinal and Eye Research, 18(5):629-667, 1999.

*Primary Examiner*—Gary B. Nickol
*Assistant Examiner*—Nirmal S. Basi
(74) *Attorney, Agent, or Firm*—Teresa J. Schultz

(57) ABSTRACT

Methods for diagnosing glaucoma and for screening therapeutic agents for their usefulness in treating glaucoma are disclosed.

1 Claim, 2 Drawing Sheets

SEQUENCE LISTING

<160> NUMBER OF SEQ ID NOS: 5

<210> SEQ ID NO 1
<211> LENGTH: 3791
<212> TYPE: RNA
<213> ORGANISM: homo sapiens

<400> SEQUENCE: 1

```
uuuuuagaaa aaaaaaauau auuucccucc ugcuccuucu gcguucacaa gcuaaguugu      60
uuaucucggc ugcggcggga acugcggacg guggcgggcg agcggcuccu cugccagagu     120
ugauauucac ugauggacuc caaagaauca uuaacuccug guagagaaga aaccccagc     180 agugugcuug cucaggagag gggagaugug auggacuucu auaaaacccu aagaggagga     240
gcuacuguga agguuucugc gucuucaccc ucacuggcug ucgcuucuca aucagacucc     300
aagcagcgaa gacuuuuggu ugauuuucca aaaggcucag uaagcaaugc gcagcagcca     360
gaucugucca aagcaguuuc acucucaaug ggacuguaua ugggagagac agaaacaaaa     420
gugaugggaa augaccuggg auucccacag cagggccaaa ucagccuuuc cucggggaa      480 acagacuuaa agcuuuugga agaaagcauu gcaaaccuca auaggucgac caguguucca     540 gagaaccccca agaguucagc auccacugcu gugucugcug cccccacaga gaaggaguuu     600
ccaaaaacuc acucugaugu aucuucagaa cagcaacauu ugaagggcca gacuggcacc     660
aacgguggca augugaaauu guauaccaca gaccaaagca ccuuugacau uuugcaggau     720
uuggaguuuu cuucgggguc cccagguaaa gagacgaaug agaguccuug gagaucagac     780
```

```
cguugauag augaaaacug uuugcuuucu ccucuggcgg gagaagacga uucauuccuu     840
uuggaaggaa acucgaauga ggacugcaag ccucucauuu uaccggacac uaaacccaaa     900
auuaaggaua auggagaucu gguuuuguca agccccagua auguaacacu gccccaagug     960
aaaacagaaa aagaagauuu caucgaacuc ugcaccccug gguaauuaa gcaagagaaa    1020 cugggcacag uuuacuguca ggcaagcuuu ccuggagcaa auauaauugg uaauaaaaug    1080
ucugccauuu cuguucaugg ugugaguacc ucggaggac agauguacca cuaugacaug     1140
aauacagcau cccuuucuca acagcaggau cagaagccua uuuuaaugu cauuccacca    1200 auucccguug guuccgaaaa uuggaauagg ugccaaggau cuggagauga caacuugacu    1260
ucucugggga cucugaacuu cccuggucga acaguuuuuu cuaauggcua uucaagcccc    1320
agcaugagac cagauguaag cucuccucca uccagcuccu caacagcaac aacaggacca    1380
ccucccaaac ucugccuggu gugcucugau gaagcuucag gaugucauua uggagcuua    1440 acuugugga gcuguaaagu uuucuucaaa agagcagugg aaggacagca caauuaccua    1500
ugugcuggaa ggaaugauug caucaucgau aaaauucgaa gaaaaaacug cccagcaugc    1560
cgcuaucgaa aaugucuuca ggcuggaaug aaccuggaag cucgaaaaac aaagaaaaaa    1620
auaaaaggaa uucagcaggc cacuacagga gucucacaag aaaccucuga aauccuggu     1680 aacaaaacaa uaguuccugc aacguuacca caacucaccc cuacccuggu gucacuguug    1740
gagguuauug aaccugaagu guuauaugca ggauaugaua gcucuguucc agacucaacu    1800
uggaggauca ugacuacgcu caacauguua ggagggcggc aagugauugc agcagugaaa    1860
ugggcaaagg caauaccagg uuucaggaac uuacaccugg augaccaaau gacccuacug    1920
caguacuccu ggaguguucu uauggcauuu gcucuggggu ggagaucaua uagcaauca    1980 agugcaaacc ugcuguguuu ugcuccugau cugauuauua augagcagag aaugacucua    2040
cccugcaugu acgaccaaug uaaacacaug cuguauguuu ccucgaguu acacaggcuu    2100 cagguaucuu augaagagua ucucuguaug aaaaccuuac ugcuucucuc uucaguuccu    2160
aaggacgguc ugaagagcca agagcuauuu gaugaaauua gaaugaccua caucaaagag    2220
cuaggaaaag ccauugucaa gagggaagga acuccagcc agaacuggca gcgguuuuau    2280
caacugacaa aacucuugga uucuaugcau gaaaauguua ugugguuaaa accagaaagc    2340
acaucucaca cauuaaucug auuuucaucc caacaaucuu ggcgcucaaa aauagaacu    2400 caaugagaaa aagaagauua ugugcacuuc guugucaaua auaagucaac ugaugcucau    2460
cgacaacuau aggaggcuuu ucauuaaaug ggaaagaag cugugcccuu uuaggauacg    2520 uggggaaaa gaaagucauc uuaauuaugu uaauugugg auuuaagugc uauauggugg    2580
ugcuguuuga aagcagauuu auuuccuaug uauguuuaa cuggccaucc caacccaaac    2640
uguugaaguu uguaguaacu ucagugagag uugguuacuc acaacaaauc ugaaaaugua    2700 uuuuagugu uuguaggau ucugugggau acuauacaag cagaacugag gcacuuagga    2760
cauaacacuu uggggauaua uauccaaa ugccaaaac uaugggagga accuuggcc     2820 accccaaaag gaaacuaac augauuugu ucuaugaagu gcggauaau uagcauggga    2880 ugagcucugg gcaugccaug aaggaaagcc acgcucccuu cagaauucag aggcagggag    2940 caauccagu uucaccuaag ucucauaauu uuaguuccu uuuaaaacc cugaaaacua    3000 caucaccaug gaaugaaaaa uauuguuaua caauacauug aucugucaaa cuuccagaac    3060
caugguagcc uucagugaga uuccaucuu ggcuggucac ucccgacug uagcuguagg    3120 ugaauguguu uuugugugug uguucuggu uuuaguguca gaaggggaaau aaaaguguaa    3180
```

-continued

```
ggaggacacu uuaaacccuu uggguggagu uucguaauuu cccagacuau uuucaagcaa      3240
ccugguccac ccaggauuag ugaccagguu ucaggaaag gauuugcuuc ucucuagaaa       3300
augucugaaa ggauuuuauu uucugaugaa aggcuguaug aaaauacccu ccucaaauaa      3360
cuugcuuaac uacauauaga uucaagugug ucaauauucu auuuguaua uuaaaugcua       3420 uauaauggg acaaaucuau auuauacugu guauggcauu auuaagaagc uuuucauua        3480 uuuuuauca caguaauuuu aaaaugugua aaaauuaaaa ccagugacuc cuguuuaaaa       3540
auaaaaguug uaguuuuuua uucaugcuga auaauaaucu guaguuaaaa aaaaaguguc      3600
uuuuuaccua cgcagugaaa ugucagacug uaaaaccuug uuggaaaug uuuaacuuuu       3660 auuuuucau uuaaauuugc uguucuggua uuaccaaacc acacauuugu accgaauugg       3720
caguaaaugu uagccauuua cagcaaugcc aaauauggag aaacaucaua auaaaaaaau      3780
cugcuuuuuu c                                                           3791
```

<210> SEQ ID NO 2
<211> LENGTH: 742
<212> TYPE: PRT
<213> ORGANISM: homo sapiens

<400> SEQUENCE: 2

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Ser Ile Ala Asn
            115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255
```

```
Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
            275                 280                 285

Pro Gly Val Ile Lys Gln Glu Lys Leu Gly Thr Val Tyr Cys Gln Ala
            290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
        370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
                435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
            515                 520                 525

Thr Pro Thr Leu Val Ser Leu Leu Glu Val Ile Glu Pro Glu Val Leu
        530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
            595                 600                 605

Gly Trp Arg Ser Tyr Arg Gln Ser Ser Ala Asn Leu Leu Cys Phe Ala
        610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

Ser Ser Val Pro Lys Asp Gly Leu Lys Ser Gln Glu Leu Phe Asp Glu
```

-continued

```
                    675                 680                 685
Ile Arg Met Thr Tyr Ile Lys Glu Leu Gly Lys Ala Ile Val Lys Arg
        690                 695                 700

Glu Gly Asn Ser Ser Gln Asn Trp Gln Arg Phe Tyr Gln Leu Thr Lys
705                 710                 715                 720

Leu Leu Asp Ser Met His Glu Asn Val Met Trp Leu Lys Pro Glu Ser
                725                 730                 735

Thr Ser His Thr Leu Ile
            740

<210> SEQ ID NO 3
<211> LENGTH: 4788
<212> TYPE: RNA
<213> ORGANISM: homo sapiens

<400> SEQUENCE: 3
uuuuuagaaa aaaaaaauau auuucccucc ugcuccuucu gcguucacaa gcuaaguugu      60
uuaucucggc ugcggcggga acugcggacg guggcgggcg agcggcuccu cugccagagu     120
ugauauucac ugauggacuc caaagaauca uuaacuccug guagagaaga aaaccccagc     180
agugugcuug cucaggagag gggagauguc auggacuucu auaaacccu aagaggagga      240 gcuacuguga agguuucugc gcuucaccc ucacuggcu ucgcuucuca aucagacucc       300
aagcagcgaa gacuuuuggu ugauuuucca aaaggcucag uaagcaaugc gcagcagcca    360
gaucugucca aagcaguuuc acucucaaug ggacuguaua uggagagac agaaacaaaa     420 gugaugggaa augaccuggg auucccacag cagggccaaa ucagccuuuc cucggggaa     480 acagacuuaa agcuuuugga agaaagcauu gcaaaccuca auaggucgac caguguucca    540 gagaaccca agaguucagc auccacugcu ugucugcug cccccacaga aaggaguuu       600 ccaaaaacuc acucugaugu aucuucagaa cagcaacauu ugaagggcca gacuggcacc    660
aacgguggca augugaaauu guauaccaca gaccaaagca ccuuugacau uugcaggau     720 uuggaguuuu cuucgggu cccagguaaa gagacgaaug agaguccuug gagaucagac      780
cuguugauag augaaaacug uuugcuucu ccucggcgg gagaagacga uucauuccuu      840
uuggaaggaa acucgaauga ggacugcaag ccucucauuu uaccggacac uaaacccaaa    900
auuaaggaua auggagaucu gguuuuguca agccccagua auguaacacu gccccaagug    960
aaaacagaaa aagaagauuu caucgaacuc ugcaccccug gguaauuaa gcaagagaaa    1020 cugggcacag uuuacuguca ggcaagcuuu ccuggagcaa auauaauugg uaauaaaaug   1080
ucugccauuu cuguucaugg ugugaguacc ucuggaggac agaugua cuauaugcaug     1140 aauacagcau cccuuucuca acagcaggau cagaagccua uuuuaaugu cauuccacca    1200 auucccguug guccgaaaaa uuggaauagg ugccaaggau cuggagauga caacuugacu   1260
ucucugggga cucugaacuu cccggucga acaguuuuuu cuaauggcua uucaagccc     1320 agcaugagac cagauguaag cucuccucca uccagcuccu caacagcaac aacaggacca  1380
ccucccaaac ucugccuggu gugcucugau gaagcuucag gaugucauua uggagucuua  1440
acuuguggaa gcuguaaagu uuucuucaaa agagcagugg aaggacagca caauuaccua  1500
ugugcuggaa ggaaugauug caucaucgau aaaauucgaa gaaaaacug cccagcaugc   1560 cgcuaucgaa aaugucuuca ggcuggaaug aaccggaag cucgaaaaac aaagaaaaaa   1620 auaaaggaa uucagcaggc cacuacagga gucucacaag aaaccucuga aaauccuggu   1680
aacaaaacaa uaguuccugc aacguuacca caacucaccc cuacccuggu gucacuguug   1740
```

-continued

```
gagguuauug aaccugaagu guuauaugca ggauaugaua gcucuguucc agacucaacu    1800
uggaggauca ugacuacgcu caacauguua ggagggcggc aagugauugc agcagugaaa    1860
ugggcaaagg caauaccagg uuucaggaac uuacaccugg augaccaaau gacccuacug    1920
caguacuccu ggauguuucu uauggcauuu gcucggggu ggagaucaua uagacaauca     1980
agugcaaacc ugcuguguuu ugcuccugau cugauuauua augagcagag aaugacucua    2040
cccugcaugu acgaccaaug uaaacacaug cuguauguuu ccucgaguu acacaggcuu     2100 cagguaucuu augaagagua ucucuguaug aaaaccuuac ugcuucucuc uucaguuccu    2160
aaggacgguc ugaagagcca agagcuauuu gaugaaauua gaaugaccua caucaaagag    2220
cuaggaaaag ccauugucaa gagggaagga aacuccagcc agaacuggca gcgguuuuau    2280
caacugacaa aacucuugga uucuaugcau gaagugguug aaaaucuccu uaacuauugc    2340
uuccaaacau uuuuggauaa gaccaugagu auugaauucc ccgagauguu agcugaaauc    2400
aucaccaauc agauaccaaa auauucaaau ggaaauauca aaaaacuucu guuucaucaa    2460
aagugacugc cuuaauaaga augguugccu uaaagaaagu cgaauuaaua gcuuuuauug    2520
uauaaacuau caguuugucc uguagagguu uguuguuuu auuuuuauu guuuucaucu     2580 guuguuuugu uuuaaauacg cacuacaugu gguuuauaga gggccaagac uuggcaacag    2640
aagcaguuga gucgucauca cuuucagug auggagagu agauggugaa auuuauuagu     2700
uaauauaucc cagaaauuag aaaccuuaau auguggacgu aaucuccaca gucaaagaag    2760
gauggcaccu aaaccaccag ugcccaaagu cuguguaugau aacuuucucu ucauacuuuu    2820
uuucacaguu ggcuggauga aauuuucuag acuuucuguu gguguauccc cccccuguau    2880
aguuaggaua gcauuuuuga uuuaugcaug gaaaccugaa aaaaaguuua caagaguaua    2940
ucagaaaagg gaaguugugc cuuuuauagc uauuacuguc ugguuuuaac aauuuccuuu    3000 auauuuuagug aacuacgcuu gcucauuuuu ucuuacauaa uuuuuuauuc aaguauaugu    3060
acagcuguuu aagaugggca gcuaguucgu agcuuuccca aauaaacucu aaacauuaau    3120
caaucaucug ugugaaaaug gguuggugcu ucuaaccuga uggcacuuag cuaucagaag    3180
accacaaaaa uugacucaaa ucccaguau ucugucaaa aaaaaaaaaa aaaaagcuca     3240
uauuuuguau auaucugcuu cagugaggaa uuauauaggu ugugcaaauu aacaguccua    3300
acugguauag agcaccuagu ccagugaccu gcugguaaaa cuguggauga ugguugcaaa    3360
agacuaauuu aaaaaauaac uaccaagagg cccugucugu accaacgcc cuauuuuugc     3420 aauggcuaua uggcaagaaa gcugguaaac uauuugucuu ucaggaccuu uugaaguagu    3480
uuguauaacu ucuuaaaagu ugugauucca gauaaccagc uguaacacag cugagagacu    3540
uuuaaucaga caaaguaauu ccucucacua aacuuuaccc aaaaacuaaa ucucuaauau    3600
ggcaaaaaug gcuagacacc cauuuucaca uucccaucug ucaccaauug guuaaucuuu    3660
ccugauggua caggaaagcu cagcuacuga uuuuugugau uuagaacugu augucagaca    3720
uccauguuuu uaaacuaca caucccuaau guguccaua gauuuaaca caagccugu        3780 gaauuucuuc acuguugaaa auuauuuuaa acaaaauaga agcuguagua gcccuuucug    3840
ugugcaccuu accaacuuuc uguaaacuca aacuuuaaca uauuuacuaa gccacaagaa    3900
auuugauuuc uauucaaggu ggccaaauua uuuguguaau agaaaacuga aaaucuaaua    3960
uuaaaaauau ggaacuucua auauauuuuu auauuuaguu auaguuucag auauauauca    4020
uauugguauu cacuaaucug ggaagggaag ggcuacugca gcuuuacaug caauuuauua    4080
```

-continued

```
aaaugauugu aaaauagcuu guauagugua aaauaagaau gauuuuaga ugagauuguu    4140 uuaucaugac auguuauaua uuuuuuguag gggucaaaga aaugcugaug gauaaccuau    4200
augauuuaua guuuguacau gcauucauac aggcagcgau ggucucagaa accaaacagu    4260
uugcucuagg ggaagaggga gauggagacu gguccugugu gcagugaagg uugcugaggc    4320
ucugacccag ugagauuaca gaggaaguua uccucugccu cccauucuga ccacccuucu    4380
cauuccaaca gugagucugu cagcgcaggu uuaguuuacu caaucuccccc uugcacuaaa    4440 guauguaaag uauguaaaca ggagacagga aggugugcu uacauccuua aaggcaccau     4500
cuaauagcgg guuacuuuca cauacagccc ucccccagca guugaaugac aacagaagcu    4560
ucagaaguuu ggcaauaguu ugcauagagg uaccagcaau auguaaauag ugcagaaucu    4620
cauagguugc caauaauaca cuaauuccuu ucuauccuac aacaagaguu uauuccaaa    4680 uaaaaugagg acauguuuuu guuucuuug aaugcuuuuu gaauguuauu uguuauuuuc    4740
aguauuuugg agaaauuauu uaauaaaaaa acaaucauuu gcuuuuug              4788
```

<210> SEQ ID NO 4
<211> LENGTH: 777
<212> TYPE: PRT
<213> ORGANISM: homo sapiens

<400> SEQUENCE: 4

```
Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
            20                  25                  30

Leu Arg Gly Gly Ala Thr Val Lys Val Ser Ala Ser Ser Pro Ser Leu
        35                  40                  45

Ala Val Ala Ser Gln Ser Asp Ser Lys Gln Arg Arg Leu Leu Val Asp
    50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
            100                 105                 110

Ser Ser Gly Glu Thr Asp Leu Lys Leu Leu Glu Glu Ser Ile Ala Asn
        115                 120                 125

Leu Asn Arg Ser Thr Ser Val Pro Glu Asn Pro Lys Ser Ser Ala Ser
    130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
            180                 185                 190

Ile Leu Gln Asp Leu Glu Phe Ser Ser Gly Ser Pro Gly Lys Glu Thr
        195                 200                 205

Asn Glu Ser Pro Trp Arg Ser Asp Leu Leu Ile Asp Glu Asn Cys Leu
    210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255
```

-continued

Ile Lys Asp Asn Gly Asp Leu Val Leu Ser Ser Pro Ser Asn Val Thr
            260                 265                 270

Leu Pro Gln Val Lys Thr Glu Lys Glu Asp Phe Ile Glu Leu Cys Thr
        275                 280                 285

Pro Gly Val Ile Lys Gln Glu Lys Leu Gly Thr Val Tyr Cys Gln Ala
        290                 295                 300

Ser Phe Pro Gly Ala Asn Ile Ile Gly Asn Lys Met Ser Ala Ile Ser
305                 310                 315                 320

Val His Gly Val Ser Thr Ser Gly Gly Gln Met Tyr His Tyr Asp Met
                325                 330                 335

Asn Thr Ala Ser Leu Ser Gln Gln Asp Gln Lys Pro Ile Phe Asn
            340                 345                 350

Val Ile Pro Pro Ile Pro Val Gly Ser Glu Asn Trp Asn Arg Cys Gln
            355                 360                 365

Gly Ser Gly Asp Asp Asn Leu Thr Ser Leu Gly Thr Leu Asn Phe Pro
        370                 375                 380

Gly Arg Thr Val Phe Ser Asn Gly Tyr Ser Ser Pro Ser Met Arg Pro
385                 390                 395                 400

Asp Val Ser Ser Pro Pro Ser Ser Ser Thr Ala Thr Gly Pro
                405                 410                 415

Pro Pro Lys Leu Cys Leu Val Cys Ser Asp Glu Ala Ser Gly Cys His
            420                 425                 430

Tyr Gly Val Leu Thr Cys Gly Ser Cys Lys Val Phe Phe Lys Arg Ala
        435                 440                 445

Val Glu Gly Gln His Asn Tyr Leu Cys Ala Gly Arg Asn Asp Cys Ile
    450                 455                 460

Ile Asp Lys Ile Arg Arg Lys Asn Cys Pro Ala Cys Arg Tyr Arg Lys
465                 470                 475                 480

Cys Leu Gln Ala Gly Met Asn Leu Glu Ala Arg Lys Thr Lys Lys Lys
                485                 490                 495

Ile Lys Gly Ile Gln Gln Ala Thr Thr Gly Val Ser Gln Glu Thr Ser
            500                 505                 510

Glu Asn Pro Gly Asn Lys Thr Ile Val Pro Ala Thr Leu Pro Gln Leu
        515                 520                 525

Thr Pro Thr Leu Val Ser Leu Leu Glu Val Ile Glu Pro Glu Val Leu
        530                 535                 540

Tyr Ala Gly Tyr Asp Ser Ser Val Pro Asp Ser Thr Trp Arg Ile Met
545                 550                 555                 560

Thr Thr Leu Asn Met Leu Gly Gly Arg Gln Val Ile Ala Ala Val Lys
                565                 570                 575

Trp Ala Lys Ala Ile Pro Gly Phe Arg Asn Leu His Leu Asp Asp Gln
            580                 585                 590

Met Thr Leu Leu Gln Tyr Ser Trp Met Phe Leu Met Ala Phe Ala Leu
        595                 600                 605

Gly Trp Arg Ser Tyr Arg Gln Ser Ser Ala Asn Leu Leu Cys Phe Ala
        610                 615                 620

Pro Asp Leu Ile Ile Asn Glu Gln Arg Met Thr Leu Pro Cys Met Tyr
625                 630                 635                 640

Asp Gln Cys Lys His Met Leu Tyr Val Ser Ser Glu Leu His Arg Leu
                645                 650                 655

Gln Val Ser Tyr Glu Glu Tyr Leu Cys Met Lys Thr Leu Leu Leu Leu
            660                 665                 670

```
Ser Ser Val Pro Lys Asp Gly Leu Lys Ser Gln Glu Leu Phe Asp Glu
        675                 680                 685

Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
    770                 775

<210> SEQ ID NO 5
<211> LENGTH: 125594
<212> TYPE: DNA
<213> ORGANISM: homo sapiens

<400> SEQUENCE: 5
```

| | | | | | |
|---|---|---|---|---|---|
| gcggggcgga | gggctggctt | gtcagctggg | caatgggaga | ctttcttaaa | tagggctct | 60 |
| cccccacccc | atggagaaag | gggcggctgt | ttacttcctt | tttttagaaa | aaaaaaatat | 120 |
| atttccctcc | tgctccttct | gcgttcacaa | gctaagttgt | ttatctcggc | tgcggcggga | 180 |
| actgcggacg | gtggcgggcg | agcggctcct | ctgccagaga | taagaagcga | ggcgggaggg | 240 |
| ggccggggcg | cgctcgctcc | cccgaggtgc | cgctgggacc | ggagacaact | cggggccgc | 300 |
| cgcgggagcc | tacaaacttt | tattagcctc | ggggagtggg | ggtgggggc | tggcaagggc | 360 |
| cgggcgacgg | tgacgaaagg | gcagcgcgcg | ggtgacagcg | ctggcctctt | cctctccctc | 420 |
| cgcaggcgtc | ccctggccgg | gccgaggggg | aggaacctga | cctcggacgg | cgagcggagc | 480 |
| cctgtcgaac | tgccgggggc | ttcgagcctc | tcattcctcg | cgggaatcct | ggcctctttt | 540 |
| ctcccctag | tgtccccttt | ccctccaagg | ggtcgcccg | acaccgtt | tcgtggtgaa | 600 |
| cgctaagccg | cgtctgaatt | ttactcgccc | gaatatttgc | acgccacccc | ggcgcgcccg | 660 |
| agcgcgagcc | cggctccgg | ggaggccccg | gcggcgcctg | gcttgaggag | ggcgtgcggg | 720 |
| gcgcgtgagg | gtgcacacgc | gggggctga | cagcccgcaa | cttggagact | gcggccgggg | 780 |
| ccggcgttat | ctgttagaag | tgggcgtgtc | ggagagagaa | ctcaacaggt | ctggacgtac | 840 |
| ttctctttta | acctcgcact | ttttctctt | ctccaccccc | gccccgcaag | ggcttgctct | 900 |
| ttagcgtttg | ttgttaattc | gcgcctgagg | tttctaagtg | gcccctttta | gaaaaagacc | 960 |
| ccctgtaacc | gtaatggttt | tgtgctgcga | ttttacaag | tgctagtttg | acgtttgggg | 1020 |
| ttgcagactt | gataattgca | accttgtaat | accacttaag | accctctggc | atggttcatt | 1080 |
| agggccaatt | aatgtggctg | ggttatttgc | aacttaaact | gggggataat | gtcgcttgag | 1140 |
| ggagcgtttt | cgtttagga | atattgttt | tggtttcggg | tttgaaggca | gctgtcaaaa | 1200 |
| aagcggcatg | gaaattcatt | gggctccatt | cgatacctcg | tgtttagaga | tcgttatcgc | 1260 |
| ctcagataaa | cggggcagag | aggtggggag | ataagcagtt | taccctcaag | atttgtagtg | 1320 |
| gcaagtccac | accctctct | ctaccttcat | attcactttt | cagtgagggc | cagtgacatt | 1380 |
| tatgctgcct | aacgtcatcg | cataggaaaa | gttaccttt | attggacggg | atttgactat | 1440 |
| agtgtcccaa | atgcgcttct | ccgtcttagc | ccatctctta | aaacaccctg | attaacgata | 1500 |

```
tactaacagt cttactctct tgagaatagg ctgagaattg ggataggtga aggtttggat      1560
aggtgaaggc agagaaaatt attttgaaca ttttactgga tacagttgta cctgaattta      1620
tatgaatgtg attttacggt tctgtgtttt tccattttc agtacttcga tatttgtttg       1680
gaaaggaaag aacttagaga tgtaatagca tttcatattg aggatctcaa gcaatgtaaa      1740
caaatgtagc ttaatctaga tgttttgtg agttatgata agggtcagct atatttaagt       1800
tatgtaagct aacaacgtag tgagaaacta ctacaccttc tcttctgctc tttaaaatct      1860
aaattttagt tggcctatat aaagtgtatc tcatttcata tatccaaaat ttggaggtag      1920
gcacatccag tcagaagtat gggttaaaaa gccttttccc agcctgtcgg aagataagca      1980
gatcagcatt gtttattttt caaagaaaac gtgcatggtt caccagttgg ttgtactcaa      2040
aggtttggat gtgtgactag ctggtaggag ggaaatttgg aagtaattag ggattgagaa      2100
ttctagcata gtatttatca aatgttatat gtattggttc tcagaaaagc aaacagccgt      2160
gattgaaaag aggtaggaat tttaatgatc acacttcctt tttttgaaat taaatacttt      2220
gacatcaact tgaaccttca gaataatcag atgtaatgaa ttataatgtc tgtgattaac      2280
aaagctacac gttcagtgag cggcaggatg aatagccaag cttagttcga tacacttttg      2340
ccctcagctg tgcaaatgga ttgcattgta cttttaaatg tggcatgctg aatgggagca      2400
ggggacatgg cttttattc tggaagatag aaactactct tctggtaaca agaatttga        2460 ttcggagtta actaaaaggt tcatttaaca agctgcctct tactaatcgg atcaggaaga      2520
taatgtgact ttagagctta tgatgttttc ccccgtttt tgttttttgt tttgtagttg       2580
atattcactg atggactcca aagaatcatt aactcctggt agagaagaaa accccagcag      2640
tgtgcttgct caggagaggg gagatgtgat ggacttctat aaaaccctaa gaggaggagc      2700
tactgtgaag gtttctgcgt cttcaccctc actggctgtc gcttctcaat cagactccaa      2760
gcagcgaaga cttttggttg attttccaaa aggctcagta agcaatgcgc agcagccaga      2820
tctgtccaaa gcagtttcac tctcaatggg actgtatatg ggagagacag aaacaaaagt      2880
gatgggaaat gacctgggat tcccacagca gggccaaatc agccttttcct cgggggaaac     2940 agacttaaag cttttggaag aaagcattgc aaacctcaat aggtcgacca gtgttccaga      3000
gaaccccaag agttcagcat ccactgctgt gtctgctgcc cccacagaga aggagttttcc     3060 aaaaactcac tctgatgtat cttcagaaca gcaacatttg aagggccaga ctggcaccaa      3120
cggtggcaat gtgaaattgt ataccacaga ccaaagcacc tttgacattt tgcaggattt      3180
ggagttttct tctgggtccc caggtaaaga gacgaatgag agtccttgga gatcagacct      3240
gttgatagat gaaaactgtt tgctttctcc tctggcggga gaagacgatt cattcctttt      3300
ggaaggaaac tcgaatgagg actgcaagcc tctcattta ccggacacta aacccaaaat       3360
taaggataat ggagatctgg ttttgtcaag ccccagtaat gtaacactgc cccaagtgaa      3420
aacagaaaaa gaagatttca tcgaactctg caccctggg gtaattaagc aagagaaact       3480
gggcacagtt tactgtcagg caagcttttcc tggagcaaat ataattggta ataaaatgtc     3540
tgccatttct gttcatggtg tgagtacctc tggaggacag atgtaccact atgacatgaa      3600
tacagcatcc ctttctcaac agcaggatca gaagcctatt tttaatgtca ttccaccaat      3660
tcccgttggt tccgaaaatt ggaataggtg ccaaggatct ggagatgaca acttgacttc      3720
tctggggact ctgaacttcc ctggtcgaac agttttttct aatggctatt caaggtaaga     3780
tcagtgtttt tctgtttctt aagaatggta catttaaggt agattaatag atgtaaatct      3840
tcattgattt atatgtgttc tctaaagatt catgtgcttt tttatatgaa taagtttaag      3900
```

-continued

```
tggccttttg aaagtaggaa aggtagacaa cctaagtgac atctgtacgt aaccatttca    3960
ggttttttcc ttaaatagtg gttttcagta tcccattggc caacggtgag gattttattt    4020
aacattttta aaataatgtt gctcattaac agatatctta acgaaaaatt atataaattc    4080
aggagagtat aatgtctcat aatatcatat tgtgttgtgc atggtcattc agctgtttta    4140
gaatatgttc ttatattaca ataaatgata cccttactta catagtcaaa agttgtgctg    4200
ccttatttgt aaattcgtta agtgttagct tgagattaaa gagttaaaag cagaagtact    4260
aacaaagagc cctattcttc aaactgaatc ttctgttaaa gaatttgagt tttgaagttg    4320
ctaaagcaat gcagtgaaca gtgtaccaga ccatagtatt agacacaggt cttgctcaca    4380
gggttcttgc cataaagtag acaagttatg tctgctgatc aatctcttta agagaggaat    4440
tggtgtcaac atggtgcaaa acaaaatttt acgttcaaat gttcctgcaa gttctcaagt    4500
agataactga tggccaaaat tgttaagctt caattttcag ctttcgtttg attttttctct    4560 tttttttact cagtcgttta taagcatact gatattttg tctgacccaa aaaggtcaga    4620
aaatggaatt atcagaaaaa agttctaaat gtagatatac gtgttggtag gggtgaattt    4680
ctctaccccg taacctcatc cccaattcag ataaatgcta ggttttatat ccattttagt    4740
tgtgaaggaa aatataaaaa tgtggattgt agtgacacaa gattgattaa tcagcgggtt    4800
tttttaaaag aagacatggt agacagtgat ttatttgtat gtaactattg aagttttttc    4860
ttaaatgtta gtgatattca tcgttcccat taactagtta ttcagatttt tgaaaatcct    4920
ttttctgtga aagctatcct aacctggagg atgtctcttt tctttcctct gtacttaaga    4980
agcttttctt gttagggaaa taatttagaa ttagatttag gctatgttct gttcttctaa    5040
aaggcttagt tgtcaaaaaa aaaaaaaaaa aaaccaaaaa accttggttc ttacatgtct    5100
taatgtgaac tacctcctaa tctattgttt aaataattat cctttattta gaagaacact    5160
acttcaacct gagttgaagg tttaaaaatct tttcagtaag gagatttgag atctttatta    5220
ttgcataagc tgttgtgttt taaatgctaa aagacatgct gtgttttaaa attttcaatt    5280
gcaaattttt ggcaatagaa ttcgcatact tggttttctt aaaagagtta agtacggttg    5340
atttgactaa gctatctgta ggaaactctt aaattgattt ataaaacatg taattataca    5400
aagaaaaata aaacatctta ggaaactctt ggggattatt aatggatttt gccctgataa    5460
tcatcatggc atggttttca ttttccttac tataaagaaa aggcaaggga caaaacttat    5520
tttccatttg ctatgaactt ttaaacccta taaaatctgg gatatagagt ataagtagat    5580
gaacatagtt actcttaaat cactaaaggt gattttaatg ctttaacttt tatagtactt    5640
catgacataa agtatcttta cgtattttta atttgggtcc cataacctta tggaggtagt    5700
aggcaaggca atgatgatgc ggctctttag aagttctta atatcaaatg aaattattat    5760
ttttatgcca atctgtgatt gggaaatata atcagtagtc tgtgtcctaa caagaaggta    5820
taatacttta tacagggtat tttgttaata tttgaagatt ttatacctta tggcattaac    5880
ttagcactgg gaactatgat tacccaaaac aaagcttcat ccaaataaat tgaaacagtg    5940 tttctttttaa accatcattg aattagtcta ttgtttccaa acaacagccc tgatatagct    6000
aaaattagtt gctttctctt ctctatatgt tacatgactg tagccaaaca tttgctatga    6060
ccagtgaccc tgagtgatca gcaaataatc aacacattga gaccacaact tgaatactga    6120
ccttctgact ttacgaagaa aaatattaaa tgccactaat aacttgaatt ccttttaaat    6180 taaaaaagt tataaattgc aatttgactt tttaaaatgc cacctaaaat tgttttatc    6240
```

-continued

```
agaatactta aaaaaaaatc ctcactttat tctctggggg tgggaagagg caattccttc    6300
cttccaccac aacattgaat tatcacataa aattgtaaaa ttatgaatat tatgattgag    6360
cttagtaaag cattttctaa gttcatttat agtaaaacaa gagaaacctt attctcaaaa    6420
tctattcttt aagtaaaaca aactagtcat tctaacttaa tatgctttta aaaatactga    6480
agttcagtac atttagcata aacttattga cgaaggcaca tttctgcatt atttgatttt    6540
cagccttgtt tcatttaagc attaatgaca gaggtagaga acagaaatgg ttttaggtgg    6600
tattagagct tttattggga ttatgttgaa atttttagtgt taaaaaattg ttcgtatcct    6660
gaagggaggg attattggag agaatgaatg atgtaggatg aacttgtaaa ttcagttttc    6720
ggcagagtct aaaattaagt gatgattggc acttaatgaa gctactaaaa tttatgtaga    6780
ttttaatgtc tcattagtaa tcgcatctgt atctggtttt ataaaagtaa tgaaattgaa    6840
gacctgtaca aatacagaat gaatgaagca aattctgcta acatcatgtt gaatgttttc    6900
tcagaaaaag aggaaatacg aagagaagag atttgttttg actgtgattt accctcaccc    6960
ccatggatac tttctttact tcctaccttt tttcttttc ttttccttct aaagattctg    7020
gcaatgggtg tttcagtgtt ttttaagctt aatatttctg gtactcattt atgtaaagtg    7080
atttctgaat gttaaaggag atttcttttt aaatatattt tcacttattt ttagctttat    7140
gatgagaatc ttatttttta aatctgtaac ttgttatggc tacatgatta gtaaaaaaag    7200
tttttaaaac acactgtgta ttcaggtgtg tcattttagt gtgaaatgac taatgcagaa    7260
atatgtgact agcatgtggt cagattttat tgaaattact tacgatgttt ctatggctag    7320
tccccttgta tttttataat tggtaacata attcatatgt tattttggtc ttgtctattt    7380
gtgttacatg tattttagtc tgaccacttt tgctacttat ttaatgttta tacattttat    7440
gaaagactta ttctgaaata taccttgcat aaatgtaggt taaatgcaaa ttgtattaat    7500
agtgaaatgg atatgtgggt agagatcact ttagggcct tttgagattt agtgaaggaa     7560
agattggatc aaaagggttt actttaatgt gactgcctaa tgtgaaagtc ggaacatctg    7620
cattaattgg ttagttacat aaatcttagt ctactctggc ctgcaggtga ctgaaacagc    7680
ccaggaaatc ttaatttaca ttaagcttag acaaggtctg aggcttaggc ttagttctta    7740
aagcacattc tttttacttt taatgattat tcctaatttt aatgagcagt gggttctcat    7800
tgtgtactag tacttaggtg ggcaaattaa ataagcaaaa taggtttgtg ctgaatagca    7860
tttacccttc tgaggacatc ctggtaatat tttcatcaag agtaattgtg taatgcaata    7920
tttacaggta tttgccagat taatgggcac ttgttttcat atttctgagt catggaaaat    7980
atacattgat gattcctgtt gcataaagag ttttcaagaa aattttgttg aattaagcta    8040
taactacaaa aaaaaatcca ttacatattg accttagaa aggattttta aaagcccatg     8100
ctgtccttat ttctgcagct tcagagagcc gactgctctt attttcttct ggcatattct    8160
attaatactt gggttttgta tttttcaagt aaataaaata ttcctattga gaatttcaat    8220 tttaaaaag aaaaggtcta ctaagtgttc ctttccctgt tgaattatgt gtgatcattt      8280
ctatgctaaa ctagattagg gtgtgacttg tgatggtgat ttttgttcat ttacatatt     8340 aagaaagaaa tagaatttta ttgcagttca aaattatttg tagacagtgg ttttaacccc    8400
cagacaccta attgtgacag gttgctttcc ttagtgctca atactgttgt aaatgtctct    8460
aaatacagaa tttccagtgg agttcatgaa ttaattgggg gtggagggtg aagagggagg    8520
agcaacagag atgtgggatg ctatagataa gtttaggaat atccagatca gttctgaaaa    8580
ctaacagttt ggatcaactg tcatgaatta gaggtttaag aaaagaaaaa tttaggacta    8640
```

```
taggtacaag ggaatgcatc aatcagaatt acaatttaat ttctttttatt tcaggtagaa    8700 atctaaaact gaccatggct atataatact aattttttgag ttatgttgtt tcttactatg    8760
ctttattatc aaaaaaggat aaaatgcaca ttttacttga agattatttt agctaagatt    8820
aagttcatat ttttctcatt tttatttaag ctgctgttta ataaatgaaa atctaatgac    8880
ttgaatgtag tcgacctaat gtcttaatgt tgatataatc atttcatata tcatagtgcc    8940
cttttacagc cattgtcaac tgactggaga gcaacccttt tctttggtaa tatatttcta    9000
tgggttatgt attttttctgc tggaatattg agaaaattaa ttttttcataa tatgcagaat    9060 aaattatggg gttctgcaag tgctagacag tcacttaaac catttatatt gcaatacatt    9120
ccttaaattc agtattttga atgaaagtgt gttatccccg aattttatca cttgtccaat    9180
ttaaatatta attacatccc aatagagctg catgcttaaa catgcttttt cagagtaacc    9240
caagtattaa tttcgagtgc ttttaaatat tttttctttt tagcaagttt caacaacatt    9300
aatcctgtct ataatgcagc aagttcagtg aaagtacctg ttgttttata atttttttt    9360 cattctcact gtagggcacc aaaaatatat ataaggggaa aaagttttta atgatatgat    9420
tagttgtaaa tgtttacgca ttatcttacc ttgaattttt atttttgtaa ctaataattt    9480
gagagttcaa taagtatgca gtgtttaaga catagtttgt tgcaaaaagt gttaacttac    9540
tatttctttt tacaataaaa ttagcccttta ttctagttga tttcataact gtccataata    9600
tttagctgtg gctattatga aagtatattt gatagccaaa ttttgaaagc tattatgaaa    9660
tgatacaatt cactacatga tttattattt catgctggtt ggggcagtgc tgtgacttat    9720
gaccttatga ttgtcacatg ctgaacacta aagctctacc agtttgttat ggacactgtt    9780
ttactttatg ttatcgtttt aatgttttct tttataatta ttgaggataa gagcttcctt    9840
aattttaaga ctatttaaat tgcagatttt gcttttttat ttttttaacc atcccttcca    9900
aagaatttga tttagatatt cagtagtaga aacagaagaa aaatactcaa ctaaaagtcc    9960
aaagacctag tttctaatgc taagggagac agtccatggc ctccaactag gtactttgga   10020
gtcaaaaata cttttctttac aactgtgttt gaattgtttt caaaacacct gtgtgtgtgt   10080
ttctaaaatt ccacaatcct tttaacccgt caatttgatg agggaagtaa ttagggtagg   10140
gaatggtata acaaagttgg ttcttttgaca ttttctttat agattatcga atgtaagaca   10200
aatagatgtg aatgcagatt tggtgttttt ataagataag gatttaaaat aatgtagttg   10260
gtgatatata aaaataaaact attgctgctg ttagcacccg agaggtgggg ctcttgggtt   10320
ctcagagctt gttttctatg ttcgttacag ttattttaga ttagaactta aaagaacttg   10380
agagtttccc taattctacc ccctaatttt ttcgaatgag aaattgagat ccatagaaag   10440
tgttgaggta agatcacaa aacacttaat gagcggtgtt gccagtttga atatctcaat   10500
tcttagttat ctaagttccc tggtaggctt ctttaattat ctgggtctct tctagacatc   10560
tggaacaaat agttgattga cataatacag actagccaca tattttataa gagttacttt   10620
tgactcattt agattttttaa aatatacagt gtctgtattc ttctctattc attttgttaa   10680
ttttttttta cctaataatg attaagcacc aattatgtga cagcactatg ctaagcactt   10740
tgcatgcatt catctcattt aaatctcaac tctgtgaaag ttttttattct agttactgta   10800 ttaagtctca attctgtcaa tatccatgaa gcacagaagg cagctgttat ttaccttaat   10860
tttacagatg tgaaaactaa aggcatttaa agagaaaaag aaaaaaaaaa ccaggaaacc   10920
ttaacactta tctgaaggga aatatttaat attgggtatg ttagttcctc atgtatcttt   10980
```

-continued

```
aataattttt gtcaacagcg aatctttaaa taaaatataa aggatcaggc ctctgctctc    11040
ctgcatatat ttgtaaagtc acttactgct ttttgtcaca gtttcaattt ctgtaaaata    11100
gtgagagggt ttttacctga caggatttgt gcatgtacgt ttactttgaa aattaaaaag    11160
cattaggcca ggcgcggtgg ctcacgcctg taatcccagc actttgggag ccgaggcgg     11220 gcagatcatg aggtcaggag attgagacca tcctggctaa cacggtgaaa ccctgtctct    11280
actaaaaata cagaaaatta gccgggcatg gtggctggtg cctgtagtcc cagctactcg    11340
ggagcctgag gcaggagaat ggtgtgaacc tgggaggcgg agcttgcagt gagccgaggt    11400
tgcaccactg cactccagcc tgggcgacag agcgagtctc cgtctcaaaa aaagaaaaa     11460 aaaaagaaaa gaaattaaa aagcattata aaaatgcaag gtggaatttt taaagctctg     11520
ccaagtccac ttagcttaaa ccagcatgac tctcattggc taagtacgtt atgacatctg    11580
tgactgtggt gtaggtattg cctataatca agaatctttt agggtctgct atgtgcaatc    11640 cctgaaggt catggatcgc agtttcataa agactgctgt attttaaagc cttcaaatgc     11700
caacgtagta tcttcacaat gattttttt ttcagtttta ttattttttg aaagcgcctt     11760
cgacaaagtt ttcagtggat tttgttgagg gatattaagt atgccatcta cataatagcc    11820
atagtgataa ctccaaccac attgttatat ttttattaat aaatgctaga gtattctctt    11880
tctggtattt cctattctga tattttata taatcaagta tgcaaagatt ctttgtcatt     11940 ggaaaccta atttgcctga aaatgggaat gaaattttca ggtttaaaat ttttttacat     12000
ttattacatt tattgaagct gtctgaaaaa gctcttgagt atattgaata ccaaaattta    12060
tcctaactgc ataaagttgg gaggattgtg aaacttgact gcactgactt gttttcttta    12120
ttgatcaaat ggttgaaaaa aacttcagtt aaacaaattt gatctattaa accaaagtta    12180
taaaagcaga ggaaagcata gaattattaa acggcagttt aaattggtaa ataccgat      12240 gtagaaccta agtttgtagg cagctttctt agatggaaac ttaaaaaaat tttaatcaga    12300
acattatgtg aaatttgtca tctggaattc agctgggttt attaaggaca agtgtatgg     12360 ctataaaata gattgagttt tttttttaaa acagaaaacc caaaataaat gttctaagtt    12420
tccaccttag gaggctatgt atattgctcc tctttgaaac tgccttcaga accaccttgt    12480
aagccataaa agaaaatcgg actcattgca ctatagtaac acctaactgt tcttgctcaa    12540
agaaaatgta tttatccctt agctttattt gtgtgactcc aaatcatatg agtattgcca    12600
gatatttaga aatttaatcc tctctcgaat gataacattt attttctttg agggttttta    12660
aaagagccca catagatatt tctacagaaa atgtttaatt ctgttttgaa tatgcctgga    12720
ataagtgaat agcttcccag ggtgactatt ctgaaatggg tgatgcttag tggttaagtt    12780
ctgatttgtg ttttcttgaa gttattaagg aactttatga taacagttta tatattccct    12840
cttcttggca tagtaatgaa gtaatagaga ctattcacct ctaagcctga ttttttaaat    12900
aagtgtttat tttatgttta agtaaggtag gtctgctttt ggcttggact tgaatttggc    12960
aatagcagat ataaagtaaa cataatgtga attcctacaa cagtctccca aacagtttaa    13020
tttctcattc atacacattt cccttagtgt atcagggaat taagtatctg attatcagta    13080
tagcaagaac aactcaagta tactgaagtt atttatactc ataaaatagt ttgagttata    13140
gctacaatat aaaattaata tattttgac ttttattcct cacaacctga aaaaacctc      13200 tgcgattact gatagtactt ttaaaaacta aatgaatttt gttactacta tttgctaaat    13260
ttagtcatgt ttactgttca aaaaatgcta ggttaaaatg gatcctaatc tttgaaatga    13320
tgaagacatg tgtagtggtg tcaaaaatag gatattcatt ttgtaactat tctgttagtg    13380
```

```
ccgaagttct tagaatttct ttgtgacaac agcctgctta agaactttag atttttttaga    13440 attgtactaa aagcaaactg ttttcttgga tatttgttct ttctccccaa aagatgattt    13500
ataagttttc agagctaaga aatgggaagg aagagccatc ctagcatggc aggtaatgtt    13560
ttactgctaa caggttttct ctgcactgct ttatttgcct tgaacctctt actttgttct    13620
gtcagctggg aggctggtag attttctatt aggtagcaaa tgcttctcat cactaaacac    13680
atatcatggg ctggtgttag tgcagtctgt ggatgggcac tacatttttta atcaagaaat    13740 gttttttaaag gaaagacaaa ttggtgaagt aatttctaat tcagtatttt agggatgagt    13800 gacctttttaa ttgataatga tatttaacag agctgtacag tgctttgggg gtcccacaga    13860
catgtttaaa caagaaaaca gtaaataagg aagccagaag gaaaagttat aaaactatta    13920
agaaagaaaa tgaaaattct aaacttcaat tctggtgcct ggctaaattt gattttttgta    13980 tgcctcagtg tttctctatg gacactggga atcaataag caacctagct acgttattat    14040
gttcgtaagt ggaagaacta aagaactaca aagacatgtt ctaggccaag aattctggtg    14100
gtaggtagag tgggaggtta actagatgat ctccaaggtc cttctaattg cacttggcag    14160
cagcaagcat ttatcaagct agacactggg catatggaga tgaagaagat gaatatcccc    14220
agcagcatgg agagcactct gatgatagtc atccctgcct ccccctccct cagtttgctt    14280
tttgaaatgt gagcttgaaa gatctcaaac tccttcctgg gaagacataa ctgaaacttc    14340
atggaggaaa gtgcatgaat gaatgggaaa caagatttga ttcaactatt tggaataaga    14400
aaaggggcaa caaggagtct gaaacaaatg aaagaaaaga tggaaagaat tagttgacta    14460
gatgaggact gagtacatag gaatgagcca acaggagact tcagcaacta atggatgaaa    14520
gtattatgtg catgcatgtt gtcatcaaat atcacatgat acaagacaag gagaaaacat    14580
gactttcacc ataacctcag tttgtgtacc ctagttgcaa gatatttttt tcttctagtc    14640
acttaagaat atccttattg tctaggagaa ataatcctct ttctgggctc cccagtgtat    14700
aagcccaaat ctgaggaaaa tttacctgaa atgttctttc cccagatacc cacatggttt    14760
actctctcat ttaaatgtca gctctgtaaa agagatctct gactgctcta tctgaaatag    14820
tagaatcttt cacagtcttt ccttcttctt gacatcatct atttgtgtct tatctgctca    14880
cctgctacaa tgtaagctcc atgagagcag tgatactgtc tgccttgctt actcctgtat    14940
gccagcgtct agaatagtgt ctagcacata gtaagacctc tacaaataca tgttgaatac    15000
ctaaataaac aaaatttaac atataaacca aaaagatata taggaatgga ttatatttct    15060
aatctttctc gagtgaggaa aatgtcagca gatagtgaat atcactgaga gagagatgat    15120
agcccaggtt atcttcccca gatagaaata agccttaaga ctgacaggtg tatatgaata    15180
cagagagtat acataaagaa gatgtatttt caattgacag tctctaaatt tgctttaaga    15240
cttcgaaatg gattgctttt cataatttct tagaataact ctggtctgtt taccattgaa    15300
aaattagagt agccaatgtt tgtaaatgaa gggttagagg gttttttcct ttggtggttt    15360
gttaaaagct tgctcaaggc agtaacatag taaattgtca atataggaac ttttgtagca    15420
gaagctttat gcttttcact tttataagaa ttgagattat ttaagcagat gagtctaatg    15480
tatatgtttg tactgactta cctagaaggt caggcaagaa atcggtttcc tcattttttca    15540 gataagtgtg tgtgtaatca ctgagtacct taagagagga ggggtgtttt attttttgcct    15600 gaattttcaa aatatctttc ttcagcttat ttatatttta gatttgactt attctgtcta    15660
tagtatataa cagtcaggag gttggtagga taagttcatc tcttctacta agagtttatag    15720
```

-continued

```
gagagttcaa cctaatatgg caatgacagt cgcagaaaag agaaaatgca agttaagtag    15780
gtgttagcca tagcaagaaa atcagatgag gtcatttaag aatgaactgc tctaatgttc    15840
aggaaaaaag aggggaggga caaggacagg gctctagaag gcaaccaaag agagcagcca    15900
caaaataaat gaatagctga agaattagga gacaacaatc ttaaaatgtg gcagggagag    15960
ggtagttgtc acattaacta gcatagaaga gacagaatag aataacataa atatatgagt    16020
gattattgtt cttgaaacca gtctttaaaa catgggaaca ttcccaaaaa tcaaagccag    16080
ataaattagg gaaatcttaa atggcacaat ataactagtg atttcgttta taattttttt    16140
aaaaaggaga cttaaatttg aaatttagat gtaattaaag cagataataa gaaacatact    16200
tctgagacca caaagaccct gagattcagt taagagtaag gtagaaaggc tggaagccag    16260
aagggaatta agtttctgtt ccctgagaag ccaacacaac aggaaaaaac tggccacacc    16320
ctagttcaaa ctcttattac tcttatcaat agtctcctaa ttgtttctct agttttctcc    16380
tctcccttct taattcattc tgcagtctac tgccagatta atcttcctag aacaccactt    16440
tcagtattat tcccctgatc aaaaaatgtc tgtggttttg ttgctcatag catagtggtt    16500
ctccttcttt gtaccacagc ccatatgcac gatgatagat ggtgggtagc cacatgaact    16560
ctccataacc tttggaggat ttgggttata cacagtctgt tatccaagaa agcatatctg    16620
agtgtaagtg agcattatag ggatagtctt ataattgact ccttttaaaa tttgttcttc    16680
tttttgcaaa tgccccttca gaatttacag aaatagtgtg ttcattccat cagtaaaatt    16740
atacccaaa atgttaataa gcttatttcc atcacgtctc ctttcctatt tctttctttc     16800
ctctttcttc ctgcacatct ccccttatcc tccacatttc tctgtaatta cataagcata    16860
aacagacaca tatgagattt tctgggttgc ttgcctttaa ataaaagaat gggattatct    16920
tatacccctt tgtctgcagc ttgcttttct cacctaacaa gtacaccctg aacatccttc    16980
caggttaaca gatgcggatc ccattctttt aaatagacaa tattctattc atgtggtttc    17040
gtgattttg ccactacaag caagtttcta ataaacaccc ttttctatgt accctttaca     17100
aatagcaact tttttctaa atataaatgc tatggtttgg ctctgtatcc ccacccaaat     17160
ctcatcttga attataatcc tcacatatca ggggaggggc ctggtgaaag gtgattgaat    17220
cctggaggca gacttctcct ctgctgttct catgatagtg agttctcatg agatctggtt    17280
gcttgaaaat gtatggcact tccctcttca ctcactgtct ctcctgctct gccatgtgaa    17340
aacatggttt ctttgccttc cactgtgagt gtaagtttcc tgaggcctcc cagtaatgct    17400
tcctgttaag cctgtggaac tatgagtcag ttgaacctct tttctttgta agttacccag    17460
tctcagttag ttcttatag cactgtgaaa atggactagt acagaaactt ggtaccagga     17520
cagtggggca ttgctataaa gatacatgaa aatgcggaag caactttgta actggataat    17580
gggcagaggt tgcaacagtt tggaggactc agaagaagac aggaagatga gggaatgttt    17640
ggaacttcct agagacatgt tgaatggttt tgaccaaaat gctgatagtt atatggacaa    17700
taaagtccag gctgaggtgg tctcaggtgg agatgaggca cttattggga actggagcaa    17760
agttcacttt tgctttgctt tagcaaatag actgacagca ttttgcccct gccctagaga    17820
tctgtggatc tttgaacttg agagagatga tttagagttc gtggcagaag aaatttctaa    17880
gtagcaaagc attcaatatg tggcctggct gctcctaaca acatcagtc atatgtgttc     17940
acaaagagat ggtctgaagt tggaacttag gtttaaaaga gaagcagagc ataaaagttt    18000
ggaaaatttg cagcctgacc ttgtggtaga aaagaaaaac ctattttctg gggagcaatt    18060
caagtgagct gcagaaatat gcatagatga agagtagcct aatgttaata gccagtagaa    18120
```

-continued

```
tagggaaaat gtttccaggg catgtcagag accttcatgg cagcccttcc tatcacaggc    18180
ctggaggtct aggaggaaaa atggttttcg tgggccaggc ccaggggttgc gctgctctct   18240 gcagcctcag acatggtgc cctgcatccc agctgctcta gctccagctg tggctaaaag    18300
gggccaggag ataatcttgg gctgttgctt cagagggggt aagcctcaaa ccttggcagc   18360
cttcatgtgg tgttgggcct atgggtgtgc agaaggcaag agttgaggct tgaaagcctc   18420
tgccttgatt tcaggatgta tggaaatgcc tggatgtcca tgcattctgc aggggcagag   18480
ccctcatgga gatcctctgc tagggcagtg cagaggagat acatgggtt agagccccca    18540 cacagagacc ccactggggc actgcctagt ggagccgtga agagggat accatcctcc     18600 agactccaga gtggtagatc cactgacagc tttcaccatg tgcctggaaa agctgtaggc   18660
actcaatgct agcctgtgaa agcagctgca gggtctgtac ccagcagagc caccagggca   18720
gagctgtcca aggccttggg agctcacccc ttgtgtcagc gtggcttgga catgagacgt   18780
ggagtcaaag gagatcattt tggatttta agatttaatg actgtcctgc aggttttgg    18840 acatgcatgg ggcctgtagc ctcttttgtct taaccaattt ctctagtttg aatggggga   18900 atttacccaa tgcctgtatc ccaattttt cttggaagta actagttttt gattttacag    18960
tctcataagc agagtggact tgccttgacc caagaagact ttgtacttgg acttttgagt   19020
taatgctgga aggagttaag acttccgggg actattgaga atgcaagatt gtgttttgaa   19080
atgtaagaac atgagattta ggaggggccg ggggcagaat aatatggctt ggctgtgtgt   19140
ccccacccaa atctcaatca cttgtaatcc ccacatgtca ggggagggc ctagtgggag    19200 gtgactgaat cacaagggtg gacttccctc ttgttgttct catgatcgtg agttctcatg   19260
agacctggtt gtttgaaagt gtgtggcact tccccttct ctctctgtct cctcctctgc    19320
catgtgaaca tgtgcttgct tctccttcaa cttccaccag gattctaagt ttcctgaggc   19380
ctctcagtca tgcttccttt gaagcctgtg gaactgtaag tcaattaagt ctctgttctt   19440
cataaattat ccagacacag gtagttcttt attgcagtgt gaaacggaa taatacaata    19500 gatttcccca aagttgggtt cctgagtcag gggtatgtgt atttaaaatt ttaacagata   19560
tttccaaatt acttttttcg aggattatgg caagtcacag ttcccctgg cagtgtttat    19620 actttctttt ataataaaaa tacataaatc attattacta acaaattcct tgccatgagt   19680
cctaaattga taacaacata ccagtgtgcc atataacata gctgaggact gttgcagtct   19740
agaattcagg ctccttctct ctgcttttaa caatatgtgt aatgttcaag accaatttag   19800
tgccacttat tttgtatgct ttcctttatg tagtccaggc catagccccc cacctcatct   19860
gatggtatcc tctggcagcc acagaccaca cagttctttc tacctaaatt agtcattagc   19920
acatagtagg tacccagtaa atgtttgttg aattaatact gtttatatat ttctaattta   19980
tctccaagta aatccagtct ccttaaggac aaggaacgtt ttcactataa cacctagcac   20040
ttaaggtact caatttaggt agggctgttt gaacaaagaa ccacagagga agcaaatagc    20100
atggccttgc ctttaataca tatattttac tttctcttag ggaaaactgg aactgtaaga   20160
atctagtaac aataataaga acagcacttt tattgagcag ttactatatg tgaggcacag   20220
ttcaaactgc agaggataca acagtggaca aagcttagt tgtttctgcc tttctgaagc    20280 ttatggtttta tgggtgttac attcaagaca tttgtaggac acattctaaa atgccatcca   20340
atttcaggct ctttccagca gaaactgtgg aatattttc cgttcattca gcatttactt    20400
agtgcctgct ctgccaggaa ttgaagagaa agcccaaaga caggcagacc ttacctgaga   20460
```

-continued

```
ggtagtgaac tgaccaggat gactgtgggc agtagacttg tttcccaaac tagcctcacc   20520
atttctgtat ttgcatatac gaggaaagga ttagatatag ggattcatgt cagcatacac   20580
cccagggaca tttgttttta gtgaaaggtg ccagtcttca tccctgtacc cagtacacaa   20640
accacgaaga agtatgctcc cgtcattgtc aaagaatcat agaattccaa atggagctag   20700
ttttgatatc cagatctcac ttcatatgag gaaactaggt ccagtattgt gagtaagaat   20760
taggactctt cagattccct gggtatgaat ctgactaaca actgtgtgaa cttgaccaaa   20820
ttcataaccc tgtaaactct gtttcctcac ttttaaaatg gcacaacaa agtgatgcat    20880 gtaaactgca tagcacagtg tctggcactt aaaaagcact cctgaagtta tttttagtga   20940
tgtgttttaa gattagacaa ctccttaatg ccaaaggttt ttacttgaga actctgtctg   21000
ttgtgccata ctacacgctg ttcataagat aagcctttt cattaattga tctcaaactg    21060
gcttcattat gatcttaact ttatttcagt tttatttta aaatttattt ttaattttta    21120
tgggtatata gtaggcatat atatttatgg ggtacaggtc atgttttaat gcaagcatgc   21180
aattgtgggg gtgatatata attgactggg gtgagatatc tcattgtagt tttgatttgc   21240
atttctctga tgattaagga tgttgaacat ttcttcatac acctgttggc catttgtatg   21300
tcttttgaga aatgtctatt cagatctttt gtccattttt taagttggat tgtttgattt   21360
tttcctgttg tctgaactct ttatatattc tagttattaa tcccttctca gatgggtagc   21420
ttgcaaatat tttcttccat tttgtgggtt gcttctttgt tgtttccgtt gctgtgcaga   21480
agttttttag cttgatgtga tcccatttgt ccattttgc attggttgcc tgtgcatttg    21540
aggtattact aaagaaatct tgcccatac cagtgtcctg gagagcttcc caaatgtttt    21600
cttttagtat cctagtttca ggtcttagat ttagggcttt agtccatttt tatttgattt   21660
ttatatgtgg tgagagatag gggtctagtt tcattctgcc tatggatatc cagttttccc   21720
agcaccattt attgaagaga ctgtcctttc cctagtgtat gttcttggca cctttgctga   21780
aaatgagttc actgtaggtg tatgaatttg tttctgggtt ctctaggtct gtgtatctgt   21840
ttttatgcta gaactatgtt gtttgggtta ttatagtttt gtagcataat ttgaagtcag   21900
ataatgtaat tcctccagtt ttatttttt tgttcaggat ggctttggct attccggggc    21960
ttttgtggtt ccatataaat cctatgattt tttttttcta tttctgtgaa gaatgtcatt   22020
gatatttatt aataaagatt gcattgaatc tgtagattgc tttgggtagt atggacattt    22080
taacaatatt gattcttcca atccatgagc atggactatc tttctttttt tgtgtgtcct   22140
cttcaatatt tttcctcagt gttttattgt tttcattgta gagctctttc acttcttcg    22200 ttgagtttat tcctaggtgt tttattttat ctgtagctat tgtaaatgag attactttct   22260
gatttctttt ttagattgtc ctctgttggc atctagaaat gccacagatt tttgtatgtt   22320
gattttgtat cctgtaactg tactgaattt atctgttcta atatttttt ggtggagtct    22380 ttaggctttt ccaataagat catacagtct gcaaacaaga ataatttgac ttcttccatt   22440
ccatttggga ttccctttat atctttctct tgtctgatta ctctaggtag gtcttccagt   22500
acttccagtt gaataacagt gggcactctt gtcttgttgt agatcttaga agaaaggctt   22560 tcagttttc cccattcagt atgatactag ctgtcagttt gttgcagatg cataacttt     22620 caaactaatt gattatagtt aggaagtgga tactttaact tgtggtacca ttatcagatt   22680
tatatttcgg ccataagctt gaagaggagc tgaaaaatgc atatgtgatg catatgcttc   22740
ctatttggct ctcttctccc acccccctgc cctataatcc acacaagttc ctctctcagt   22800
cactcatcaa ctacttgaac ctctgaggaa cttggggtta aggtaaatta gaataaaact   22860
```

```
gtctgaagaa gagcaagcct ttcatgtctt gagaaattct tggggtttta gaaataactt    22920
cattgctttt tttctccagt tactttggct tcttcttaaa gagaatacta cactttgaa    22980
cgtcataata ctaaggttct gcctcttcaa ataaagactt taaaaaaaaa tggttttttgt   23040
atgattcagt gtgaattaaa tcccacagtg taaaggactt tactttctta atgtagattt    23100
tcaaatacac aattactgat gtttataagt agatttatta caccaaagca cctagcaaat    23160
tcttgaatgg atcaggtctt attttcagt cttactttgc aaatttaagt caaataatta    23220
aggatttgtt aaatatttgt cttaatatca agcttttgca tatcggggcc ctcttttata    23280
agctttataa gcaatctttt gttttctctg cttgctcaaa gtagctatgt tgttgtatc    23340
tgttagtatt tgctctataa caaacatact gggtgccttc ccacttagat ttggcaatta    23400
tcactcctgt aaatgagata ttacataaga taggaaaaag aacagtatct ttccaagaag    23460
aatagtatcc ttccatatta acagtttaga gctgactgct tttaaaattt agtggcttta    23520
aaataacaac catttattat tcttcatgag tctacaaatg aggtgggcag ttctgctgat    23580
ctggccaagc tgaacttatc tcagctgggc acattcagcg tatctgctgt cagttggctg    23640
gttggctgta gcaatgaatg gtgaaagtag gctgcccctta acttttttcac acagtagcat    23700
tagagttaca aaagaaccag cagaaccatg caaaactctt taagacctag gcttggaaca    23760
actatatttc taccacattc tattggtcaa agcaaatcac ggggctagtc tagattcaag    23820
tgggtggagg agctgcaatt acactgcaaa ggagtgtgac tgtagggaga ggtgtttttt    23880
tattttatt tttttgcgat ttgtcacagt agttgtagga atcaggtgta tttaaaattc    23940
tgatccttct gtgatatccg aattgttcat gaaccttgcc tctggtggaa aggcagaatc    24000
attgtgacag aaggataaaa tcttggaatt tagagactaa caaggttca gattccagct    24060
ccatcactta tttctgcaat cctgcagaag ttaatcttcc tgataggcat tcagtaatga    24120
ttgattcacc tgaacctcag attctttatg tattttaaag aaagggctag gtaaatgcaa    24180
agcacttatg taactgcttt tattattgca aacctggctc ccacactcca ttcaaggtgt    24240
aagactcagt gtcttccttg aattaaaaag gaagagaaag tgtgttaggg aaaggaagag    24300
aaatatttga ctaattgtgg ccccaataaa gtgaccactc actgggggta ttttcctgta    24360
agaaaagaat ggttgaggct cagagttaag agatacaaat ccaaaagtct ccttgggta    24420
ggattccctg tgattcatgg gttgagaggt gtaacattag acacagtccc agtctagatt    24480
tttttttaa agaattgtag tccatcctat acacactggg tgccttaata ctatatgtgg    24540
caattatcac tcctataaat caggttttac ataagatagg aaaaagaaca gtatcattcc    24600
acattaacaa ttgaaagatg actgctttta aaaaattaaa agggccatat agaaataaaa    24660
tcacataaat ttcttgtgtt aaacatagtt gtcatattgg atgaggacta acacctaaa    24720
ttcatccaac tagtagtaat agaaaagatg aaacacacac acagtaaaac tagattaatt    24780
taatttatac aaagggccag atatctcaga attcagacag tcagagatgt tgactagagt    24840
taatgcctct tttaggagag gtaccaggta agtgttctca aagaactgga aactgagacc    24900
accacctctg gcattatcta tttgtgaaca caagcaagtc tgaattttc cgcaccatag    24960
ctacctttca tgtaagcttc ttttcttaga agaaagaag gtaacatttg ggtgtaattt    25020
tttattaagg gtgaaattta gtgtagagag taaaggcatt tggcatagaa gcccttagtt    25080
ttttttgttt ttaagttgaa ctgccagcct ttatggattg cagtcttcgc tgttttgatt    25140
gacatttccc aattcatttt gtattattta tttttttaag agacagggtc tcactctgtt    25200
```

```
acccaggctg gagtgcaatg gggcaaactt ggatcactgc agccttgaac tcctgggctc    25260
aagcaatcct cccacctcag cctcccaagt agcttggact ataggtgtgc accaccatcc    25320
ttggctaatt tttaaatct tttgtagaga cagggtagtg ctctgttgcc caggctggtc    25380
tcacattcct ggcctcagtt gatgctctgg tctcagcctt ccaaaatgct gggattacaa    25440
gtgtgagcca ctgcacctgg cccccaattt catcctttac aaagactact ttcaaccata    25500
aatcaacgga aacttcagct ccctcagaca tatttgggat ccaaggatat tttcccaaat    25560
gattaatgct aatttcatat caatacattt ttgcaaaacc tacaaaaatg gactagtaaa    25620
gaaagactct taatttggga aagacagtta cttggagaga agaaaacttt aagaggcagg    25680
tcgagttcag tgttcagaaa tgagaggatc ataagagat agccataaaa atgtttctcc    25740
ctatattgcc tgctgatagg gtgtatcagt gaaggtctta ctaaggacct tgtacctttt    25800
cagcgctgca ctgcgtgctc atagggagga aagataaatc atgtgttttt tctgacctca    25860
aaggagcctg tatctggcta gagagacatg atgcagacac atgaaataat taagaaacaa    25920
ttaactgtag caggtgctga agaatatacc aggaggtcag agaatggtag agctagtgtg    25980
ggcgaaggta tagcccagag catcatcaga tgattcttcc ttatgcaaat tcacatctcc    26040
tctgggtcaa gtatcatcct ggcatgcagc agctccatag gtaatgccct aaggctagcc    26100
tgaggcaagt tgcaaaagcc atcatattga gtcatggcct ttttttgtgt ggggggaggg    26160
gaatggcatc cccttcctgt ctgccaaatc aaggaataca gtgccctcct aaacctgctt    26220
tgttttagtg gattgttaaa aagaagtgaa tgaatttatg cttcattagg gaaggttac    26280 agtggaatac tgaggagtaa ggggtatttc tatttaacaa atgacataac ttgaaggaat    26340
gaaatcataa ggatggaatt tcaggcatta ataaaaagct gatgagagat actttgagac    26400
aaaagagcct tcccagtgta accgagatca cagcacctac ttcacataca caggaaacca    26460
gtcctatctg tctctcccat agagcagtag ctgccttgtt tttcctccct cctccatcat    26520
tcattctaaa tctccagtcc tccaccgcac cttatccaaa ccctgatacc cttaagtcac    26580
agatggtgaa tcagtcaaaa gtagtattaa aaactagtgg tacacagcta cacctggaat    26640
gcagtaagaa aaatacggat ttctgtacat catcttccct ccctgctctt accccattt    26700 aagagttaca gggtcagaac ccaagagtct gagttttga aagtccctaa aaattttgga    26760
tgatcaccta catttagaac cactgcacta agaaggacaa caaatatgcc aataaattct    26820
gttgccaagg aggtgattat gcaagctgga accctgataa catgaggaga atcccacaat    26880
agccaaatag tccatgtact agttacatta taataaagcc aaaagcagca ggcctacctg    26940
actttctcct gaggtctatc atgagcttag agagaaggaa cgtggacata tagaggtagc    27000
tctagatgga gaagggcact aggtgtcatg gaaagaatca tgtgcaagaa gtaaagaggt    27060
gctctgaatg tcctagccct gcttaggtgt ctgtgtcctc acatgagaat ttatccacag    27120
ttctttcccg ctgtaacaat ctttggttcc aactgcattt gtgagacagc aaaaagctat    27180
ggtccagtct ccttccattg tatcatctca tcaatgtatt tctcccacta cccttgtgtg    27240
aaatacaaac ttttttggct tattgtgatt atgcaaggtg tatgccaact ttttttttt    27300 ctccacatct ttcagctttc tgatgggtaa aaattttcct tattttgctt tagaaaaatt    27360
ctcattggca tagatctaat ttcagggagc ctcccttgaa agctaaataa cattgagaat    27420
tcatgaaaat ataatgtaga gcattatgcc tgttagcata ttagtttaaa tagaagtggt    27480
tcatgaaaat ttttgaaatg ccagaccctg tcctgtgttt tgtattctcc caaatactca    27540
tccagatact gttcagaatg taacatgatt attttgaaat aaagattttc ccctagtttt    27600
```

```
taaaaaagtt actttataca ttaaccctta tgttcctctt tgatcaattt ttccagtagt    27660
gtaaacagtc ttcagggaag tagatttctt acagaaattg tcaagtggct ctctgctgtt    27720
agcatggtta ctaatctttt ggttacttt  catatttttt atactttctg gaagtggaca    27780
acttacttgt aaataaaagt gcataatttg tattaaaaat ttttagtaac aatctaattt    27840
gtaaaataga tgtgagcagc atgaatgtgt gtgatatgcg tacatacgaa ttatgtctct    27900
taaaaatgta tcacagacat ctttccgtgt ccaaacaaat ctacctcatt ctttctaata    27960
gccatatggg tataccataa tatatttaac taggcccta  ttaaaagaat tttgactctt    28020
ttgtagctac tatagtgttg cagtgtgtat ctgtgtatgt atctttgtgt gtgtatcttt    28080
gtacgagtgt acatatattt tccccttggc tatttcagat ttttttttag gtttaaatct    28140
taggaaaggt tttgaaattg tcttaagtat tttcagaagc attaaatcat ggttttttta    28200
catttttctt ttagaagttt tatgtcatct ctatgagtag ctttcagtaa tttgttctgc    28260
ataaaattcc cgaaaacttc catttaaaaa taggtggcat gactagactt tctcagccga    28320
aagagtgagg tcccaggaag gattttggag aagctgtgtt caaatatagc tgctgacctg    28380
atgtctgcct agagtctggc aaggtgatgt gttgaatcta gtgtctgcct gcatgccagc    28440
atccctttac tgatgagatt tgtggtttc  atcacttcat ggtaatcatc ccaagttata    28500
agatggagtc tctagaaaat cagtagagta tgaaggccca agtaaaatac atgtgagtgc    28560
atgtatgtgt gcatacaaat tacttctctt aaaaacgtat cctgggcatt taaagaatga    28620
ggacctccga aggattttgt ggaagctgtg ttcaagtaca gctgctgagc gtatgtcagc    28680
ctggagcctg gcaaggtgaa gtgttgaatc tagtgtcttt ttgactcact gtttttttg    28740 actcactgtg ctttgaagcc cttgtcattt gggctcataa aatagatttc tgtatactgt    28800
ctctcctccc tgccctcgcc cccatttaaa agtatagtgg cagaacccaa gaatcagagt    28860
tactaaaaac tctctagaaa atttggatga tcacccacct gatcatgtct tttttactca    28920
ctatgttttt tttttttttg agacagagtc tcgctctgtc gcccaggctg gagtgcagtg    28980
gcatgatctt ggctcactgc aagctccgcc tccctggttc acgccattct cctgcctcag    29040
cctcccatgt agctgggact acagggcctg ccaccgcgcc cggctaattt tttgtatttt    29100
tagtagagtc ggggtttcac tgtgttagcc aggatggtcc cgatctcctg acctcgtgat    29160
ccacccgcct cggcctccca aagtgctggg attacaggcg tgagccacca cacccggccc    29220
tttactcact atgttttaa  gcccttgttt tcatttgctc cactgtaaaa cattccccaa    29280
gccaatctgg agctgaggca aattttaac  aatttaaaat ctggggaata taaatattgg    29340
ataatgatca tcctgaaaaa acaatgaagg tagtagcata atactttata tatcaataaa    29400
atggcaaaat aagacagttg ttgaaggaca gaaagagtaa ctgaagttag gagcttatct    29460
taacacattt tttgtgtcat accataggca tcatattttt taatttttt  ttatttcata    29520 cacataggaa aatatatgtg tgtaagaaat aataaacacc tctttgtacc taccacccaa    29580
cttaaggaac agctcattgc tattcccttt ggtgctcgct ggatgccctt tcccagtcac    29640
atccccctcc cttcccatct gcaggactat actagtaaat tttgtatttt ttgcattatt    29700
ttgctttgtt ttatgatttt actacctatc tacatatccc taaataatac attatttagt    29760
ttcatatgtt ttaactttat gttgtggaat cacattaaat gtagtctttt ttttttatat    29820
tatactttaa gttctagggt acatgtgcac aacgtgcagg tttgttacgt aggtatacat    29880
gcgccatgtt ggtttgctgc acccatcaac tcgtcattta cactgggtat ttctcctaat    29940
```

```
gctatccctc ccctagcccc ccaccccccg ataaatgtag tctttataac ttgtttcttt    30000
aactcaacat tgtttgtaag attcatccat gtaagctgaa gcttttttat agagatcttt    30060
gttaagcctt ttaatgaata cagtacatac atttctctgt tccctgtta gtggacactt     30120 ggattgtttc cagagttttg ctgttttgaa caacgctgct gtgaaaatgt ctcctgaaac    30180
acatttataa gagttttttt ttccccaagg gaattatacc tagaaattga ataactagat    30240
cacaaggcat acacatctac aacttctgct aggtaatgcc aaattgtttc caaggagcgt    30300
tagaagtgtt ctcatcaact tttactagtg ctagtctttt acatttgtgg cagtatggtg    30360
ggtgtgaaat atttatgttt agttttctt ggtgccattt aataatttt ataaaaaata      30420 tttagaagtc aaggcagttt tttgttttg ttttattt ttgcttgttt tgttttaatg       30480
cagacattga gattacgact tggaataaac attggttgca aagttcctaa aaggaaaact    30540
ttttttggta ttctggagct tttctggtac tgaataaaat aagtatgtta aattatgcat    30600
gtgtagttta gaagtcagag caataattgt gattgttgaa cagaatggca gtaaaaagtt    30660
tctaaacgat tgtactgtac aagggacact tgttgtgggt cagttttagc ctccccaact    30720
tttatgttaa aagttgcaac aaggtttaag ggcttatgtt tgataggcca gatggtgacc    30780
agctgtgata aaacacaggg aaccccttgca aaggatttca aaatttatgc agtagtccgc   30840
cttatctgca gttttgcttt ccaaggtttc agttacccgc agtcaactgt gttctgaaaa    30900
tattaagtga aaaattacag aaataaagaa tcgaagagtt ttaaattta tgcttcccac     30960 ccatcccacc tgggatgtga atcattcctt tgttcagcat ctccatgctg taggtgctgc    31020
ctgcccctta gtcacttggt agccatccag gttatcagat tgactcttct agtattacaa    31080
cacttggctt caagtaatcc ttattttact tcatagtggc cccaaagtgc aggagtggtg    31140
atcctggcaa ttcagatatg tcaaagagaa gctgtaaatt gcttcccta agtgaaagat     31200 gaaaattcta gacttatata taagaaaag aaatcatatg ctgagactgc taagatctat     31260
gataagaatg aatcttttat acatgaaatt gtgaagaatg aaaagaaat gcgtgctggt     31320 tttgctgtca tatctcagac tgcaaaagtt tgcagccaat gtgtatgata agtgcttagt    31380 taaaggaaa aaggcattta aggtaagtat atatagtgtt tggtactacc tgtgatttca     31440
ggcatccatt gggggtctcc tgagtataag gggagactac tcttttagtg ttaaatgaac    31500
actaaggaac agagatgggg aagaggttgg agaagattag ttcagcagtt tgagtatagg    31560
taaacagttg tttgagaaag aagaaaaatg tgattagtat tttaccttag caatagtggc    31620
atagataatg ataaattata gtcacacaga actcttagta tttacagaac gttcacattt    31680
gtgatcccat ttaacaataa ctctgaaaga aaggtatcat ctaccactgc tttattgata    31740
aagatataaa aggtaagaga gatgaaacat attggccaat gatacccatc tggtaagaga    31800
cagggatggg gtgggacccc aaggctcttc tcgccaagcc cacggttttt ttgctttata    31860
cttttttgcc tcctgatcac catggctgca gtttctactg tggacaatgt ctgtcagcaa    31920
gcattgatcc cctgccttca gcactcttac gtcttagcaa ggactggaaa gaaaagcca    31980 ggagtttaca gtctgctgga gcaacagaaa agaatgatat gaaatatgaa gagaccaaaa    32040
tgatttataa taaggtgcta gactatgtag taaaaatctg ctttagctgt aagtcaaaag    32100
caagagcagt cttttcagaa tggaatagaa atgttggaat taaggaatt ttcaaagttg     32160 tgaattttt tcaagataaa catgttttat tttggtaatt atggtattac taatttgata    32220
accttcaggg agccacctaa tattatagaa gatgtacata taatgacaaa agcaaacatt    32280 ttattttaa ggaccacaat ctaatctaaa acaaaatttc ccccttttct ggtctttggt     32340
```

```
taattaagga cttatttaaa tatcaaagaa agacacatag aaaacattta gtatatttct    32400
atacttttat taatgtcctc cataccttac acagatactt gacttggcta tggtctagat    32460
aatccatgaa aatttaaagg acagatttta acaactttat gctaaattga tagatctcta    32520
ggatcagatt gccatcactc tcagatgcga agcttccaac cacttatagg ttcctgatat    32580
cttgctttta tacagaccta atttctcttc cttaaactt tcttttcctc agttgctatt     32640
tgattgaaat attgagtcat taaaaatttc caagtgggaa ttttttgtgtt tcttcatcta   32700 tcatgaagct gctcaaataa gtaggtgttt gaataggagt agaaacagta ataggctgaa    32760
gccagaccaa tacagcttca gctaaatgcc gaccttgcta aagtctggga ggaccggtgt    32820
ggtattctac aatgtacaag tctgtagccg gtgcccttaa tatgttggct tcatgtctca    32880
tgactctctt ctgtaaatat gcagtttaaa aaatacaagt tattctgctg tagaagatac    32940
atttgcaaaa ttgatgtatc ccctctaagt aaagttggct aaacaataag gacatattta   33000
taattaatga atttgagaag aatgctgacg atatgcatta ttctttgaag ttaacatttt    33060
tcaggtccta aataaacaaa aagtaggtta cttctgtctg gagtgtatgc aaggggtacc    33120
atcttgtcct tggttcctgg ctgctattcc aaggtgctat aaagtcagct aaagagagca    33180
atcataatac attgatagca tccctcaatg tgtttctgag ctacttgaga atcttatttt    33240
tgaataggta gcaggaaacc atctttgcag ggcagcatgg gcaagggat tggagggact    33300 attattataa agatccactg aactgcttca gtatcataat atcttaaact aaaggactgg    33360
aaagagccag attccaattt aatctgctct tctatgaatt cttagctggg ttcatttaaa    33420
aagaaaaaac ttgaagattg caagattttg aagacatctt aaaataggtg aactccaagg    33480
tgcactttaa acttgagact gataactgaa tactccttca ccttttgatc tgatattgtc    33540
aaaatgaatg aggacttagt gctctagtaa gtttggaaca gaatgatatt aatttatttt    33600
ctcatgattg attctttttt gcttttaat agattaaact tcaccgtaga acagtttctc     33660
aacctctgga ctattgacat ttttgattgg ataattcttt gctgtcaggg ctgttctgtg    33720
tgttgcagga tagttagcaa catccctgac aatcacaaat gttactttct gtctctatgg    33780
atttgcctat tctggacatt tcgtataaat agaatcatat atatgtggct tcttgtacct    33840
ggcttatttc acttaacatg ttttcaaggt tcatccatat tgtagcatgt aacagcactt    33900
cattttcttt ttatggctga gtaatattct gttatgtgga tatactacca tattttgtct    33960
atccactcct tagctgatgg tctttttaggt tgtgtccatt ctttggctat tataaataat   34020
gctgttaaga acattcatat acaagtttct gtgtagacat atatctttat ttctcttgtg    34080
tggataccta ggagtagaat tactggatca tatgataact ctatgtgtta ccttttgagg    34140
aactgccaaa catttttcta cagtggctgt atcattttac actcccatca gcaatgtata    34200
agaattccaa tttctctgtc cttgcctata tttattaact gtcttttctt attagccaac    34260
tgctgtggtt cgaatgtttg tcccctccaa aactcatgtt ggaacataat ccccaatgtg    34320
gcagtattga gatgtgaggc ctttaagaag tgcttgggtc atcagaggtc tgccctcatg    34380
aataggctaa tccattcatg agttaatgta ctaatgggtt atcactggat tgggactagt    34440
ggctttataa gaagaggaag agaactaatc tagtaagctc agccttctca ctatgtgatt    34500
gctgccctgt gtcaccttgg gactctgcag agagtcctcc agcagcaaga agttcttcat    34560
cagctgtggc cccttgacct tggacttccc agcctccaga aatgtaagaa atccatttct    34620 ttttttaat aaattacaca gtctcacgta ttcagttata ccaacagaac acagactaag     34680
```

```
acaccatcct attgggtatg ggtatctcat tgtgtttttt atttgtgtct cccaaatgac    34740
taacgatgtt gaacatcttt tcatctgctt tttggacatt tgtgtatttt ctttgaagaa    34800
atgtctttaa cattctttgc ccatttaaaa attaggttgt cttttattg ttgagttgtc     34860 ggtgtgtgtg tgtgtgtgtg tgtgtgtgtg tgtgtatcta aatatatgt gtatgtatat    34920 atgcagatat attctaaaca ctagacccct atgaaatata taatttgagg acaatttctc    34980
ccatttaaaa ggccatcttt tcacttcttg atagtgtcat ttgactcaca agttttaat    35040 ttttatgaag tccaatttat tttttaattc tttgttttg gcactgtatc tttaaaaagt     35100
tgcctgatct aaggtcaaac tgattttcac ctatgttttc atctaagaat tatagtttta    35160
gctcttacat ttaggccttt gatccatttt gaattaattt gtgtatatgg tgtgaagtag    35220
ggctctaact tattcttttg tgtaatgata cctagttgtc ccagcaccat tgttgaaaa     35280 gattattctt tccccattga atggtcttga taccttgttg aaatcaactg accataaata    35340
tataggctta ttcctggact cacaattcta tgagtctgta tgtctaatct tatgccagta    35400
ccacactgtt ttgattatta catctttgta caaagttttg aaattgggaa atgtgagtct    35460
tccaactttg ttcttttta agattacttt gcctatattc cgtgttcgtt gcaaactcat     35520
atgaatttta aatcaactct ccatttctgg aagaaaaaaa gaggcaattg aagttcagat    35580
agggattgca ttgaacctgt agatcagttt ggggaatatt gccatcataa caattagtag    35640
gtcttccaac ccatgaatac aagacttctt tccatttctg tagatattta gtttctttca    35700
ttaatatttt gtagtttca atataaaagt cttgtacttc gattaaattt attcttgaat     35760
attttgggtt ttgatgcttt tatgaatttg ttttcttaat ttcactttaa gattgttcat    35820
tgctactgat tagtaatgca actgatttt gtgtgttgat ttttgtatcc tgcaacctag     35880
ctgaaatcat tgattagcat aatagagtat ttaatagatt taggatttct atatataaga    35940
tcatgtcatc tgcaattaga gataattta cttcttccct ttcaatctgg acattttta     36000 cttctttttc ttgcctagtt gccctagcta gaacctccag tgcagtgttg aatagcagtg    36060
gtgagaatga gcatctttgt gttggtcttc atcttgtggg gaaacctttc agtttaagtg    36120
tgttgttgtg gggttttcat agttgtcctt tatcagattg agaatgttcc tttctgttcc    36180
tagtttgttg agtgttttct ttttgattgt tttaatcagg aaagggcatt agattttgtc    36240
aaatgctttt tctgcagcta ttgagatttt tgtgtgtttt tctggtcttt tatggtttat    36300
cacattaatt gattttcata tgtcaaacaa accctgtgtt cttgggtttc atctcacttg    36360
gttatggttt ataatccttt ttatatactt gtagattcag tttgccagta ttttgttgag    36420
gatgcttgca tttatattta taagggatat tggtctgttg tagctgacca gtaagtatag    36480
taagctgtat agtttactaa gtgttccctc tgttttgggg gagactttga gaagaaggat    36540
tgttggtaat tgttctttaa acatttggta aaattcacta gtgaagccat ctgggtctt     36600 ctttggaagt ttttttgatta ctaacttaat gtctttactt gtttgttata agtccattca    36660 gattttttc tccttgagtc attttttgaca gttggttgag gaatttgttc atttcatgta    36720
gttatctaat tggttagtgt ataattattc atagtattcc tttataatct tattttttg     36780 ctgtaaggtc agtcataatg ttcactcttt catttcggat tctggtaatt taagagtctt    36840
ctctcctttt ttttcttggt cagtctagct aaagtaaagt tttgtccgtt ttcagggaa     36900 cagcttttt tttttttttg aggcagaatt tccatcttgt cacccagtct agagtgcagt    36960
ggtgcaatct cggctcattg cagcctccgc ttcccgggtt caagagattc tcctgcctca    37020
gcttgccaag tagctgggat tacaagcgcc caccaccacg cctggctaat ttttatatt    37080
```

-continued

```
tttagtagag acggggtttc accatgttgg gcaggctggt ctcgaactcc tgacctcagg   37140
tgatctgcct gccttggcct cccaaagtgc tgggattaca ggtgtgagct accgtgccca   37200
acccagcttt ggttattttt gttgacctac tctattgttt ttctcttctc tatttcactt   37260
atttctacac tggtctttat tattttcttc cttatgcttg ctttggactt agttcttctt   37320
tttctagtct cttaaggtgg ataattaagt tcctgatttg aattcttact tctttgtaag   37380
gtggtcatgt actgctatga atttccttct cagaaatgta tatgctttca ctgcatccct   37440
taagatttgg tatgttgtat ttttgttttc atttgtctca aggtatagtc ttctgatttc   37500
cattgtgatt tcttccccct ctaacccgtt tattatttag gaacttgttg atttccacat   37560
acctgtgaac tttccagatt tccttctttg ttaattctca gtgtcattcc attctggtcc   37620
gagaacatac tttgtatgat ttctatcttt taaaatttat ttggcttgtc ttatgaccta   37680
atacattgtc tatcctggag gatgtttcat gtacacttga aagaatgtg tattctgctt   37740
ttgttgggta gagtgtttga caggtgtgtt ggtacatagt tctgttcaaa tctgtttcct   37800
tgcagatttc tatctagttg ttctgtctat tggaagtagg atattgaaat ctccaactaa   37860
tattgctgaa ttgtttattg ttttcttcag ttctgtcact ttttgcttta tatattttga   37920
aattctattg ttaggtacaa gtaagtttat gattattata tcttcttgat agattgattc   37980
ttttatcatt atacagtgcc ctataagaac aattttatc ttaagtctat ttgtctatat   38040
tagtatagcc acttcagctt tcttttgttt actgtttgca tggaatattt tcttctttta   38100
ctttctattt gtgttcttga gtctaaggtg aatctctgta gatagcaatt ggatctgcca   38160
atctttgctt tttatttggg gagtttaaac cattgacatt taatgtaatt attgatgagg   38220
aagattactc ctgatatttt gccatttgtt tcctttattt tgtgtctctt gttcttaaat   38280
tcttccatta ctaccttctt tcttttgtat tacatatttt ctagtgtaac gatttaatt   38340
tctttgtcat ttctttgtt gtatgttttt agttatttc ttagtggttg ccacggagat   38400
tttattgtca ttttaacagc ctaggttggg cacagtggct catgcctgta atcccagcac   38460
tttgggagac tgaggcagga ggatagcttg agtccaggag ttcaagacca gcctgggcaa   38520
cttactgaga tactgtctct acaaaaaat acaaaaatta gccaggcatg gtggtgtgtg   38580
cctgtagtcc cagatgcttg agaggctgag ttgggaggat agcttgagcc caggaggttg   38640
aggctgcagt gaactttgat cacaccactg cactccagcc tgggtaccag ggcaaaacta   38700
gcccaaagaa atgaaggaaa aaaaaatct aatttagatt aatatcaact caacttcaac   38760
agtgtataaa aactttgcct ctgtatacct cttctgcttc cactctgtgc tgttattgtc   38820
atagattttc atctttctac actgtgtgtt tatcaatgta gatttaaaaa tattgcttag   38880
tagttgtctt tagaatccga tacggagaaa aggagatata acaaaagat gcattttac   38940
tgtcttgtat gtttacttat gtaattccct ttcctgatgt tgtatttcta aaggcaaagt   39000
agggttattg tgagtgtcct tttgtttcaa cctgaaagac tccttttagc atgtgttgga   39060
gatatgctaa tgatggactc tcacagtttt tgttatctgg gaatgtgtta atttatcctt   39120
cattttgaa ggatagtgtt ggcaggatac agaattcttg gttgacatgt aattctttca   39180
gcattatgaa tatgtcatcg tactgtcttc tgacctccat ggtttctgat aaggaatcaa   39240
ctgttaatct tattgaggat cacttgtttg taatgacttg cttgtcgtgc tgctttcaag   39300
attcattctt tgcctttagc ttttggtagt ttgattgtga tgcatttagg tgtgtacttt   39360
attagtctgt tctacttgga gtttgttgag ctttgtagat gtatttcatc agatgtgtca   39420
```

```
agttcttttg ccactatttt ttttttaaat aatcttttg ccccttttccg ctccttctgt    39480 cactctgatt atttgtgtgt tgctttgttt ggtggtgtcc cagaagtctc tgagactctg    39540
tccagttttt tcctccccat tcttttttct ttcacttcct cagactggat gatctcaatt    39600
tgacctatct tcgagttcat ggatttctc ttctccaagt gacatctgtg agatgaattt     39660
ttttctagag aatttttcat ttcagttatt ctacttcaaa atttctcttt ggttcagttt    39720
tatcattgct atctttatat tattctcagt ttaatgagat actgttttat actttccttt    39780 agttcttttag acatagttta tgtcactgaa tatatttaaa atagctgatt ttaagtcttt   39840
ttttttttat tttttttggag atggagtctc gctctgtcac ccaggctgga gtgcagtggc   39900
acgatctcag ctcactgcaa gctccacctc ctgggttcac gcaatgattt taagtctttg    39960
tctatgaagt ctagtatctg ggcttcctca ggcatagttt ctgttttctt tctttctttt   40020
cctgtgtact tcgtttcttt gtataccttg taattgttgt tgttaactgg acattttgaa   40080
tattatagtg taacaactct ggcagtcaga ctgtctcccc tccccagtat ttgttgttgg    40140
tgagtattgt agatgtttgt ttagtgactt ttcatggcta attctgtaaa ttttatattc    40200
tttgaagatt gtgggcaccc tgaagtctct gtttgttagt ttagtggtca cctaataatt    40260
aacagagatt tcattaaatg cctagaagca aaatatcttc cagtctttgc ccatggcctc    40320
tgtgtatgca ttagggcagg ccttgaactc ttacccaggg agtttacaac cctgccttag    40380
cctttactac cagcttctgc agagcattaa ggtcaacagg tggtgagagt ttggagccta    40440
ctccatcttt cctgagcata tacacagccc tactcatgca tgtggccctc tagatttcca    40500
ggagtatgtt ggacccttc aaagccctta cagactcccc agcttttcct ctcaatcttt     40560
agactagtgt gttgttttct tcaacagtta tctgtcaggc agcagcaaat taagagatta    40620
gcataaatgt tttcaactcc tccacccgtc atgtgcccca gggaagcact aagccagttc    40680
taagttaggc aaaataaaga caatccttt gaggtggtct tccatggagt caccagacag     40740
gtaaaccaaa taattaatta caagtctttg gctggataca gtggctcaca cctgtaatcc    40800
cggcactttg ggaggctgag gcaggtggat cacaaggtca ggagattgag accatcctgg    40860
ctaacacggt gaaaccctgt ctctactaaa aaatacgaaa aaataggtgg ctgtggtggc    40920
gggcgcctgt agtcccagct actcgggagg ctgaggcagg agaatggaat gaacccagga    40980
ggtggagctt gccgtgagcc gagatcacac tactgcactc cagcctgggt gacagagcaa    41040
gactccgtct caacaaaaaa aaaaaaaaac aagtcttcat gaaagaggtc cattctgctg    41100
tctttcatac caggaatgtg gaatgtggac tgttattttc atggctactg ctaagctagg    41160
aatcaaggga tagatgggga ctgggtaaaa caccacagag tttgctgttc ttaccaagaa    41220
taagctgggg aagagggttg ttttttgtttt tcagtaaaaa ttccctgggc tgcttcaagc   41280
cgttgattaa ttttcaggtt ccgaaaaagt tcagtttgac agtttttgcc cttttttattt   41340 gcttttatgg atatgtagaa cttgagttct ttttttccacc agttttgctg acattgtttt   41400
aaaagcactt tttgtaaaac ccaaatgttg tctctctcaa ggctagccaa taattaaaaa    41460
tactgttact ccccttttgat tttggaaatg aattcgtatt gaccaaaatt caatactaga   41520
ggtctttcaa gctgttttac catttatcta aactttagaa tctaatgatt cctgtacatt    41580
gtctagcata ctggtggtcc tcaattgtca taagttcaac tttggaacaa atgaacttt     41640 tgtgtgcaag tttccaattg tttggaaatt acattgatgc cccctccatc aaactgttat    41700
tcgtgggaca tctaggaatt tcttacagca gctgacaaat atttcaagtc agtgcctggt    41760
agtactgtcc accaggcaac agcttcagta gtagagcgat ctttatctat aaggcagtgt    41820
```

```
ttgagcaatt gtttattagt gttttcctaa ctactcagaa gaactatcag gggttataga    41880
ggtagctcag agagttgggt gcaagtagag aaatccaccc ggcttgcatt acacatctta    41940
tttctagaga agctttcctt tgaagaagga gttctaaggt ttaaaaaatt accttgaatg    42000
ccacttatat tgcattttaa ttttatttta gagaaatcaa tggaaagtag aaaaattaag    42060
gcactgatac tagtgttaag aatgttggtt aaagcttctg gcaattaatt ttttatttcc    42120 tttttttaatt ttattaaaat ttaacaattt tcagtttatg ctgtaatcca gaccaaggtt    42180
tcaatctaat gaagttaatg ccagtgttgc tgctacctat tttgtcttta gtcattcagc     42240
catgcttcct acttatactg aataagctag cttaatctaa caatcaaaaa agaaagctgt    42300
tgcctaagtt aagaaaaaca gtttgaactg ttttcaaact aaatacccag tagactctct    42360
agttgttgac aggagaatgc ttaattcaga attgtcctgc agtagatcat tttatctcat    42420
tcctgttctt ctataggata gcttatttgt ttgaaattgt attaaatatg ttgtgatttt     42480
tgtgtgcttg tttctatttt tcactggata gactcaagat aaaacctggt accctgcagt    42540
gtagctatca gtttatagca gaggaaattt acattagaac ttggctgtgt atttacatgt    42600
atctaacttg gaggtcactc tgcttactgt tgatatatca gtcatattag atgagtccct    42660
aatgagatac cagaaacccc ggaaacatca ttaggtggaa cagtgtcctt aatgctttat    42720
taagtgttat aggtaagaca aagcctagta ctatttgtgg catcaaggtt aggtgtttaa    42780
agacctgtat tcttctattg tcatgttgaa attgttccct tgatgtagca atagaaaatt    42840
ttagattagg cttaagttaa tcagcaaaca aagataaaag tctgatacta tcctaaatat    42900
tttgtgtttc taaataattt aacagtgatc caattagcta ctcctgtaga aatgtaattg    42960
ataaactttt cactctcttt taaattgcca tcttgaattt tacctgtttt ttaaagctgt    43020
ctcaagtcct ctctaaaaaa aggcagtcat ttataaattt agaaaagctt gatagcacag    43080
aaagtcacag aaaaatgtaa acatagttta aaactgaatt gtatacaagc cactagaagt    43140
acttttatta agtttacaaa tattagtaga gtggaactca tgcatttaat atgtttgaaa    43200
cttttgatca aatactgtgc tatgaaaaac attttagata attattcttt aatcatgtgt    43260
gtgtaaaatg tggctttttt tgacaaccaa gtagcttttc tgtgtgccaa actgtgactt    43320
taaaatttta aagtactcaa cagagtaaac aaaccacaaa taccacttaa actgtacaca    43380
tttgcacatg catttcctat aaatagtaca tgggtttcaa gtcttcactt tgaaattca     43440 gaaatggggtt ttttctcctt ccagtagaaa taaaaacttg atttatttta tttatttatt    43500 tattttatttt ttgagacgga gtctcgttct gtggcccagg ctatggtgca ggagggtgat    43560
ctcagctcac tgcaacctct gcctcctggg ttcaagtgat tctcctgcct cagcctgccg    43620
agtagctggg attacaggtg cctgccacca tgcccagcta attttgtat ttttagtaga    43680 gatgggtttt ctccatgttg ggcaggctgg tctcgaactc ctggcctcag gtgatctgtc    43740
tgtctcagcc ttccaaagtg ctggggatta caggtgtgag ccaccgcatc cagctaaaaa    43800 cttgatttttt aaaaatccaa atcgaagaca gaattgtgta ttttagtaca tttattagca    43860
gccttgacgc tataccatat ggctgtttat catttaaaca gcttgtaaaa gcaaacactt    43920
caggattcat gagtggcaga aggactgagt actttgggaa ataagagaga acttttgttg    43980
aggatggttg aggaagagtc caagacaata ataggcagaa taagcaaaaa tctagagact    44040
cattgtaggc actcaagtat gtatttgtta gaatgaatgg ctgaacttgg tatattgagg    44100
aacactgaga aagccatact gactggaaga tagttcctac aagaaactgg tgagacatat    44160
```

```
gttacagtct agattttggt gagccttgtt aaagtttggg ctttattttt atacggggag    44220
aaagtttcac agggGtttgg aaatgaggct tggagctgtt aatggggaca cagtgaggtt    44280
ttagggtagt ggctttcaaa ctgtttaaat ccaaactttg atgataaccc tgacataact    44340
attgtttata acttccattt cagttgtatt ggttttatca aacatcttc attgatctta    44400 ctgattgctt cctatgcaga ttaatattat aaatttgaat gtacaaagga agctttagca    44460
gtaaaatagc aacttttatc tgtcttacgt attggaggtt ctgcataaga tttaattttt    44520
tttttttttg aaatggagtt ttgctcttgt tcacggggct ggagtgcaat ggtgtgatct    44580
cggctcacca caacctctgc ctcccgggtt taagtgattc tcctggctca gcctcccaag    44640
tagctgggat tacaggcatg tgccaccatg cccggctaat tttgaatttt agtagagacg    44700
gggtttctcc atgttggtca ggctggtctc gaactcctga cctcaggtga tccgcctgcc    44760
tcagcctccc aaagtgctgg gattacaggc gtgagccacc gcgcccggcc aagatttaat    44820
tttttaaaag aaaatatttt gctaagggtt tggaaactct tgttttagca agaatggatt    44880
aagactgatt aaaactaaag gcaaagagga ggctcttatg tttggaattc tttgctaata    44940
tttacacaat ataattctct ccacaaatat ttaatggtac cagatattag atggttataa    45000
tggcaaaagt gttcaaagga tgctatcata ttcatgattc atgatcaaaa tgaacattat    45060
aaggctatcc ctcttcagaa ttaaatacgt tactcctgtg gaaaacttgc ttttaatgta    45120
gaagttgtcc cagagccttt cttcctttct catgtcctct tatgtccact gctgagctaa    45180
catgggtctc actgaatgat taagaaaaaa catcttaggt ggggagttct gtatatagta    45240
aatgtttaat ttattggggt ggtgaacggg aagtgctgct ggcaagagag gatgggaaga    45300
gaaatctacc caaatcctta cccgctttac agaacataaa cttcctattc agtagtacac    45360
aataacttaa cgatcaaggc atcttaactt ttctgttttc agatgaaaga actatcgttt    45420
ggcttgatca agtatttagt atttattcgt tcactcaagt gcttacgttt ttttgttatc    45480
tcagggtttt acgttagtta ttaaccaaaa gaactagttt tagttctgga agtctaaaat    45540
atataagaga aggtgaggag taataagaga agatgaaggg agactttcgg aatggcctat    45600
gaacttctag taactatacc accttaaaat agacaaatta caatgcagtt atgaagatat    45660 gtattttttca gtgaagacaa ctaaaatgtt tgcacagaat tttcttttttt attgagtgtt    45720 agaaattcta ttttggagat actaccttgc acaacataaa agaaaaagt gagtgtggaa    45780 tctaggaatc tacgtggctc taggaaattt tttaagtgtg gaaactgaag gagagcaaga    45840
gaaagggagc atggcattcc cctgtttgta gttcatgagg tgggtttaaa ttgccttttg    45900
ccaatgcagc tgcacactga ggattacaga attctttta aatgtttgta gaattatttt    45960
tcacttatta ggtaaaacgt gtattttttg attttctcca atttcagctt tctcatgttg    46020
ctatgctcaa ttttgtatac catatatagt tttgttaaat tgacaaagtg gtgtttttttg    46080 ttcttctttt tcccattggt taaaatttaa agagaaagtg gaagctagaa atttatctaa    46140
aaaatgtaac tttccctgta attattaaag tatcaatcta aatttgaatt ttctttgtgc    46200
ataatctttt ttcaagctat ttaccatgtt gacaaacttg ctttcctgtg gcaaatacac    46260
tagcaatacg ttataaatat gtaactttca acctatttac agttgatgct ttttagccc    46320 tttggattta aaatacaagc actgaagagg tgaggaagta ccactgctgc ctcagcatta    46380
tttcgaaatt ctgttttataa actatacaat ttccaaggtc atgaatccag cacctttcca    46440
ggtactaact attgggacaa agatagaatt tgattttatt tatttaccta ttgactgaag    46500
tctaacttaa atcttgcacc tagtaagatc ttagaaataa cgtgtgtact ctgacctgta    46560
```

```
aactaatcct agtattctgt gtgtatattc tttctcattt gggctcttaa aaggaaaagt    46620
aacgtacatc tgatgatcat tagcactgag cttttttcagc aaaaagtata tgtttataaa    46680
gaagtatagg ataatttagt aatttaataa tgtgacaaca tttgcgtgtg tttttttttt    46740
tgagaaatac aaattgtgag aaacagaaaa gtaaagaag cagcagcaga aatatcacta    46800
taggatcaaa agattgcagg aaccaaaact ccaaaattat tgggcataat gtactaaaaa    46860
cagggcagtg gaggaaaggg acagtccaga ctagctctga gggtccaaag aaagtattaa    46920
atattgttac tggagtgatt tgctctgcta tttgggcttg ggaattaagt gaaattgttg    46980
atatactaga cagatacttc ccacccattt ttctcttgat aatcaggggtt catttttct    47040 attttctatt tctctggatg ctccatttct taatattaat attaatatta agctctcagt    47100
ctttatgcta aaaattggtt atttaaaaca atttaaatca acttcagtct aattggctta    47160
agttcaaatc catttttaaga tcgatattgt gtcctttaaa aattttattt aaagatatt    47220 taaactgatg agaggatact acccattcca ctgataaact attactgtaa gtttgtctat    47280
tgagggctag ttatttggtt taaaaatgct gagattatgg aaagtggatt ggaatatttt    47340
ggagcaatat taaaaacagt atctgtaaca atttaataaa cttataaatt cctctttctc    47400
tgttgatcta tcttgaaaag acactctatg tctctaggca ttccttctct gtggtgtgat    47460
tggtagacag ggagtaaaca acttactgta aatgggcacc atgccagttg gcttcaggca    47520
gcatcaagct tgtgactcac agtcagggtt aggaaaatgc cttttaactt gtttgtctct    47580
gcctctttta aacattaaag gcacaactgt actaattatt aagtatttca taaggtcttt    47640
tagggcttat aagatctttt aggaatggcc tggaagttat tagtactgtt tcattgaatc    47700 tgaataccctt taacatgata atgagaagtt tttaaagggt ggttttatag ttaaacggaa    47760
tttctcaaat tggcttgctc cttatgttga tttatttagg atcacatttg ggagtttctc    47820
tgccctactt tcaatgtatt taatttactg accatcacta tttgggggga aaatgttata    47880
tgatatttag aaaccaagag ttttggagtt tttccccat tagatgtatt tatttattta    47940
tttattattt tttaaagaca gggtcttgct ctgtcaccca ggctggagca cagtggcatg    48000
atcctagctc actgtattct tgaactcctg ggctcagact gtcctcccac ctcagcccaa    48060
gtggctaagt atcaagtaag aatcacctgg caaattccaa ggctgtatac cagatttcct    48120
aaattagaat tttggggttg ggtatctgaa ttttagtaaa gccctccaaa tgtttctggt    48180
attgcttcta agaacaattg ataacataat agctgtggcc attatagggg tattctgtca    48240
tatttagata taagcatacc ttgttttatt gtacttccca aatattgcgt gtttattttg    48300
ttttgtttca cttacaaatt gaaggtttgt ggcaacccta tattaagcga gtctgtcagt    48360
gccatttttc caacagcttg tgctcatttt tgtgtctctgt gtcacatttt ggtaattctc    48420
tcaatatatc aaacttttc atcatttttg tatctgttac gaccagtgat cagtgatctt    48480
tgattttttc tttttttttt ttttttgag acggactttt gctctgtcac ccaggctgga    48540
gtgcagtggt tcaatcttgg ctcacagcaa cctctgcctc ccaggttcaa gcaatcctcc    48600
tgcctcagcc tccccagtag ccgggcctac aggcgtgtgc caccacgcct ggctaatttt    48660
tgtattttta gtagagatgg ggattcccca tgttggccag gctggtctcg aactcctgac    48720
ctcaggtgat ccgctcacct tggcctccca aagtgctggg attaccgtgc cagcctgatg    48780
ttactatttt aattgtttc aggcaccata aacctcacct gtataaggca ccgtacttaa    48840
ttgataaata ttgcgcatga tctgactgct cttccaactg gccattccct gtctgtctcc    48900
```

```
ctcttcctgg gactctcaaa tccctgagag acaataatat taaaattaag ctaattaata    48960
accctacagt ggcctctaag tgttgaagtg aaagagttgc atgtctctca ctttaaataa    49020
aaagctagaa gtggctaaac ttagtgagga aggcacatca aaagccaaga caggccaaaa    49080
gcaaggactc ttgtactaaa cagctaaatt gtgaatgcaa aggaaaagct cttgaaggaa    49140
ataactagtg ctactccagc aaacatgtga atgatcagaa agtgaaacag ccttcttgct    49200
gatacgaaga aagtttttagt ggtctggaca gaagatcaaa ccattcacaa cattcccttta  49260 agccaaagct taactctctt caattctatg aaggctgtga gaggtgagaa agctgcagaa    49320
gaaaaattgg aagctagcag aggtcggttg atgaggttta gggaaagaag ccagcgctgt    49380
aacataaaag tgtaaggtga agcagcaagt gctgatacag aaactgcagc aagttatgta    49440
gaagatctag ctaagattac taaataatag attttccatg tagatgaaaa agccttttgt    49500
tggaagaaga tgccatctag gactttcata gctagaaagg agtcaatgtc tggcttcaga    49560
ggacaggctg acattcttgt tagggctaa tgtagttggt gactttaagt tgaagccagg    49620
tctcatttac cactccaaaa atccgaagac ccttaagact tatgcttaat ctactctgct    49680
tgtactctag aaatgaaaca acaaagcctg gatgacagca catctgttta tagtatgctt    49740
cactgaatat tttaaggcca ctgtaaagac ctgttcaact gctcagaaaa aaatgattac    49800
tttcaaaata ttgctgttca ttgacagtgc acctgggctc acccaagagc tctaatggaa    49860
ttgtacaaca agatggatgt tgttctcatg cctgccaaca catcatccat ttgtagccca    49920
tgaatcaggg agtgatttca agtttcaaat cagtacattt tgtaaggcta tagctgctat    49980
agacagtgat tgctctggtg gacctgggca agtaaatca aaaaccttct gaaaaggatt    50040
ggccattcta gatgctatta agaatttgtg attcgcagga ggaggtcaaa ggatcaacat    50100
tagtagcagt ttgaaagaag ttgattccaa cagttataga tgaatttgag gggttcaaca    50160
cttcagttta ggaagtcact gcagatgtgg tagaaacagc aagagaacta gaattagaag    50220
tggagcccga aaatgtgacg gaattgctgc aatctcatga gaaaacgtga atggatgagg    50280
agttgcttct tatggacaaa tgagcaaata aattttttttc ttgagatgga atctactcct    50340
ggtgaagatt ctgtgaacct tgttgaaata acaacaaagg atttagagta ttacataaac    50400
ttaattggta aagcagcagc atggtttgag tggattcatt ccagttttga aagagtttct    50460
actgtgggta aaatgctatc aaacagcatc tcgtgctaca aagaaatctt ttatgaaaag    50520
aaaagtgaaa cttcattgtt gtctactta agaaattgcc acagccaccc caccttcagc    50580
aaccacctct ctgatcagtc agcaggcatc aacactgaag caagaccctc cacaaggaaa    50640
aagattacaa ctcactgaaa gttcaaatga ttgttagcat ttttaagcaa tattttaaga    50700
ttaaggtaaa tacatttttta aagacacaat gctattgcac acttaataga ctacagtata   50760
gtataaatat aacttttata tgtagtggga aaccaaaaaa ttcgtctgac ttgctttgtt    50820
gcaatattca ctttattgtg gtctagaacc gaacctgaaa tatctcagag gtatgcctgt    50880
attaatatta ttttgcaagt aaaaaaccca gcatataaaa aaaacgtaga atatgttgag    50940
agttcagtaa tatggatgaa aatgttttttc tctaactgaa gaacatgata aattataatt    51000
agggaaggat ataaccaag aaaatatgtc tgagatagcc aattcttgca gttcataata    51060
tgaaaactca ttataccaat ctcagtaaga atacttttaa tagctgttat ttctttggga    51120
tatagaattt ataaagtaca cagtaatctt cttatgatca atcctaggat cactttacaa    51180
ccacttaccc catattacaa tgtagtacca agacaagcag accaaattat agaaggacaa    51240 agttttttgct aagcatattt tgtcatcagc ataccgcatt gtgtgtgcat gcatgtgtgt   51300
```

```
gtttgtgcat gtgtgtgatt gtataaaata ttagaaagcc accccagaaa agttaaatga    51360
ctaggaatgt tgtgaaggga ttaagctacc cctaaaatta tataacaaaa ctctcttcat    51420
ctattattag gtcatcttta gaacatcttc tcttaaattt gttataggtc tctctcatct    51480
gtttggatta aaattggtct gaaagcctaa aatggctttt tacctatata attatttccc    51540
aactagcttg tagtataggt gcaaagctat cacacttgct aggttagtga agtatgtaaa    51600
aactaccatc tttcaattag gaaccatcgg atagcttcta caggattgct ggggagaacc    51660
tttataaaga aagttatatc tttataaatt ttttgtcatt ttacttagct gagaatataa    51720
aataagttag ctaataatag agtagaaatg ttttctgtaa cagattaata ttgatcaaat    51780
gtgttattaa atgctaaaac accattttt ttctctgtaa gccatgtgtt tcatgccaca    51840
acacaaaagg gacaattgtc tgtgttttat gacagttctg ttctgtcaga tgctgtttgt    51900
tcattttggt gaataaatga agagagccct ggacacatct ttttttcctc aacaaaagag    51960
gaaaattatt cttgtctgta tgtctataat cctgactctt tgaatggctt taatttttt    52020 aaagtcagca ttttttata aagataggtg tttggaatgt gggcgatatg gctggacagt    52080
tagattggga ccaaataatg gaaggctttg aacatcatgc taagaggttt gggttttact    52140
ctgaaggcag tagagaacca ttatgttttt aagccaggat tgacttgttc taagctgtac    52200
cttagaaata ttactctggc agttgtacat aggatgagct gtatgttgct ttgttttgtt    52260
tggggagaca gttctcgaag agagactaca tacgaaggca gttatatgag tcattactaa    52320
aggtctggca agaagtagta aaagcattaa ctggagtggt agcagtaggg aaggaaataa    52380
aaggatagat gtgggagtca tttggaaagt atgaggcaat tcattgacct tacagaatca    52440
ctggttttct gcttccactc cattcacatt gacctttcca aggttatcag tgacctgctt    52500
gtccttaaat tcagtgggca ctttccagta acctactgtt ggcaccagcc ctgtgctaga    52560
caccaggatc ctgtttgtaa aggcatctgc cagtggtttc tgtgacacaa ttctgtttct    52620
agttttcctc cttctacttc tctagcctct tggcaagttc ttctttcaga gtttctcaga    52680
gctttgtgct aggccctctt ctcatttct ccttctctaa gtgatcccat ccttttctgt    52740
tgcttcagtt accatttgtc cttatgcaaa ggacagccat atctactgta tctccagctc    52800
agatgtatct ctttgcctcc tgacccatat ttccaactat ctaactgggt atcttttctt    52860
ggatgagtta taggtctctc aaacacaaca tgtccagaat aattcattga cttattctaa    52920
ggcctgcttc ctcttctcc tgtagtccct atctcaggaa atatatggtg ctatcaaccc    52980
caaagcagaa atctggacat aatccctaac taccctttc ccctctctgt gcacataatt    53040
tcagtcatta ggcctcatag attggactaa ataaatacct cgcaaaccct tctacttata    53100
ttcttaactg ctcctacctt aagccaggct accataattt tgtagctgga tgactgcatc    53160
atcatcttga ctggctccct tgtcatcttc aatctatatt ctatactgca gctagagctt    53220
tcaaacataa acatgtgatc agattagtcc cctctttaga acaccctagg gttctcactg    53280
tcctgagtac agtctaaggg tttaccatgg cttacagggt cttttatgat tggtgagct    53340 ttttattgta taacctttct aaactgcctt tacttccctc tttcttggct ctgtgtcttt    53400
gcataatgct gttccctata cttcacctca cgtctaacct tcatctcctt tcacttctc    53460 ctcttcctcc aaaatccagc tgaatatcac attgtcatgc aggcccattc ttgatctccc    53520
acgtttgggt tagatatccc tcttcagtac catcaccgca ccaggtgtgt cccctatcct    53580
agcatttgcc tcattgtatt acaactactg tgtactcgtc tctacagctc ctgctagtct    53640
```

```
aaaagttttg ggagagcaaa ggttcatgtt tgtgtttttc actgtggtat accccagtgc    53700
ctagtatatg ataagctctc aaaatatttg ttagatgtat gaagaaatga aaagagaac    53760 aggaagaggg taagtttcaa gactaggaaa caaggctatg aaagctgcag gaaagcagca    53820
ggttaaaacc tagaagaaga gtttgtttta ggaaatactg tgttttaaac cactataact    53880
gaagcaaaaa cccaaggcct gggtgtggat agagtccact atctgataac agtggatact    53940
gatgcatggc agagttggag aggaagagag ccagattcca aaacagaagg ggtaaagtct    54000
tctaagaaga tagattatag taagaaggat taggggatag aaatatgagc ctgttccact    54060
catagatctc aaacatgaaa tgatgagtca tcatgaagag agtaggcaat tgtccagtga    54120
agaaggggat gctaacccct cttaaccttg aatctctcag gtagaagcag ttagagaagg    54180
aacagccatc atcagatagt gttgtaagga aaatgatatc cttggggaaa cctgcattt    54240 ggtaaagcaa agcaactaag aaagaatata ctaccactgt ttaacaatcg ccacaaaaag    54300
acagtaggat catctttgac cccctcatc ctttctcagg aacttggagg actaagaaga    54360
gagaaatctg tagaagaggc ttctctctct gatcctccct ccacttcagt tttaccacat    54420
gtaatgcaac aataattaag aatttgtgta aaatttcacc aggttggcat gcatggagag    54480
aaaaattatt cagatgtttt cctttgtcaa taatacaagg agcatttgta gggaaaaata    54540
tttacaaata cagtaagacc tattctcttt ctatatttat gggaaaattt taagttgtgc    54600
ccttgtttca tgtgtgtttc tatttaaaga taccatactt aatatatatt gttgattcat    54660
taacattgaa ctcatggcta acagcactat aaatcatgtc tgatcaaaac ttatgataca    54720
tgtactttct tcgtaaggta catcatagtc ttctcgtaca tgggaactct aggtagtact    54780
tcaggactat gcatagaggc catttttaaac agcaaaattc ccaacaaaaa gcacaaaact    54840
caaaaaatgt gccactaaat ttaccatgaa aaggacactt gtttacagtt tgagagctaa    54900
aacaagaagg tggcgtgtca cttcgtttga cttcagctgg gaacatgcat atcagtcgac    54960
tcaaattttt tgctattctg tgcttatcca cgaatcgata ggaaagcaag tgtggatttg    55020
ggggttacaa ataaaatgta gcaaatgtgt aaacttgcag atgtggaatc tacaagtagt    55080
tagaatcaac tatgttagtc tgatcattaa atcagttttt taaagtacta ttgtaacacc    55140
ttataacctg ccccattcac tgagtgttgt agtttatagt ttcattgggc attttcagta    55200
gttttatctg aagtcacatt tcaaattttg taattgaagc tccaaagtat gctaccggaa    55260
acacgagctg atgctgtgag acaaaatcaa caggtaatcc accatcacaa ctgtgggcta    55320
gaatgctcaa gaaaccttgg aggcccagag agctgagatg aatactgaag aatcataggc    55380
aggtttactc tgtcaagctg cctgtatttt gagggtgtag tcctcaaacc aaaaagacac    55440
caaatgaaca aactcagatg gcctcactgg ggaacagaga ttgaaagctg acactggaat    55500
gtgtacttaa aaaatgaga gcccgttttg gaaaggcaga ctgggcacag aatgtggaga    55560
gctatatttg ctaactgaag aaatttagac tttatcctct acaaacaaa gctattggtt    55620 tttgaaggtt gcataaaagc tgcatttag cagcatatat tttggtagag ctgttacctg    55680
cctgaaaaca tcaatgtcat ttcacacaaa tgatacttat cccttggtgt ttgatctaaa    55740
tttctacaat gagaatgtga ttttatagtc tttactgggg aaggaagtag gttttcagg    55800 ccgaaattct tgtgtagcaa aaattaacac ttaagttagc ccttggcaat ctccagttct    55860
ataatggtaa aatggatttc ccagaaagtc actctctatc cctttgaata gacattagaa    55920
ataacatgta ctttaagtgg gatttacaga ggaaggggc cttaattct ttactagtgt    55980 gatgccctgt aaaaaaataa ctaacattag agttgaggcc tagaaatagc agcactgggt    56040
```

```
taaagtctgt tttcaagtgc aagttttttct ttttattcgt gtgtgtgtgt gtctgtgtgt   56100
gtttcacata gaaggaggaa atgccaattt cagttcttac aaatattaat gactgcaact   56160
tataaaaatg ttacagacta tattcttccc ttttgtaaca gatgagaaga ttttgaaatt   56220
tagtctctac tttttagttt ggtaagacaa tttgaataaa ctgcaataat tgcaaaagaa   56280
ttctgaatat ttgaacattt gacattttct atgtcaaata tacatttctt gtactatata   56340
aacattctag aaaagagaga caggcaggga ggaaagtgct cattaaaaag agcttcaccc   56400
tctctgaaaa gggatttcct ttacagtgct gtgtactaaa gcctgtgttg taaatcagaa   56460
agcactgagc acacatgttg ctgctttggt agcatcagaa gtcgattttc attagcctta   56520
taccattcac tatttctgcc aagcaatctt aaattataaa agaatcttat ttgattttgt   56580
gattctcttg ttttctgctc ataaagaaaa tatcctaaat tgaacaatgg catgctacgt   56640
ttttagtttt taagacagct aatgtgtaaa aagacattta agtatagtt gtgttaagtt   56700
tttgaagttt acagttgttt caattttgct gctatacttt gttaacatat tttaggaata   56760
tttcatttta gtcacaacta ggatataaac attattttgg tggcgatctc cttgtaatca   56820
cgacgtcaac caaatttggg aaattttgat ttgttagatt tataaatttt acagtaacac   56880
aaaagtctaa tttcctatat attttcaagg cccctatacc tttgtcaaaa taaagtatca   56940
atgaaaaatg aaaaaatcat aaactatgtt caggccaaac tgatactgac tttgttaaaa   57000
ggctagatag aaatctgttt tcctcttctg ttacatctcc tcttctggag accactctgt   57060
gtggactgaa ggtttgagat cctaggacct aggctagaac agattaggag attgtgctgt   57120
atgttaagtg gcagatacca tggaattcta agcctgttac gaaggaggag aagaagaggc   57180
acaatgaccc tgacacagcc cctgggttga ccacagcaga tatctcactt gagcaagtag   57240
atatcatctc aattgcttgc tgattatctc taacttgtca gtaacttact ttgataacct   57300
agatttagga gtctgacagc atgcagtgta tgcctcataa taatctgctg tttatgaaag   57360
tcataacatt gtatgtttag cataatggtg aagagcctgc catctggaat ggtctactta   57420
tttgggatcc acatacagta agctctcact taacatcatc agtaggttct tggaaactgt   57480
gaccttaagc aaaacaacct ctaatgaaac caattttacc acaggctaat tgatataaac   57540
aagagttaag ttcctgtggc atatttctgg tcacaaaaac atcactaaac ttctaaataa   57600
agacccaaaa cacttataat attaaccact gaaataaatg tgagctatat atatacattt   57660
aagaataata aaaacaaaaa ataattattt acccaatttt tggtgaacca gtgagtgata   57720
gtgatcatag tgatggtgga tgaaatcaag gaataaatat ttgcaaagtg aaaattgtaa   57780
gaagcacccc ctgtcaccac atagctcaga aataataatt agggcaggct tgctgagcat   57840
ttttaaactg cactgtttat tgtcatgcat ttgaatgatt atcgcagact ttatgaattt   57900
tcattttata ttaatttgta ggccaggcac agtggctcac gtctgtaatc ccggcacttt   57960
gggaggccaa ggcaggcggg tcactggagg tcaggagttc aacaccagcc tgaccaacat   58020
ggggaatccc catctctact aaaaatacaa aaattagcca ggtgtggtgg tacacacctg   58080
taatcccagc tatttgggag gctgaggcag gagaattgct tgaacctggg aggtggaggt   58140
tgcagtaagc cgagattgtg cccctgcact ccggcctggt gacagagcta gactctgtct   58200
caaaaaacaa taataataat ttgtattcat tcattttcca atgtgttcat tccagttcag   58260
ggtccagggg gcctgcagct tatactcata gctcagagca actgaccccta tagacaggac   58320
gccacccat tgtagggtgc actcaaatgc acactcacac tcaaactggg acccttcaga   58380
```

-continued

```
catgccagtt accgtatcac acacagcttc gggatgtggg aggaaagcga agtatctgga   58440
gaaaaactac acagacatgg gaagaacgag ccaactctac acagacagtg gccctggaca   58500
gagctgggca ggcatcagtt ttttttcttt tttttgtggg gggtgagggt ggggcatgga   58560
gtctcactct gtcacccagg ctggattgca gtgcagtggt gtgatctcag ctcactacaa   58620
cctccacctc ccgggttcaa gagtttctcc tgcctcagcc tcccaagtag ctgggattac   58680
aggcgcccgc caccacacct ggctaatttt tgtatttttta gtagagacaa ggtttcacca   58740
tgttggccaa gctggtctgg aactcctgac ctcaggtgat ccacccgcct tggcctccca   58800
aagtgatggg attacaggcg tgagctaccg cgcccagtca gcatcatttt ttttttctca   58860
tcaacgttaa aacaatgttg aacaaaacat tattcaaaga cctgccgtat ggctattttc   58920
tagttgtgtg actttctttg ggaaagttag caacccttc tgagcttaaa tgtcctcatt   58980
cataaaatgg ggctagtaat aatgcataag gttttgtaa gaattagaat taataaagta   59040
cttagaccat aataactaat tagtattagt tgttgtcttt gctattattt tgatgtggtg   59100
gttgtttggt ttcacctgtg tactatcagg acatgctgaa ataaaattta gaattggct   59160 ttataatatt agaaaagcaa acttttgtac gatatgggta tgaaaaattg ttgggagtct   59220 acttttctc tcttacctaa tttgtcttag tcttttttaaa gcttagattt tccaaatgag   59280
ccatagcaaa atataatgtt taaaaatgtt taaattctaa gcactatgtc atagttaaat   59340
aacttaaagg tgctacatct tatacagtcc aaaaggaaca taattagtaa aattctacaa   59400 tttagaaaaaaa aaatagctg acagtgactg atttataaaa gtaaaatatc ttttgttaat   59460
actaatattc tttttataaa ttaattgatg acaaaaaatt gagtgaatga gatttgcagt   59520
tcatttatct atgatgctgg tttatttaat ctctataatt tgctgtattt gaaagagcat   59580
agtgatagag gtcatgataa aatctaggcc cagtgccaca actaaatccc tgtaggaact   59640
ctcaaggttt tgatttcatc tctgaatggg aataacacct tccaagaata ttatgaagat   59700
taaaaagtta cgtatcataa atacacacag agtaacaata ctgggaatat tgcaacttgt   59760
aagaaagagg aagcatatgg catattctga tggttaggga tatggactct gtagctggga   59820
tgcctgaaag agaactctga ctccactaat ggctagttat atgaaattgt gcagataatt   59880
taacttctct gagtttgcat ttttctttgt ctatataatg gggataataa tagtacctac   59940
ctcacacata gtgttaattt ctattagtgg ttctcattaa gatagtattg ttgttcatcc   60000
ctggttgtta gccatcatgt atctgagtta gagagtcatt gattttagaa agtcccgagg   60060
agactatcag gtcaagcaac ctgcctcctg ctagacaatt agctttatcc atgagttacc   60120
aaagagggag ccgaaaccca gggaagctga aagagctgtt gattgtcacc ctgtgagttg   60180
gtgatagaaa gatatctgga atcccagtag ttgcccattt cctagttctg ggctctgcat   60240
tgcactagaa tactgtgcca ttctaaatat gaaaaggcag tatgaccatt gtgcttgtca   60300
cttcccattc cctagatgct atcttatatt tgtccttatg aaatttaacc tgtgactttc   60360
agatcactta gaaccttggt tggacagtgt tttctagtgt tatttagtat attttttgt   60420 catcttctgt tgtctttggg ttcccctaaa agagctatac tctgggtgcc aggaaacttc   60480
acacatgact gtcttctctt cctcgacttc cctctctact taccttcca gctcgtagca   60540 aatcagaaga cttctctgac acctctctat gtctaaaggt cctttgatat tctcacatgg   60600
cggcatgaat cacagtgtat tttaactggc cttttccttg tatgtctcct acaatgagct   60660
gttgaagctt catgaaaaca caatctgttt tactcagggc agttataatt ccaattacaa   60720
agcacatttc ctggctcctg gctaggaact cgatcatttt tcgatgcttc cttgctcagg   60780
```

```
actttctgat tccttcttaa aacatttttgg ggcatctcct tctcctggtt tttggaaaca  60840
tattctcata ctgctatgaa ggtttttact gacatttcca acttctctta aattgattca  60900
gcaaatgttt ttccataata aatgtcattg atatgtcatc aatatggaga gcaacaacag  60960
aatgcattga gtaaactcct cccctggagg tctgagaatc tagattccag ttctcacaga  61020
gccaccacct tggtgacctt ggacagtaga ccttctaagc ctcagtttcc ttatcccta   61080
agtggggata ttaatagaac ccattctcag agatgttgcc aagattaaaa taaccaagat  61140
aattcctgta gatgatttgg catagtgcct gccacgtact aagcaagagt tagcctccgt  61200
cattatagta tgatcataaa aaatgaacag actaaacgaa gtaaccagaa ggaaagaaat  61260
tttaattctt aaaatgtaat agtttcttgg ttttttttt tctgtgaaac acctgcatgg   61320
cacctttttg ttattcatac tgttttgact gtggctgtcg tagattcttg ttgaaagtct  61380
gagagactga gacttgtcat tttgaacatg gcatcagtgg aacagcttat gattcaataa  61440
ttgcatcatc ctggacaagc accagtagaa gtgagtcagg acatgtgata aaaagacatt  61500
cattttgccc ctcctccctc tctgtatttt ctttgctata aaattattga tgttaagccc  61560
atagtactaa tatttcagtt caattcataa taaaatttga gggcatttga atatattatc  61620
tgttgtaaat tataatttta tatttgacca cagagtattt gaagtgggtc ttttctttcc  61680
ccaaaattct attttaataa ctaaaaaata ttcttaggag aagtattatt taagaacagg  61740
tttatattaa ataacatcat ttcactttca actttctggt ggtcaaaaaa tatgctaata  61800
ctaattagga tatgatacac atgttctgtt agaacagttt tggcagttag aagacttctc  61860
ttcttgtgtt tgaaagggat gttacttggg gtagttatga gccatgtatc cagatgtcct  61920
gaaaggacca gtggtagatg tatttctatt tttgtctttt cttttttctt tctggcattc  61980
tagttgctga gtgactgact tttgttttca gctcttctca caatcaccat tgttctaata  62040
actttgctta aatagaatgt ctccttttgc tataagccat ggggccattt accgttaatt  62100
ttttaaagta ctgaaatgag aacctcataa attaaagaac actcctgatt ctgagttagc  62160
agatcctact aagcctttg cagatggaaa ttttcctttaa attggtttgt tttcctttaa  62220
cattccatta tcctattgtt cattctttgg agctgtgatt tgtttaatat atttcaggct  62280
tcttaataaa tcaagtcatg taagttatta tttggatcat ttcgaaacta caacagctta  62340
tcaaacctct gaaagaagaa ttttgtgttt gcccacagac tgaagaactg attcagtttt  62400
attggctgag ctaccttcat tattcatatt taattcctgg tactgagggt gggaggaggg  62460
agaggagcag aaaagataca actattgggt actgggccta atatctgggt gatgaaataa  62520
tatgtacaac aagcccccgt gacatgtgtt tacctatta acgaaccctc acatgtatcc   62580
ccaagcctaa aagtttaaaa atatatattt ggtaaatcaa ttgatgtgtt ttaaaaaata  62640
tcgccttttg gccgggtgtg gtggcccatg tctgtaaccc cagcactttg ggaggccaag  62700
ccgggcggat cacgaggtca ggagttcaag accagcctgg ccaacatggt gaaaccctgt  62760
ctctactaaa aatacaaaaa atagctgggc gtggtggcgc gcacctgtaa tcccagctac  62820
tcgggaggct gaggcagggg aatctcttca acccaggagg cggaggttgc agtgagccaa  62880
gattgtgcca ttggactcca gcctgggcga cagagcgaga ctctgtctca aaaaaaaaa   62940
aaaaaaaaa aaatcatctt taagagata actaaccctt ccccagaagg cagggccaaa   63000
gtctaaggtt cttccaggtc cttttgtattc cctataaatt ttagagtcag cctgtcaatt  63060
tctatacaca cacaaaaaaa gcctgctggg attatgattg gtattgcatt gaaattaaat  63120
```

```
caatttgggt ataagagact tcaatttggg gattgagtct atattgagtc ttccaatcca   63180
ggaacactgt atatctctcc atttagtcag atatttagtt tatttcaaca atattttcag   63240
atctttagtt cctttcagca atattttctc attttttcctg taaagctctt gcacatcttt   63300
tgtcccatat ctattgtgta tatgtgtttt gctagttatt aaattatatt aatataaatt   63360
ttattttcca attgtttgtc gcatatatag aatgttttaa aaatattgtg tcctgtgacc   63420
atgctaaatt aactaattct agtcattatg tcttcattat ctttctcttg aattttcatt   63480
gtcttcccct tctgggactc cattcatatg taaggccatt tgatactgtc tctcaggtcc   63540
atgaagttct gttaatttt cttcattctt cttttctct gtgttcttca actgaatgaa   63600
tgccattaat aatttggtat gtaatggctc acttaaactt cctttgttt ttaagatatt   63660 tctactctca gctgtgtctg gaatcctttta gtccggagcc ccaccaaccc tcagcctaga   63720
aggaaggagg agaaggatag ggtgaaagga aggggagagc ttctagcttc aggacagaga   63780
tcagaacaaa caacagagca gtcatcttgg ataaggaaac ttccctcaaa cctattactt   63840
atatcctcag aaataagaaa ataatgcat ttatcaaatt aaaggatttt gaaaaggga   63900 acattcagag aataaaacta aactcttgaa agttaaaagg atgataacat aaatgaaaag   63960
ctcagttgaa ggattgaaag ataaaagtaa gaaaatatcc cagaaataag agcaaaaga   64020 cagcaatgta aaataggga gaagataaga gaattagaga accagcttag gagttctaga   64080
aagagaaaat gtagacaaca aaaggtaaga aatcatcaaa gactggagta ggggaggtca   64140
tgctatctgt ttctttttct attttttatt ttgagttaca ttttttttta ctgtgaaaca   64200
agcatatgta catgagaatg aacaaaacaa atatgcagtc atgtattgct taacaacaga   64260
gataggttct gagaaatgca tcattaggcg atgtcatcat tgtgcagaca tcatagagtg   64320
aacttacaca aatctgaatg gtatgtccta cagtacacct ggaccatatg gtatagctgt   64380
tgcttccagg ccacaaactt acagcatgtt actgtactga acactgcagg cacctctaat   64440
acatcggtaa gtatttatgt atctaaacat agaaaaggta caataaaaat acaatataaa   64500
agaggaaaaa aatagtacac ctgtataggt gcttactgtg aatagggctt ccaggattgg   64560
aagttgctgt gagtcattga gtagtgagtg aatgtgaagg cctaggacat ttattatatg   64620
aagtctactg tagtgtaaac tctgtagact taggctacac taaatttata gaaaaatttt   64680
cttcaataat aaattaacct tagcctactg taactttttt actttgtaaa cttttaattt   64740
ttttaacatt ttgactcctt tttagtaaca cttagcttaa aacacacaca ttgtacagct   64800
gtaaagaaaa ttttatgtcc ttcttctgta agcttttttc cattttttaag atgttttat   64860 ttttaaaact gttactaaaa actaatacac aaacacacac attaacctag gcctatacaa   64920
agtcagtgtc atcagtgttc aaccttcaca tgttatccca ctggaaggcc ttcaggggca   64980
ataacaaaca cagagctgtc gttttctgtg ataacagtgc cttttttctga tatacctact   65040 gaaagacctg gctgagagtg tttgacagtt aacaaaaaaa aaaaaggaca agaagtacac   65100
tctaaaataa tgaaaaaagt ataatacagt aaatacataa accaccaaca tagtcattta   65160
ttatcattat cgagtattat gtactgtaca cagttgtatt tgctgtactt ttctataact   65220
ggtagcacgg taggtttgtt tataccagca tcaccacaaa cataagcatg gtgttgtatt   65280
acaatgcaca gctgcagcta agtgatagga ctttttcagc tccattataa ttttatggga   65340
ccatcactat aaatgctgtc catcattgac tgaaatttat gtcgtgcatg accatacata   65400
caatttaatg aaaaataata ataataaagc tagcagtgtg taattaccaa ccagggcaag   65460
aaatagaata ttgccaatac cttggaggcc tccagtatga ccatataagt ttacaaatcc   65520
```

```
tatttttgttc ctcctcccca gaggtaacca ctgccctgac aaatgtgatc gttgttttct    65580
tgtttttctt actacctata taaacatcct taaacaatat aactcagttt gtatattttg    65640
aattccatgt taatagaata tcatatgtat atgaattta tgtgaataga atattatata    65700
tgtcattttg catcttgctt ttttcattca acattgtagg attcattcat gttgtagtgt    65760
acagctgtcg tttattcatt gctgtataga attatatcct cagagataag atatatggat    65820
gtttataaat cattccacta ttatgaacat ttgactagtt tgtagttttt atttaaccaa    65880
aaaaatgctg ctgccaacat tcttacacat tttactgtat atgcacatta atttatttac    65940
aagtataaat ttcttttga atacatatct attgatggag ttgctacatc ataggacatt    66000
cttgtctttg actttactgg ataataccaa actgtcttcc aaaatgatta catccttaaa    66060
ctcaggacac atcttattgt caaatgttta attttgtca gtctgatggg tatgtaagtt    66120
attttattgt cgttttaatt tgcatttccc tgattactaa ttaagctgag taacttttca    66180
tatgtttatt ggccatttgg agttcctgta ttgtaaagta taagtttttt tgtccatttt    66240
tctagttttc tgtccttta gttgaaatcc aaatttgcct aaatctgtta ttctctgagc    66300
acaagtaact tgggatgctt cctttagat ttagcctaat tctttatcat tttgtcagct    66360
tgatggtgct tttaaggaga tatatatgtg tgtgtgcgca cacatgtgcg tgtgtgtata    66420
tatatatatg tatatgtatg tatgtatttt ttgagacagg gtctcactct gtcacccagg    66480
ctggagtgca gcggcacagt cttggctcac tgcagcctcc acctcctggg ttcaagcttt    66540
tccctgtctc agcaacccga gtagctagga ttacaggtat gccaccatac ccgctaattt    66600
ttgtatttaa tagaaacagg gtttcgccat gttgacaggc tggacttgaa ctcctcactt    66660
gaactcctca cgtcaagtga tctgcctgct ttagcctccc aaagtgctgg gattacaggc    66720
atgagctacc gcgcctggcc tggatatttt ttaaaaatat ttttatcta gcactttgt    66780 ttttggcagg caggttggca ctcatagtct gacctaccat ttctataaaa agaaacctgt    66840
aaatgttctt aaacagactt tgaaccagtc ttcctgattt tgaaccccta cctttacccc    66900 cagttttga gcctttcaga attttttttc ataataatta ggttgcttct tagctttccc    66960
cactggtgac ttaacagatc ttaggaagcc aacaatcctt gtccatctgc tttctgtctt    67020
gtgaactgtt gctggtattg tctcttctct ttattcttag aggtgtatgc ttttaaaaac    67080
atatactggg tttgagaggg agctgaaata aaagcatgtg ttaaatatac catctttaac    67140
cagaactaca tttgactggt catttttatt tcaagctcac atacacttca aacagagata    67200
tggctaaagg aattatcatg tgaacaacag ccagggctct gaacatcaca gattatatca    67260
tcatacttga aatatttgaa attttgattc aaaatgagag ctttatagct atgtcctcaa    67320
tggactaagt gtttaagtac ttaacatcca aaacattctt actaatcaag agaagacaaa    67380
caccccaaca gagaaatagg caaattttat caatagccag ttcaccagat ttgttttctg    67440
ttagaagcga atatggggaa atacatgtgt ccatgttttg cctactttc ctggagcagg    67500 taaggagagg cagtttaagg atccatgtga taaaccctaa agttgtccat cggctttcca    67560
gtcccttcta ggaatttaac ttagggaaat aatcagacat ttgcaaaggt gtgtacagtg    67620
gtatttataa tagtgaaaaa ccaaagaatg accaataacg ggagaatgga agttacagcc    67680
aaatacttta caactactaa agaatcatgt aaaatatcta ttgacatagg agttttatca    67740
aaatgtgaag tatacagatg aatagtacca cacataaaaa gcaaggtgca aattagccat    67800
ttatattgtt atccccaaaa taaatagatg cagtttttt aaaagatgca ggctatatat    67860
```

```
ggaagtgttt gctggttttc tgtcaaaaga atggcgactt tattttctaa tttaaacttt    67920
ttgctgtttt ctaaattgtc taaatagtta tagtttttat aatgtaaaag tatcttccaa    67980
tttagcttca tttgacaaat tacctttttca ttctatctag ctatgtaatt ctaaatgaat    68040
ttacagcagt aatcttagag cagatgaatt tacaacaata atcttagagt agactacgga    68100
ttagatgtaa aaacatgagt tgggctttat ggttacagag agttttcctc agtgtgggga    68160
tcatagctgt attgagttta ttcagttttc ctttcccaca tgaatgaaaa atggggccag    68220
cctacaactg gaagggcctc ggcatgtacc actgtactgt gtatgatgtg atttcttgat    68280
gctagtaggg agagaatcaa attgcctcct attcaaacca agaccacaa atagcgtcaa     68340 ccagtcattt cagctactcc ctgcagtgtc aagaaggtgt gaaccccctca tgttctctat   68400 tgcataccct tgtctaattc agtgtttctt cttcttttca ggttttggct ttatgctaca    68460
tttcagaaat cataataacc ttttctggta ttattttatt cttttttcgca ctgtgagaaa   68520 aattaaactt tcaagtggat gcttcttata aactatttat accctttttgc tccctttggg   68580 gaggcaggga cagggacaga gttcctcctc aggctaacta agaaaactta ctgcttccaa    68640
tgtaatttaa aagatctccc tctttctatt gctctctgta ctcttaattc ttttttttttt   68700 ttttcacagc agagacaagt gaacatttat ttttatgcct ttcttcctat gtgtatttca    68760
agtctttatc aaaacaaggc cccaggactc tccagattca attatgtcct tgggcttggt    68820
cgactgctgt aggagtctca gggagccttc tacaaatgct agagtgactc atttaccaac    68880 attaaacct aggatacatg caacaaagca ggactccttc ctccatggaa tgtgccgatt     68940
tcagatgaca cagcacccaa tgtagaaaac gctggaattt ttccttggaa ctagactgtg    69000
atgagaggtg cttgacatga acataagcta ctgtctttc ttttttttg agacagagtt      69060 tcgcttgttg cccaggctgg agtgcaatgg cgtgatctca gctcactgca acttccacct    69120
cccaggttca agcgattctc ctgcctcagc ctcctgagta gctgggatta caggcacgtg    69180
ccaccatgcc cggctaattt ttgtattttt agtagagatg gcatttctcc atgttggtca    69240
ggctggtctc gaactcccaa cctcaggtga tctgcctgcc tcagcctccc aaagtgttgg    69300
gattacaggc atgagccacc acgaccggcc agctactgtc ttttctttga cccttccttt    69360 ccagttttg aagataaagc aggaaataat cttctctgaa gatacttgat aaaaattccc     69420
aaaacaacaa aacgcatgct tccacttcac tgataaaaaa tttaccgcag tttgtcacct    69480
aagagtatga caacagcaat aaaaagtaat ttcaaaaagt taagatttct tcagcaaaat    69540
agatgattca catcttcaag tccttttga aatcagttat taatattatt ctttccccat     69600
ttccatctga atgactgcag caatagtttt ttgtttgttt gtttgtttgt tgtttgttt     69660 tttgagatgg agtctcgctc tgtcgcccag ctggagtgca ctggcgcaat cttggctcac    69720
tgcagtctct gcctcctggg ttcaagcgat tttcctgcct tagcctctcg agtagctggg   69780
actacaggca cgtgccacca cacccagctc attttttgtat ttttagtaga cagggtttt    69840 caccatgttg gccaggatgg tctcaatctc ctgacctcat ggtctgcccg ccttggcctc    69900
ccaaagtgct gggattacag gcgtgagcca ccgcgcccgg ccagcaatac agttttttagt   69960 tactcgacat cttttaagcct ataactctta ggctatgcat agcccatgt cctaatcagg    70020 cattcactga tccagcagg tctccatcta tttgtaccag cctcctcttt cctcccaatc     70080
tcaaggttac tcttaaatac tagtaaatgc aaaaagaact tgtaaagtgg caaggcatgg    70140
cctatcaaaa gtcagcccaa gggcagtttt cagccctgcc tcacctgggt ctagttcagc    70200
tgacggatga gctgattgat gcgttcaccc cgatagccag gtgtgcccat ctccttgagg    70260
```

```
aagcccactc tattttttggt agcatgatgg gccactgaga ggtggaaagg gcgcaagaac    70320
catgagatct cctggaaatg cttccctggg aaggcaattt catgaatgag gtcttccaag    70380
caaatgaagc caaacttccc caggtgctcc tcaatcactg tgttgtctgt cagagggatg    70440
gtcttattct tgaccttggc ttgtccacgt ttcaaaatga gttctcggac agacttcaga    70500
tttggaaatc cccaggtcac ataaggttcc actatatgca gcattttag attctagggg    70560
gtaactttta caaagatacc actaaaaatt ttctttaggc gaagtcttgc agtggttctc    70620
tgcacccgta aactcacgcc atcaatcctt tcgatgcgta caacaaaggc caaggaatgt    70680
ttatctggca attccaaggc atgaggtttc acttctagtc gtctgagacg caccttgtca    70740
cgtttctgcc gccaggaatc atgtaggaat gattccagtc gcttaaacct gagccctttt    70800
cctttcttct gtcttgctac tgccatcttt ctagtggtgc agctactcaa ttctttttt    70860
aattataatt tttatttaa gttccagggt acatgtgcag gatgtgcagg ttacataggt    70920
aaacatgtgg ccatggtggt ttgctgtacc tatcaactca tcaggtatta agcccggcat    70980
gcgttagcta ttttttcctaa tgctgtcccg ccccccccacc caacgggccc cagttacact    71040
cttaatcctt atagctcaga tgttatgatc cacagtgtgg ttcttacaga aagttatgga    71100
ttaaaaaaaa aaaaaaacac tcaaagtgcc cgaactttct taaaataatc ctggtacagc    71160
taaactcatg cactgactgt ccacctaata tttaacagtc tgtgttgtga tatattgttt    71220
taatgttctg aatgcttgtc agctttcagt attgaagatg tgaatcattt atcagcaatg    71280
acacatttag tctaaggttg tcagctattt atgctacaaa ttaatgactt gtccttaaaa    71340
tatcaatttt gtgattcatg ttttggcagg tggttagatg ttttgtgttc taatttaaa    71400
ctatggataa aggttttgtc ataatcattg ttttattggt tccttttctc ccctgcccac    71460
tccccaaaaa accctgcaat tctttttttgt taaacttta ttttaggttc agaggtacat    71520
gtgcaggttt gttatatagg caaattttgt gccacagggg tttgctgtac agattatttc    71580
atcacccagg aaataaacac agtacttgat ggataggttt ttagtcttca ttctcttccc    71640
accctcaagt aggcccccagt gtctgtcctt cccttctttg tgtccctgtg tactcaatgt    71700
ttagttccta gttataactg agaagaacat gtggtatttg gttttctatt cctgtgttag    71760
tttgcttagg ataatggctg ccagctccat ccatgttgcc gcaaaggaca tgatttcatt    71820
cttttttatcg ctgtgtagaa ttccatggtg tatatgtacc acatttctctt tatgcagtct    71880
tctgttgatg ggcttttagg ttgattctat gtctttgcta ttgtgagtag tactgcagtg    71940
aacatacaca tgcatgcgtc tttatggtag aatcatttat attcctctgg gtatataccc    72000
agtgatggga ttgctgggtc gaatggtagt tctgtttttaa gttctttgag aaatcatcaa    72060
actgctttcc acaatggctg gattaattta cacttccacc aggagtgtat aagcatttcc    72120
cttttctctgc aacctcacca ggatctatta ttttctgact ttttaataat agctgttctg    72180
actggtgtga gatggtatcc cagcaccatt tattgaatag ggagtccttt ccccattact    72240
tgttttttgtt gactttgttg aagattggat ggttttaagt gtgtggtctt atttctgggc    72300
tctattctgt tgcattggtc tatgtgtctg ttttgtacca ataccatgct gttttggtta    72360
ctttagcctt gtagtagttt gaagtcgggt aatacggtgc ctccagcttt gttcttttgg    72420
cttaggattg cttttggctat ttgtgcccctt ttttgattct atatgaattt taaaatagtt    72480
tttttctaat tctgtgatga atgtcattgg tatttgaga gcaatagcac tgaacccgct    72540
aattgctttg ggcagtatgg cgattttaac aatatcgatt ctttctatcc cctgcaattc    72600
```

```
tttgttgttg tatttaacta tttttacttg tgaagttttt tcagggatga ttttgttgaa    72660
agtgacaact ctaaaaatta tgttggtaat taaaatttta agtaatgact tttattttca    72720
gagattccac ttctcttaga ctttggagct gttaacagca gtgtccaatc tgcagtggta    72780
ctcagcagtt tctgtttcct gcatgcagaa ctgcttatat gaaaacacag ttttaaaaat    72840
gctttcttat ggctgacatt cacattctta ttccttttga ttcttttcaa gagggatttg    72900
gtttgttaaa attaattttt gcaatacttt tatgaagata caaactctga caaagctttt    72960
aaaacaagtt tgagagaata cagtattgat ttcacttgta aatctgacga ttattttaga    73020
aaaaaggaaa atattattta ctattatttt gcttataaat gtttatcaat tttaaagctt    73080
ccacattgca catctcccac tacaacagta gctaccattt attctttctc aaaaaaagtg    73140
ctaagtgtgc ccttgaaatt tttacattgt gcagaatatc cctaaaattt taaaacaaaa    73200
attacatcat cacttgcttt aaatgtttct tctttattta acatacagtt tctaaaatgt    73260
tagcaaatag cattttagaa gagacacgtt acttttctaa tgaatgttct aaaatgaacc    73320
acagtaaccT atacttactt agactgtgaa aaacaaaact tatattctat tgttaaattt    73380
tcaaaagtga aactcacga tagtttactt ggcacatcac tctgttattg tgaattgaca    73440
aatgtatatg tagacaaata tgtgaaaatc agagtacata tacattatat gcagcaccac    73500
aatacatttt ttagtatgtt ttgactgata tttaattata taatttacca agaggatctc    73560
accagaatgt agaaaagtat tgaattttag aacaattcac atatttaaaa aaaatgtagt    73620 cagcccctt atctgtatct ggagaatgca gggtaaagga ataatacatg agtattggta    73680 ttaaaaaaa ggtgttaatt tcttacctat gatacctgtt actttgggta tcatttaacc    73740 ttatttctg tgaaatagag gagttctaac atcctctaat tattataata ttgttctaat    73800 taatctatc ttaatctgtg atacagtttg aaaaccaagc ttttactatt ggcatgtgca    73860 aaaaataaa gcagcagtag acttggaatc ttgaatgcaa atttagattt tgcctcttaa    73920
taaatgtata atatagtgtt ctgggaccaa ttctctaaca tttctgagtc ctagtttctg    73980
catctgtcaa atgggattag agatacctac tttcaggatg tgatatggtt tggctctgtg    74040
tccccaccca aatcttatct tgaattgtaa tcccatata ttgagggagg gacctggtgt    74100
gaggtgtttg gatcatggaa gtgatttcct ccatgctgtt ctcgtgatag tgtgggagat    74160
cgcaaaacat ctgatggttt aaatatggca gtttcccctg tgctttctct ctctcctgcc    74220
accatgtaag actttccttg cttcctcttt gccttctgcc atgattgtat gtttcttgag    74280
gcctccccag ctatgcagaa ctatgagtaa attaaacctc ccttataaat tacccagtct    74340
cagatattct ttatagtagt gtaaaaactg actaatacag gaattggta ctggcagggt    74400 tgggtactgc tataaagata atctgaaaat gcggaagtga ctttggaact gggtaacagg    74460
cagtggttag aacagtttgg agggctcaga agaaaactgg aagatatagg aaagtttgga    74520
acgtcctaga gacttgtttt gaatactttt gaccaaaatg ctgatagtga cgtggacaat    74580
gaagtccagg ctgaaatggt cccagagatg aggaacttat tgggaactgg agcaaaggtt    74640
atttttgcta tgctttagca aaaagactgg cagcatttta cccctgccct agagaactga    74700
tgaactttga gatgatttag ggtatttggc agaagaaaat ttctaagcag caaagcatcc    74760
tagtggtgac ttggctgatt ctgaaagcgt tcagtcatgt gcattcacga agatatggtc    74820
tgaaattgga acttaggttt agaagtgaag cagaacataa aggtttggaa aatttgcagc    74880
ctgaccatgt agtagaaaag aaaacccat tttctgggga ggaattcaag ccagctgcag    74940
aaatctgaat aagtaacaag gagtaataag taataataag taaaaagtaa taagtaataa    75000
```

```
gtaacaagga gccaaatgtt aataaccaag acaatggaga aaatgtctcc agggcatggc    75060
agagatcttc ggggcagccc ctcccatcac aggcctgaga actaggaggg aaaaatggtt    75120
tcctgctcag ggccttgctg ctctgtacag cctcacgaca tggtgccctg catccctgat    75180
gctccagctc cagctgtggc tgtaaggggc caagttacag ctcgcaccat tgcttcagag    75240
ggtgcaagcc ccaagctttg gcagctttca cgtggtgttg ggcctgcagg tgcgcagaag    75300
acaagagttg aggtttggga acctgtgcct atatttaaga ggatgtatag aaacgcctgg    75360
atgtccaggc agaagtctgc catggaggca gagccttcat ggagaacctc tgctagggca    75420
atgcggaagg gaaatatggg gttggatccc tcatacagag tccccactgg ggcactacct    75480
agtggagctg tgagaagagg gcctctgtcc tccaggcccc agaaaggtag attcaccgac    75540
agtttgcagt atacgtctgg aaaagccaca gaatgccagc ctgtgaaagc cacagggta    75600 ccctgctgag ccacagggc ggagctgccc aagggtatga agcccaccc cttacttcag    75660 tgtgccctga atgtgagaca tggagtcaaa ggagattttg gagcttttag atttaagggc    75720
tgcccagctg ggtttcagat tcatggggc ctgtggccct tggtttgacc agtttctccc    75780
atttggaaca ggaacattta cccaatgcct gttccctcat tgtatcttgg aagtaactaa    75840
cttgcttttg atttatagg ctcatacgtg aagggactt gccatgtctc agatgagact    75900
ttggtcttgg acttttgagt taatgctgta ataagacttt gggggactgt tgtgaaggca    75960
taattggttt taaaatgtaa aaagacatgg gatttgagag ggagcaagtg caaaataata    76020
tggtttggct ctgtgtcccc acccaaatct aatcttgaat tgtaacccgc atgttttggg    76080
ggagggacct ggtgggaggc agttggatca tgggggggtt ttttccatgc tgttcttgtg    76140 ataggggagtt ctcaggagag ttgatggttt aaatgtggca gtttcccttg tgctctttct    76200
ctctcctgct gccaggtgag acgtgtcttg cttcccctgc cccttccacc atgatcataa    76260
gtttcctgag gcctccccag ccatgcagaa ctgtgagtca attaaacctc ctttccgtat    76320
aaattaccca gtctcagata gtatctttat agcagtgtca gaatggacta atacaggata    76380
gtaatgaaga ttcagaata tgtagatgaa gaagtgctaa gtaaatagca gctattatta    76440
tgtagtcaaa ttgaatgtat acattgtggt acttcagtgt cctttaaatt gaataactag    76500
aaatttgttg gctttctcaa tctgctcaca tcagatgaca tgttaattta tgcctatact    76560 ttttctagt taatagatat aaatctattc actcaacttc tattgacaga actggtagtg    76620
tggcaagaca tctcatttct agttaaggct gtataatatt aagttcattt tacttaaatt    76680
aactatggtt tgggaaatgc ttttcatgtc atcatgtatg cccaatttga tactttagtg    76740
ggacagtata tttcagaaaa aaacaaatgc ttccccaaaa attccagggt tgaatacatt    76800
agtcagacat ataacaatgt acttcagagt tcctctaagg gcaaaaatcg tggtatgaat    76860
atacaaaaca ctcctatta tacttttgta tttttgaaat gtagtcttca tgttaattta    76920
gcatttcaat gaccagcatg acattatctt aataatttgg aatgccaata tgttcattta    76980
agacttaata tagtaagtat ctaaagaaaa aaatggaagt gactgaatgc ttttgtatct    77040
cttaattata atttgtgctc cattgtgata tgaaggatag aaggggcagg atagatagaa    77100
aacagaaatt aactttgatg tttaaccttta ccttaagact gtctgttaag tgacccacat    77160
aatcttaaaa aactctgtca agcttaatgg atgctactct gcaggcccct gccaggcaac    77220
agtcacaagg ttatgaggtg catagatttt ggaattaggc agagctgaat tcagatccag    77280
gtgttgcctt ataatgcgac tttgggcaaa taaaaggccc aattttgta ttcttatctg    77340
```

```
taaaatggac tcagtaaaaa ttatttgaga taatttattt gtgtactgta cctaggcatg   77400
cagcttgaca cacagaatta caagtcagta gtttccagta tgattattat tgtgaaagag   77460
atattttgtt tcacctactg aaaacttttt tcagtcttaa attttttatc taactggctg   77520
tattgcagat gtctgctata taacttttat ataatttaa aaactatttc tttcctcctt   77580
gatcttctag gggtaaggtt accaatgttt tcattattta ctaaatatag cagcccccac   77640
cccttattca tggaggatag gttccaaaac ccctagtgta tgcttgaaac cacagaccac   77700
agataatccc aaatcctata tgtatattgt ttttcctata catacatacc tatggttaat   77760
gtttaaccta ctaattagga agagtaaaag agtaatagta actaataata aaataaaaca   77820
attgtaacaa tattccagca tcactattct tgtgctttag gccaccatt aagtaaaata   77880 agggttactt gaacacaagc actgtgatac tgtggcagtc caactggtaa cagagatagt   77940
gatgcggttt ggctgtgtcc tcaccagaat ctcaacgtga attgtatctc ccagaattcc   78000
tatgtgttgt gggagggacc caggggggagc taattgaatc acagggtctg gtctttccct   78060
tgctattctc gtgatagtta ataagtctca catgatctga tgggtttatc aggggtttcc   78120
ccttttgcct cttcctcatt tttcttttgc caccaccatg taagaagtac cttttgcctc   78180
ccgccatgat tctgaggcct ccccagccct gtggaactct aagtccaatt aaacctcttt   78240
ttgttcccag ttttgggtgt gtcttttatca caagcatgaa aatggactaa tacagtaaat   78300
tggtaccagt agagtgggtg ttgctgaaaa gatacccaaa aatgtggaag cgactttgga   78360
actttggagg actcagaaga agacgggaaa atgtgggaaa gttaggaacc tcctagagac   78420
atgttgaatg gctttgacca acatgctgat agtgatatga acaataagat ccaggctgag   78480
gtggtctcag atggatatta ggaacttttt gggaactgga gcaaaggtta ctatgttatg   78540
ttttagcaaa aagactggca gcattttgcc tctgccctag agatttgtgg aactttgaac   78600
ttgagagaga tgatttaggg tatctggtgg aagaaatttc taagcagcaa agcactcaaa   78660
aggtgacttc ggtgctgtta aaagcattct gtttttaaaag ggaaacagca taaaacttca   78720
gaaaatttgc agcctgacaa tgcagttgaa agagagaaacc cattttttga gaagaaatta   78780
aagctggctg cagatatttg cataagtagc aaggagccta atgttaatcc ccaagaccat   78840
ggggaaaatg tctccatggc catgtcagag accttcacag cagcccttcc catcacaggc   78900
ccagagaccc aggaggaaaa agtggtttcg tgggccaggc ccacggtcct catgctatgt   78960
gtaggctagg gactttgtgc cctgtgtccc agctgctcca gctgtggctg aaaggagcca   79020
atatagagct caggctgtga cttcagaggg tggaggcccc aagccttggc agcttccaca   79080
tggtgctgag cctgtgggta cacagaagtc aagaattgag gtttgggaac ctctgcctag   79140
attttagaag acgtatggaa acacctagat gcccaggcag aagtattact gcagggcagg   79200
gctgtcatgg agaacctttg ctagggcagt gcagaaggga aatgtgggat tggagccctc   79260
acacagaatc cctactgggg cactgcccag tggagctgtg ggaagagagc cgtcatcctc   79320
cagaccccag aatggtagat ccaccaacaa cttgcaccat gtacctggaa agccacaga   79380 cactcaatgc cagcctgtga aagcagccgg gaggtaggct gcaaagtcac aggggcggag   79440
ctgcccaaga ccatgggaat ccatcttttg catcagcatg acctggatat gagacctgga   79500
gtcaaaggag atcattttgg ggcttttaaaa tttgactaac tcactggatt tcagacttgc   79560
atgggccccg taaccccttt gttttggcca atttctccca tttggaacag ctgtatttaa   79620
cctgtgacac cccctacccc cctgcccccc atccctccgg cccttgtatc tggaagtaac   79680
tagcttgctt ttgattttat aggctcatag gcagaagaga cttactagcc ttgtctcaga   79740
```

-continued

```
tgagactttg gactgtggac ttctgggtta atactgaaat aagctaagac tttgggggac   79800
tattgggaag gcatgattgg ttttgaaatg tgaggacatg agatttggag gggccagggg   79860
tggaatgata tggtttggct gtgtccccac cctaatctca acttgaattg tatgtcccag   79920
aattcccatg tgttgtggga gggacccggg ggtgggggtg cagtaattga atcatggggg   79980
ctggtctttc ctgtgctatt ctcatgatag tgaataagac tgacgagatc tcatgggttt   80040
atcaggggtt tccaaaactt tgcctcttc ctcattttc tcttgccacc accatgtaag      80100 aagtacctt cacctcctgc catgattctg aggcttcccc agccatgtgg aactgtaagt    80160
ccaattaaac ctcttttct tcccagtttt aggtatatct ttatcagcag tgtgaaaaca     80220
actaatacag atggctagta agggactaac cggcagggag cgtctccagt gtggatatgc   80280
tggacaaagg gatgattcac gttccagggc ataagatttc attactcaga attgcacaga   80340 attaaaact tattaattat ttctggaatt tccacttaa tgttttcaaa ctgtggttga       80400
ctgcaggtac ctgaaactgt caaaagtgaa accacagata agtggggagt cctgtaccta   80460
agattattcc tttaaattgt ttcagtggat atgtagggac ctgagtgtga agtgagagca   80520
gcagcatcaa aacctgaggg aaatccagat agcaaaagaa acttgtctag tatactggca   80580
tgacagagaa accaaaaagt tctcaagtta atgtgagaat ctaagaatta aagaattaag   80640
cctttgcctt tgagggaagg aaaggggtaa tgtggcttta aatcaggttg agattggttc   80700
tgagggttcc ttttccttcc tttatattga tatgaatata gacacaactg ttctgcattt   80760
ccatttgttt ttataaatgt ctttttagga tttaggaact gctaattatg caatatgaga   80820
tatctgttag tttgaggaac atttgaaaat ttggtcaaat gacacagatc gtcacacagt   80880
tttaagacaa atgtttttac ctatttgacc tagtctggca atccctattt gggcaaaaat   80940
cttcatttgc aggtcatgat tggaggcagg cacagaaaaa aaattgccac cttttttgca   81000
ttatgtcatc aagacatcaa acttcagcct acaaagtaga aagtgttatt tctcaagttg   81060
aaggcctgga tatacctcag cttctcagtt ctgacacttt atcatagtgg aaaatgaaga   81120
agattgctta agaacactga tgttggtgtc agaaagacct gggtttgaac cctgacttta   81180
ctagttactt agatcacttt aggcaactca acttttctaa atcttgtttc ttcatctgta   81240
aatgctgaaa atagtaccca cctcttaggt ctgtggagag gattaaatga gataatctat   81300
acaaagaaag agcttgcata atagtgccaa gtaatggtga ggttatacct gtattctgat   81360
tataatctca taaatatta ccatgttagc tgtctcagag ttcttttgca aaacagataa     81420
agatagaaag tataaataag aaaaataagt gaacatatac tgaactttgt acaagatgct   81480
ggcgatatgg agagacccaa gacatgggcc ctacctaaaa gagattattg atagaaacag   81540
gatacatata catcaaaagg taacatagga tcatctgtgc aaagtgctat atggcagtgt   81600
tttaggaagt ctagaagctg tcatggatca ggaataccat ggtggacact tcaggcaggg   81660
aaaacagatc ttagcaaaag ctactcctat cataggtact tgataaatat ttgtagaatc   81720
caggatccct gtagtgataa agaaactaca tggattatgt aggggagtga taagacatat   81780
gactggaaaa ataaaaagac caaattatgg accatactga gcttgtacta taaacagtgg   81840
aggagccctt cagatttta atcatgttga gaaaagagtt ttagcagtgt gtggggata      81900 gaatggaaag agaagccagt gccagaagga ctacttagta tcaaccattg cagtggttaa   81960
agcaagaggt gagagaaggc atgcattaga atggcagcgg tcagagtgga tgggaaggaa   82020
taggtcctga catagtgtta cagggagtaa taaataggat gtggaagatg ggttagaatt   82080
```

-continued

```
ggcaaaatct ctgcatgtaa gtctgggtta ctaaatatag tgagagaaat tcaaatctct      82140 cttttaagaat cgaataaaat atttagaaat aagttactgt tgtatttgag gtgaacacaa     82200
atggcatttc aaagatgctc gagataccctt gttggaaaaa gtcaataact gcactattgt    82260
ctccaacatg ttcttgcctt ctctgaagac atcatgttcc taattctgaa ttatgaacca     82320
tctattatcc ttgtatgctc ttatgtgtga ggaaccataa ggtgggaaca aaatccggtc     82380
ttcattctag aaataactat gcgatcaaaa agttttagt ctttcttctt accatactgg      82440
ttcttggtat tctgtttacc attcaatgta ctattattgc ttctgcttaa aactcgcatc     82500
ccctaatgca agcctgagca aacagaactg ataacacaca gcctgagaag ggagtgcttg     82560
gggtctcaag acttattctg tttttctcca tctttgacac ttggtttgaa gagcaaagaa    82620
ggatacagct gttaggaagt aagttaccca aacacagtga ccaaactgga ttaattcttc    82680
caatgagaaa gaaatacatt atttctgtga gacagattag actttaagta gcatagataa    82740
catgattata ttctctctac aaataaatac acaggaccta agaaaccctt tacagatcca    82800
agtgttttcc tctccacttt tccatcccca aacccatctt gcaagatatg ccagcttat    82860 ttggagttaa ttaaatcaag accttcgttt tacagacagg gaaaccaagc ccagagacac    82920
tgagtagtag gccactggtg tcttagaggt ctgaaaaatc ctttactgaa cattctcttg   82980
atctattaat gtataggttt tgttgctgta accctctccc caagaggagt gaatataaat    83040
gatgcagagt ttggatgaac tatcttaata agaacctaaa gttgaaacca atgcaaacct    83100
ctctcaataa atgcaaagca aagagaataa tcagtctttc tttggcttgt taaataagat    83160
aaaatgtgtt ctgctaaaac catttaacag aaatattgtg aaaggtttcc cctaaagcat    83220 ttttctatttt gatttgaaaa ctattccata gcttattatc aaacaaatca gtaattcttt   83280
agctaatgca gagataaatg ggcagtcaga aaatataatc acctggtgtg tgcagctgag    83340
tatttacatt tttcctaatg aacaaagata agaaaagtgc aggtgacttt aatgtgtaaa    83400
aactaccttt tagtgctagc gctagaggga aaaagaaatt actggctcaa gccaatcctg    83460
tacttgataa ctaagccgta tagtccatgg cttggcttca gttctgtttt gaatctcttt     83520
ttggacttgt cttgaatgga ctgtttaggg ctgcttcagt agtgcagttg ttgcattttt    83580
aagcatagtt taggttttaa aatgtttctg gtccctttt tttttctttt tccactttat    83640
gttgcttaaa gctttatggc caggttttct catcctcagc attattgaca tttgaagctg    83700
gatacttctt tgtggtgggg gctgtcctgt gccttgtagg ctggttagca gcatccctcg    83760
cctcttctca cttagatgcc aatagcattt ccccaaccgt gataaccaaa agtgttttca    83820
gacactgcca aatgtctcct agagagcaaa attgctctct gttgagaact actgtgttac    83880
ggtgtttgga caaaaactga caagccaatg ggaatattct attggtagtt gtaaaaaatt    83940
aatccagtta tagcagctgt atttctggaa tttttttcca tattaacact tgctttctga    84000
ggtgataata tctttgtttt ttttctccca aatagatttc ttgcattaca ctgaaaaatt    84060
gctgattaat tcacttaaat tgaagactaa gccaatcatg tcatttgggt aatagtttac    84120
caactctgcc ccttttctctg tcagggaagc ctctaattta gtaagcgata ctgtatcctt   84180
ttgtcaggta cattaccatt cctattagca ataggggcaat tgagattgag aaagattaaa   84240
aggtcaccaa gctattacat tgtagaatta ggttatgaat tgtagcctat ctggtttaga    84300
atctttacct tactagtctc cataacaaca attcttccag tgtggtccat ggggccctgg    84360
gagtctcccc ttaaagggca gactattttc acagtaacac gtactttatt tgccatttca    84420
ttatgtcagc atttgcaata atggtacaaa agcaaagatg agtaaaactg ttggcatctt    84480
```

```
agtatacagt agttactgta ttcactgtca tgcacttaaa atctttgaag aagcaaaaaa    84540
attattaatt acattaaatt tcaacccttta aatacatgtg gtctttctca tgtcagtgtg   84600
acaaaatgag aaggtgcata atccacttat atcgcatata gcatttgata gttgtctcaa   84660
agaaaagtgt ataagattaa actgtgagtt aacctacttt ttttcatgga gtaccatgag   84720
agataaactc tggttttcag ccttgggtat ttggcgatgt tttcccaaaa atgactgaag   84780
taaacttagc actttaagga aaacaactta aagtatttgt tgccaattga taaaatatag   84840
gtttcaagca aaaatcagaa tttttgaaga cttgtatctg ccactgtgag cttgacaaat   84900
gtgactcttt tatattacat aatgaactat gtcaacattt gaaagatctg cataactcag   84960
tgaaccagta ttttccagat gactaatgca tgataaataca aaatcatgca tgggtaaaag   85020
atacattcaa agtgcaagat agactgacat atttcaatgt aacaatcaaa agttcattga   85080
taacagtttt ggattccaca ttgcaatact aaaacccttta aaaaacgaaa ttgtccaatt   85140
ttggtgtagt aatcagaaaa ggcaatctat aattacctga acttaagttt ctggaggacc   85200
attaaccttc tacaggctca tggggaagac tgtagcactt ctctttccct aagatcctcc   85260
agaaaggaag aaggtaatcc ttgggggtag ggtagagacc tattgtgtga tgatcaccaa   85320
gtatgtaaca atgctttata taactctaat atatataatc cacacaaacc ccctaaaatg   85380
gcactaataa gggaatggac tcaaagaagt taagtcagct agccactgtc acagctatta   85440
gagcactgga actaggattt gaacccagat ttgtctgtat gtaaagctga ttctcttcgt   85500
aatagtactg agacacaaga ggcggctaca aaatattctg gtactccatc ctagaccaga   85560
gtttcaaggt tcgttatcat ttgtagcatg atactggatc ctcacagtgc ttgcctttca   85620
ttcaggtgcc aggaaacgtc tgcctgaatg aatgggtgta atttacctgc acattttaca   85680
tgcttctcta ggtgtgtgat taactcataa tccatccatg actttcaccc ataatcctcc   85740
ttgtagcaat tgctttgctt gcaacaaaac taagtagaca tatctagctt tatgcatggt   85800
tttctctctc tgaactctaa cataaactca gcctcaggaa ttattcggtt tctactacat   85860
ttgccattct gattgggaac caccagcatt caggtattca cctggaacaa ggcattttgt   85920
tccaagggtt cctcacttaa aagcaagcac cctagcaata gttcataatg gaacttctta   85980
acattctcag aatgtttggc acagctgtga gtgaacacac attgagcaat caataactat   86040
tacagataat gatgcccttta agaccaggat atttttagctt tcccattcaa aggggtgaa   86100 atatgcactc ttactatggt atacttttgg ttccttctgc catgtatcct taataaaaga   86160
tgtcaattcc atatggtttt ctcttgagtt ctaaccattt tgttgtaccc tagccctttt   86220
aacaatatca aacttgcaac tgaataccat ttagcattca tccatttttt ccaatggtgt   86280
tcattatagg ctatcttact cctcctattt gtatgacaaa aattggcttt tttcaccgat   86340
gtctatggta catctggcag ctttttccatgt actcagttct tatctgatgt agcccagaac   86400
gactgcctga agggatgcca aaagcctgat tgaggttcca aatttttcagc tactgtacta   86460 tcaatccatt tgttcatttt tactttccct tgtcatctgt agcttacagt tgagtggcct   86520
gaacatgttt tgcatacatt gtaatatcta agaatttggg aatacggtcc taggatttag   86580
acttaatact accttccatt tatataatac ttactcataa aatcttcagt gttcctgaaa   86640
aagaaaaagg aacatgtatt gagtgcctgc tagaagcagg aacttgtagt agattttcta   86700
tgtgttacct tattttcaca acacacacac aggtgatatc cttcccagtt tactgatgag   86760
gaaactcagg ggtcaaagta gtagataacct acccaaggta acagaagctg tgaagtggta   86820
```

```
cagctgggat ctaaaatatg tcagcttcac cgtagatagg ctccctgatg aaccacctgc  86880
cacggcccgt atgaccgcat ccaggggtga tgatgtcatt ttcacagggt tattgagagc  86940
taaaactacg aagtactaca aactattatt taaaatataa atacatacta tatatgcata  87000
tgtgtgtata taattaat ggggtaaaca ttacagaata ctgtcctaac ctttaaacaa  87060
tgcactcgtt ttctgtaaac taatatacaa acaactgttt ggtccctaaa aatagatgtc  87120
aggtgacaga gactggctga gcaagaatag gagtatcttc agaatagaag ccagaggagt  87180
ttttgcttcc ccaacacatt gtcgcaccat tcactgttcc aggaccttcc tacttctctg  87240
gaaaactctg gcccaaagca gctcctctac attagtcaca agtttccatt aatcagggt  87300 ggcctgtgcc ggacctacag cagagtcatt tcaggttatt ctgttacagg ctttcgacgt  87360
gtagtcagtc cactcgccca aatctagcag ggaatgaatg ccttgtaata cggaagcatc  87420
tacaaattct tcttaacagt gttcagagaa caatgtgaaa ccctggggcc ttttcccaga  87480
attagggtgg tgggaatgct gtcctattga ctaagcctgt taggtaagca ggcagttggc  87540
aagattcagg aagcttcatt tgaagataga atttagggcg atcgtttgga tttactggct  87600
taattactta aggtaacatt tataaaagaa attgtcattc cattattatt acctttaac  87660 ttttattcct aaacggaaca ttagcaacaa actacattac ttgataaatg taatttctaa  87720
ccagattgat aactagaaaa aaattttaag ttactttgct ctgtgaatta gtttaaacat  87780
atttgtaatt gagacttact actgttattg gctgaaataa ataaaagcaa gagataataa  87840
agaataacag agacaacgaa cacccaattt aagtttattt ctaagttcca tcttttttag  87900
agaaaaggca aattaagaaa agtttagaga gaggtactag tatatttatg aacttgtata  87960
gatgataagc aaaacggact ttaatatgta gaattccaga atcaacaggt tgccagcatc  88020
catgtttttg aagatttgct taagaacaca accaaaaatg gaatgggcag tctctaatta  88080
caagcagaag gctacaaaat cattttagct gcataataca gttttggttc taaagtcagc  88140
acgtaagagg aaaattcctt aggaaaatac aacattgaaa accattgtgt catgtaatat  88200
gaaatgcaat aattaattt tcctccagta atagaaagat cactgtttca ttggtttata  88260
aaaatatatc tttatcatta aatgtggcaa aatgttaaga cttggtgaat attggtgaaa  88320
agtatatatc cattgtacaa ttcttttccaa ttttttttga gattgaaaat ttttaaaaca  88380
acaaattatc ttttaaacag ctaataatca ctagacctgc actctttgtg gtgagactat  88440
gaaaaatgtt agagacctag taagagaagc agattcacat ttctgtcttc ttcttcaagc  88500
caaacagtca tagagtggag tgggcagaat ggaactcact tttgaaagcc tagtgctttg  88560
tccaatctta ctgcaagcca gacaggaagg ttatagaaaa tgtttctgga tcagtcttct  88620
ctgagtcata tgaaattgtg gtttcagcca agatgacatt aggaattaga gacatgggac  88680
aaaaacttta agattgtaaa aaatttttga ctctagtagg aaacatgggt agaattgtaa  88740
tgacacttga ttgaattta aagatgcct gtataagatc ttaaaattag gaaaaaaatt  88800
atggcctaag caattaaagg cataggaggc atcttttgg gatgatggaa atatcctctc  88860
tcctgattgt gatagtagtt acatgaatat tcatttaaca aaaaccataa attatagact  88920
tagaaaacag taaatgttac tgtatgtgac accttaataa acgtgattat aaaaataaat  88980
cctaagcatc taaaaaaaa aaaaaaaaga agaagaagtg aaccagaacc acaccattct  89040
attttggaga cacttcaaaa gaaatgacct cattcttaat tttgttaaa gaagaatata  89100 acatgatttg aatatatta gctaggatat tttagtgcct gctagcactt gaagccgag  89160 ttcactgtga gcattctgac tatgaagtga gaagctaaga gaactgtatt tgatattcc  89220
```

```
tttgacagtt aaatcataac actgttcttc cccttcttta gccccagcat gagaccagat    89280
gtaagctctc ctccatccag ctcctcaaca gcaacaacag gaccacctcc caaactctgc    89340
ctggtgtgct ctgatgaagc ttcaggatgt cattatggag tcttaacttg tggaagctgt    89400
aaagttttct tcaaaagagc agtggaaggt agtgtgtgtt ttgaagagtt tattttttcct   89460 ctacttggtt ttcatttctc agggtggatt ttgaaatttc cattatatgc aaagcccatg    89520
aaaggctaaa tatcagttaa gaggggagag gagggtggct cctaggtcct ctaatgggca    89580
ggaaagtatt taaaacaaca atacaaaaag atctagaata aaatagaaaa gtacaagttg    89640
atgtctggga gtttggtcag ggagcataag gtaacactat aagaaagtgc tatcatatga    89700
aatgatggtg ttaagtttgg gcataacata atgttcattg tattagaaac atgggcttta    89760
acttccataa gctaataggt ttcaaagtca ccaactttac tggcctggca aaaatgagtc    89820
acagtgagaa ctgtgacagg aaaaaaaaaa gatattcatt tcatttctta ttcatttttt    89880
ttttctatta agccagggca ctgtgctaag tggtataaat accaataaga cctgatcctt    89940
accctctggg aagtcacact ccactgaagt gaaagatgag ttaacaatga caaggtacag    90000
agattataat atagatgagg gagagagaaa ctcggcctga ggaggtcagg aaaggtattt    90060
tagagaaact gatttcacta tataaatgtt gtattaacac aaatcttact ttgttatgga    90120
ttcagactgc tgacagggca acagcattat ctccctaaag aatgagaaat tcattccata    90180
gcaaatttat tagaagagag tctaaaatgt cctaatacta ccagtgactc ctctaggaaa    90240
aaaattgtca tataatttag ttatttctaa agcagtttga aagtagcttg gcctaaagct    90300
ctgattatat taatttttta agaaacaat tattcattca ctgtatgagg attattatta    90360
tttgtctcat gttgtgtttg catatccatg agagttagat gagtcatttt cttttgtttt    90420 acttttttaat acattagcaa attataaaat tactcatatt acaccacaaa gattacaagg    90480
atggcagctt tggccagtgt agtagtccca cctattgatt agagtcaaaa gtaaagccca    90540
gccctgcttt gtgcattgct cctaataaag tggatgttac ttaacacata cgcagaagac    90600
agaagcgtct tcgtgtcctc actttactcc tcactttctt aactgcttaa gtatttccac    90660
gatataaatg cagtgataat aataatacgg acagtccctg acttaacgat ttttcaactt    90720
ttatgatggt gggaaagtga tacgcattca gtatggctcc tcgacttaca atggggttgc    90780
ctccagataa acccattgtg aattgaaaat atcttacact tagcactcca ttcttaatac    90840
ctgctagaat tatagattat ccctcaaaat tggcatagta taatatgggt atcagcaagt    90900
tgttgcactt tattcagagc tttacactag gcaggggtgg gctttacttt tgactctaat    90960
caataggtgg gactactaca ctagccaaag ctggcatcct tgtggtctct gtggagtaac    91020
gtgagtagca ttataattta catcccccat aacaaatgat ccaagagagt atgtgatcaa    91080
tgcagcagaa ctattgtctt ttattatctg atttcacatg taacatgcca tcacttctgc    91140 catatttttat tggccacaca gaccaatctt ggtaaaggac ggaaagggac tgcacaagac    91200
catgcattca aggaggcaga gatcactggg ggccatcttg ggaggctggc taccacaccc    91260
accataaata gaaaaccaga attatttgcc aaaaatagac tttaaccaca aaatgaata    91320 ccatataaac aaaacaaagt cacaaaattt cagctgactt gaagactcat ctttctatta    91380
gttagaaagg gaatttacca agtagtagaa gacacaggaa ctccaaaata agatatctca    91440
ttgtcttatc agaaggggttg acaggaaaat gggctgggca ctgtggctca aggaaaatgg    91500
gctgtgcact gtggctcaca cctattatcc cagcaatttg ggaggccaag atgggaggat    91560
```

```
tgcttgaggc ctggagtttg agaccagcct gagcaacata acgagacccc gtctctacag    91620
gaaaaaaaaa aaaaaaaaaa acgttatcca ggcatcgcac ctgtagtctc agctactcag    91680
gaagctaaag caggagattc aggctgcaaa gagctatgac acaccactgt actccagcct    91740
aggcaacgta gcaagaactt gtctaaaaat aaataaataa atgagtcaag gaatgaatga    91800
atggattgac aggaaatgac tattagttgt acgtggccat gtgttatgaa atagtgaata    91860
ctagttaaaa ctcctcattt tatagataag aacagatag atagacttgt ccaacttcat    91920
gctaataacc acaaagggct atttttaact tatgaaggta cattgcctct gatcctatag    91980
ctcagagtct tagctgtgca caagacatac ctgggataaa gaaatcaaga ttggcgtaat    92040
gtgcacatcc tgacatttca gttggatata aacaaaactt tggaattttt catttttagc    92100
agtgggtgat ttttttttctt tttttcttcc agtaactgta ggacagtgat ttagagattc    92160
cttatagggt ataacttttt tgtattataa ccacttcatc aatagatgta tctgttgatc    92220
gtacttttga tttatagggg atagaattgg gttagtgctt ccattttctg tccaagtaaa    92280
gaagctagga tatttataga gtacaaaaag aaattgaaac agctggtaca gatatttggc    92340
attggagagc agctctgaac aaaggtgaat tatagtctag tggtcaattt tgtggcctat    92400
tctttacaaa gaattgaacc tgatacagtt aaccatctac cccaaactat tatttgttta    92460
aaacacaatc tattggctgg gcgtggtggc tcatgcctgt aatcccagca catcgggagg    92520
ccgaggcggg tggatcacga ggtcctgaga tcgagacaat cctagccaac atggtgaaac    92580
cctgtctcta ctaaaaatat aaaaattagc caggcgtggt ggcgtgcacc tgtaatccca    92640
gctactcggg agtctgagcc aggagaattg cttgaacctg ggaggcagag gttgcagtga    92700
ggtcatgcca ctacactact acactcccag cctgggcgac agagcgagac tccatctcaa    92760
aaaaataaaa ataaaaaaac ataatctatc aaactgtgta aaacacagtt tatcaaaaaa    92820
gtagttaccc ttggtgggta ctggctggaa ttgggcagaa agggggcctg ttgggtact    92880 gttctgtttc ttgatctgag agctgattac ataaaggttc ttggtttgta aaaatttatt    92940
aaatggttca ctgatttgtg tactttttttt atatgtgaat actgcaataa ggtttttat    93000 tgcactgttt tcagtttgtt gaacagaaaa agggagactc ttttgttgt ttttgacctc    93060 tcgacctcat aatggcaatg taggcaagaa cattccctca aggcaatacc tgtgggtgtc    93120
ttggttatat tccaccggaa acaaagacag aggctgtcct tataaaatat gtttgaagac    93180
ctgtgaaact ttaatagtgc ctttttattcc atataggaca gcacaattac ctatgtgctg    93240
gaaggaatga ttgcatcatc gataaaattc gaagaaaaaa ctgcccagca tgccgctatc    93300
gaaaatgtct tcaggctgga atgaacctgg aaggtaatat aaatatctga aagcaattgt    93360
ttgtctctgt agcttataaa aatttatcat tttactttttg aagatacacg taagcagatg    93420
taattaatgt agtcagttca gtatatatat gcttgactag cataatgtta ctgcccaata    93480
aaaatgggaa attttttttca tgaatatgtc atattgtttg tttatccacc agttcttctt    93540
acacacactg aattcagtac agccagacta tatacaaaga aaggaaatta tgtaataatg    93600
aaacttacac aacatgcagc aactttatta ttcttactcc ttttttcagc ctcaaaacta    93660
ttccctaggg ttggaaatgt ttctgtatca gacatattta catgtccatt tttctgtttg    93720
ccttttaaaa gcatacccttt tacttggaga tctgtgtttt attacagatc ttcaagcggg    93780
gggtggtggg aaaaaaaaaa cctcaaggaa gaactggatg ggttttgttt tggttttcaa    93840
gtaaagaaga aacctgggcc gggtgcagtg gctcacgcct gtaatcccg aagtttgtga    93900 gaatccttct gtctagtttt tatgtgaaga tattacctttt tccaccgtag gcctcaaagc    93960
```

```
gctccaaata tccacttgca gattctataa aatgagtgtt tgaaaaactg ctcaatcaaa    94020
agaaacgttc aactccatga cctgaatgca cacaacagtg agaagtttct gagaaagttt    94080
cttggtctcc ccgcactttg ggagaccaag gcaggcggat cacgaggtca agagatcaag    94140
atcatcctgg ctaacatggt gaaaccctgt ctctgctaaa aacacaaaaa ttagcggagc    94200
gtggtggtgt cacctgtagt cccagctact caggaggctg aggcaggaga tcacttgaa     94260 cccgggaggc agaggttgca gtgagccgag atcacaccac tgtactccag cttggcgaca    94320
gagcaagact ccgtcttgga aaaaaaaaa aaaaagaaa cctgaaacta gttataagtt      94380
agagtttcat atccctgttt atataacaag ttgtataatt aacactgatc tcagcattaa    94440
aaaattttcc tctgaaaaaa gtttggaatt ctgctgtggt tgaaattgca agttctgtga    94500
aggtagtggt gatctcataa cacatatgct tagtatttat tgtgaaatta gcacttttat    94560
tcaacaaata tgcaccaaca aggcagtcac taggtataaa atgaataaaa tagtgcctgt    94620
attcaagtag tttatctgct agttaggttg cagagtcagt cacaaaatag catggcacac    94680
catagagggc atagggccac aggaacaaga ggaaggtcac ctaattctgt cttggaagtc    94740
aaggaagaag taacattgaa ttttaaatct ataagctgag taggaattag atagatgaaa    94800
aataagggca gagacatgat cagatttgta ttttacaaag actaatctta catggagaga    94860
ccaattaagt gaatatggca gtcctccaga taagagatgg cagtactgag agagaatgga    94920
aaccatgtgg ttccttttat gattatgatg attattatta ttttagagac agagtctaac    94980
tcttgtcacc caggctggag tgcagtgaca tgaacatggc tcactgcagc cttgaactcc    95040
tagactcaag ccatcttccc acccagtagg gctacggatg tacactacca tgcccagctg    95100
attttttttt aattttttgtt ttaattttttt gtagagacaa aggggtcttg ctatgttccc   95160
aggctggtgt ctaactcctg gccttaagtg atcctcccaa cgtggcctcc caaagtgctg    95220
gtattacagg tgtgagccac tgcaactgac ctatgtggtt cttttgatag gagagactaa    95280
ttgttggtgc tatctagcac acactgtgtg tagacatctt gttaaataga aaatagattt    95340
atgggtatga ctatgaagag tctaattccc caaaccacac acacaactct atctacgttt    95400
gaccaggcta tttaaactta actgcagagt gtcagcatgt taaacattga tttacataaa    95460
atgatagctg cccactttct tgtaaatgtt ataaaaactg tagagattaa ctaaaaaatg    95520
cacacagaag tttgctttca gttccacaag ggtagtttat ttttgttata aaacagtat     95580 tccccacttt cttagatacc agatctctgc ccagatttta cccagtttca tcttgctgct    95640
ctctaatctc ctatgtatgt aatatacttt gaccatttaa atatgtatta agacacttga    95700 gttttagtg cccttttggtt tattttctcc ggtcccaatt atctctaatc ttcattttt     95760 cattttacct attttatatt tcgaaatagg ttttgaatga agctcaaagg acaaacccaa    95820
ataaaattct gtcgtatctc taatatattg tggttgctta cccagtaaca tttttaggtg    95880
cttttctgaa tacatataaa gtttaagatc tttggagttt taagtatata atgttttct     95940 gggcaatttc tccctatcca aactatgagg gccttctttc atcaaaagaa aaagatata    96000 tcaactacaa agtaatgatt tgatggact aggctacgaa atcgtccat ttttcctcc       96060 ttcttacagt ttaatagcaa ttgcagtgcc ctttgccctt actgtactag aagacgaccc    96120
caggcagtga ctgacatctg atttttctat taattatacc atcactgcca tttccagttg    96180 aatctttgt tggacatcag aaattttct tacatgaata aaatttaagc atacggttgg      96240
gcgcggtggc tcatgcctgt aatcccagca ctttgggagg cctaggcagg tggatcacga    96300
```

```
ggtcaggaga tcgagactat cctggctaac acggtgaaac cccgtctcta ctaaaaatac   96360
aaaaaattag ccaggcgtgg tggcgggcgc ctgtagtccc agctactcgg gaggctgagg   96420
caggagaatg gcatcagccc aggagttgga gcttgcagtg agccaagatc gcgccactgc   96480
actccagcct gggcgacaga gcgagactcc gtctcaaaaa aaaaaaaaaa aaaaaaaaa   96540 aaaaaaaaaa aaaatttaa gcatacaatt taggctgcag tttctcaaaa tattgtatta   96600
aaaataacca attatatgct tttatagtca gtataacgta tccagttagt gtagaaattg   96660
gcatttgttg aaaactacta catgttagtc tttgatatac attcttctac tttttggacc   96720
ctgattatta aaaacacctt tgaatagggc catgatttac tttatatcca tttttatact   96780
acatagtgga agaaaattct gatttgttat ttcctactat gatatgtacc gtgtggcaca   96840
tatcatataa atgatccaat tctacttgta gatgaattga agaaaggct taaaaagtt    96900 cttagggttt gtgtgtgtgg tttcactgta aactatcat ttttgtattg aactaacctc    96960
agtatacata aaatctttat ttggcctggt atgtacgtat gccaggaatc tttggcagac   97020
cctaacactt acaatacaga tgagccatgt gtttcacact ttttttttaa caaccttcag   97080
aaatattctc ttgttcatca gagtgcttcc cctaagccaa gcagtttcga tgatagcccc   97140
agaataactt tgcccaagtc tctccataaa tgtaacttag gactccaagt ggtgtatttt   97200
tatactcttg ccccataccca agtaaatctc aagatttatt ttaagggagt ggccttcact   97260
gcttaaaggg cctagcattt aagaacagat aagatttta atggtgatcc taaatgtttt   97320
tttttaaaaa acttgcttgt ttttctcttg aaactaaatg tttttattca cttcatttta   97380
agatatattg taatcaatcc aaagtatggc tttattttta gtataaacag tcaaatgaag   97440
cttagtcttg tggcattgtc agatttataa ccaaatatta ctgaaactaa tttttttaag   97500
ttcaaaaacc caatctagta gtttctctct tattttcaac ttttatttta gattctaggg   97560
gtacatgtac aggtttgtta ctaagataca ttgtgtgatg ccggtgtttg gagtatgatt   97620
gaacctttca tctaggaagt aagcacagta cctaacaggt gcttttaac ctgtgcctcc     97680 cttcctctat ccccctctt gtatttccca gtgtctgttc ccatctttat gtctatgtgt    97740
actcaatgtt tagctcccat ttataaatga gaacatggta tttgttttc tgcattagtt    97800 catgtaggat actggccgcc tgctacatcc atgttgctgc aaaggacgtg atttcattct   97860
ttttgtggcc acatagtatt ccatggcata taaataccac attttctta tccagtccac    97920 tgttgatggg cacctgggtt ggttccatgt ctttgctatt gcaaaccatg ctgcagtgaa   97980
catatgggta catgtgtctt tttgatagaa tgatttattt ttctttgggt atattcccag   98040
caataggatt gctaggttga atggtagtta aactcttaat tctttgaaga atctccaaac   98100
ttctttccac agtggtgtca ttgtggtttt gacttgcatt tctctgatga ttaacaatca   98160 gcattttttcc atatgtttgt tggccacacg tatgtctttt tttgagaagt gtctgttcat   98220
gtcctttgcc cattttttaat gggttgtttt ttgcttgtta atttaagttc catataaact   98280
ctggatatta gggctttgtc agatgcatag tttgcaaata ttttctccca ttctgtagat   98340
tgtgatagtt tctcttgatt tgcagaaact ctttagttag gtcccattgt caattttttgt   98400 ttttgttgca gtttcttttg gggattagtc ataaattctt tcccaaggcc aatgtcgaga   98460
aggttatttc ctaggttttc ttctaggatt tttcatagttt gaggtcttac atttacatct   98520
ttaatccacc ttactaattt ttatatggca gtaggtaggg gtccagtttc attcttctgc   98580
acatggatag ccagttatcc cagcaccatt aatggaatag ggagtctttt ccctatggct   98640
tatttttatc aactttgtgt agattacatg gctgtaggtg tgtgtctta tttctggact   98700
```

```
ctattctgta ccattgtgtg tggttttttt ttaccagtac catgctgttt cggttactat    98760
agcctgtagt atagtttgat ttggggtaat gtgatgttgc caactttgtt cttttttgctt   98820 aggattgctt tggctatttg gggcattttt tggttccata ggaattttag aatgcttttt    98880
gctaattctg tgaaaaatga cattgtagtt tgataggaat agtgttgaat ctataaattg    98940
ctttgggtag tatgaccatt ttaactatac tgattctacc agtccatgag catggaatgt    99000 tattccatt  gtttgtgtca tctttgattt ctttcagcag tgttttgtag ttctccttgt    99060
aaaaatttta aactaactta gatgcattcc taggtatttt actcttttg tgactgttac     99120 aaatgggatt gcattcttga tttggctctc agcttgaaca ttactggtgt atagaaatgc    99180
tactgatttt tgtacattga ttttaaatcc tgaacctta ccaaagttgt ttatcagctc     99240
caggagcctt ttgacagagt cttcagggtt ttctaggtat agaatcataa gtgaaaagag   99300
atcgtttgat tatttatttt cctatttgga agccttttat ctctttctct tacctgattg    99360
ttctgactag gatttccagt actatgttaa attggaatgg tgacattggg catccttgtc    99420
ttattgcatt aaggggaatg cttccagctt tgcccatttt ggtatgatgt tggcctgttgg   99480 tttgtcatac agggctcttt attactttga ggtatgttcc ttcaatacct agtttggtga    99540 aggttttat  catgaagaga tgctggattt tatcgcaact ttttctgcat ctattgagat    99600
gatcattatt ttttttgtta tgtggtgaat cacatttatt gatttgcata tgttgaacga    99660
gccttgcatc ccagaaataa agcctacttg attgtggtga attaactttt tgatgtgcag    99720
ctggattcag tttgctagtg ttttgttgaa gattttttgta tctgtgttca tcagggatat   99780
tggcctgtag ttttgttgtt gttgttgttt ctctaccagg ttttggtatt agaatgatgt    99840
ttcccttgta gaataagtta gggatgaggc cctctttcta gattgctttt ttagaatagt    99900
tttagtagga ttagtaccag ctcttctttg tacatctggt agaatttggc tgtgaatcca    99960
tctggtcaag gcttttttt aattggtagg tttttatta ttgattcaat ttcagaactc     100020
gttattggtc tgttcagaat ttcagtttct tcctggttca atctaggcag gttgtgtgtt   100080
tccatttcca catacatact tactccaaat aatggcttta tatatacggg ggtcagctga   100140
aaacaaaaat gatactttca tagtaaactc caccgcccc cccacccaca tacacacaca    100200
cataaaccct agattttta  aagcctttgt tccaatttat ccatttcctc tagattgtct   100260
actttgtgtg catagaggtg cttgtaatag tgtgaagatc ttttttcactt ctgtggaatc   100320 tcttgtaatg tcatctttta catttttat tgtgcttatt tgggtcttca ctcttttttt    100380
ctttgttaat cttgctagtg gtctatcaat cttgtttatc ctttcaagta accaactttt   100440
ataaactagg ttttaagcta attaagattt ctctactttc attaagaagg aagtagtgtt   100500
accacagact catgaacact tctgtggagc tcctgtattg actgctaatc aactatatgc   100560
tccaatgggt caggaattta tataaagttg tattaactaa gttgctttaa aatagtgatt   100620
gcttaactaa atgattcagt tcagttaact ccttcctgaa gatattttga aaaattaatt   100680
agtattattt cttgctctag tcagtacagc acagttgggt tcaattgtac tttctgagct   100740
gtattgaaaa acatcagttt tctccattag aactatatat aagtagtgag aaattaatta   100800
caaactgagt catagaaaat gttttttttt aatcctccag cttgttactc tttcttcctt   100860
gttctaatgt ggagtaaaga aatatgcatt ccaaaccatt taaagttatg actaattgag   100920
gctgtcaaag tactgtttca gtgtattgat ttggcacatg tgtgttctct tttacattgt   100980
caacaaaagt acatttatg attttggatc aagatttcac tgagatactt ctggttgttt    101040
```

```
aaagagtttc tttatgtatt ggtgtctttc ctttttaaaa ttttatcact cctctattaa    101100
gttgtgatat ccaaatttaa aatattctaa aaacatgttc tcctgcaagt tgaggtaatg    101160
atagttgtta tgtggtactt actataatat atgccaggaa ctgttctaag cattttacat    101220
atttaattct cacaacaacc ctatgaggta gggactaata ttgtcctcat tttacagaag    101280
gggaaatgaa gagtcaggga gtaacttgca cagatatcca gctacaacat ggcagaacca    101340
ggacttaaat ccaaatatgc tgatttcagg tttctgccct ttagtcctat atcatactgt    101400
gcctccaaga gagcatggta aactaattag catggttcta tcatgattct gtttctattt    101460
tgaactatta ataaaaattt ttgcaattct cagttacccc atttagtata gaacacaata    101520
agaatggaac cattctattc taacattgta cattgagata tcgttcccac caccatatct    101580
gtcctccata gactatatgg tgtgtcattt taaggacaga ggatctaaaa atgatttta    101640 aaggtgattt acatttactc ttcccttgc aaaatggttt gcatccctaa taatttagac    101700
aagtacattt cttcgtgata taaattacat ttcttgcctt tccctggaat tctgagtact    101760
ttccctctga gagaacaatg taattcttat ttatttagtc actaaaataa cttcaggagt    101820
atgaataagt ctactaaaaa gtctacagga tccatgttgt agtttgagta gatggttcca    101880
taccaagtca aggtaaaaga taatttatat ataatatgaa aatggctgct ttaggtttat    101940
agagtaatca atataaatct tccttataaa agggaaattt cccacttata atttatgtaa    102000
tgtaaagttt ttcatttcat cttcccaaat gttttagtc ccacgcagta tttatgttag    102060
tacctatgta aaggtgaaaa gtgaatttt tctactggta gaactaatac tatttttagc    102120
atgtaatctg ctgtcatctt cctatcttta taagtggctt tgaacaagtg taaatagtgt    102180
aattctcttc attatatata ctaccatgat ttagattaat cttaaaccac agtttgtaat    102240
ccgttactcc aagcttagat tttttttttca gtttatagta agagtaattt gccttatata    102300
accaatgaaa ttgttgcatt tagagtgaaa gtgagataaa aaaataattt atagaagaat    102360
ttacaaaagt tatttactca gattgttta acataccgtt ataatacttt gtataaggaa    102420
taactctaat gaagtttctg gcctatttgt aggcaaaatt aattgggaat aggttcctct    102480
ggatcttttg ctttcagaaa aaaaaaagtt ttttctcctt ttccatgtca ctttatcata    102540
attgctaaat aaaatatttc tcccatctta atagttttag aaagtaaaaa tacttcttga    102600
ataaactgtg tagcgcagac cttcccatta cagttcattt ctatgtattt gtttaaatac    102660
ccacagctcg aaaacaaag aaaaaaataa aaggaattca gcaggccact acaggagtct    102720
cacaagaaac ctctgaaaat cctggtaaca aaacaatagt tcctgcaacg ttaccacaac    102780 tcaccectac cctggtgtca ctgttggagg ttattgaacc tgaagtgtta tatgcaggat    102840
atgatagctc tgttccagac tcaacttgga ggatcatgac tacgctcaac atgttaggag    102900
ggcggcaagt gattgcagca gtgaaatggg caaaggcaat accaggtaag atgcaaaaca    102960
taaaagagca actatataaa cctttgtgtt ttcttcagca aaaacacttt ggcttttata    103020
tcatcgtgag cccatggctt atcttgtttc tcttagttct ggggactatg aaggggagag    103080
tcaggtgaat acaggtgata gggagtttat aataaaacat ttacattact ccctgctttt    103140
caaatcatta tgcacaggat ggtaatttca cataggatga tgtaatatca gaattcaagt    103200
tacaagactc actcaaaact ccttttacac tgaagtttgg ggaaagaaaa tgttttagt    103260 taattccatt tgttttcctt cattgtgcca cttttaaaaa tcaggttgtt tgtaagattg    103320
gtaaacatca agtatgttga ttgtcaaaat ttgtactaaa gtagaatgat tttaaccctt    103380
cactaaatga aatgctacac attgaatgta attttaaaga taattttaaa taaaagttac    103440
```

```
cctattggaa tttggtgtgg aatggcagag gtcaatgtta gtgtcagctc tgactttaaa 103500
gacagggaat tgacaagcct gtgttcacgc aaatagttag ggagagagca agaaagtaac 103560
ctgacctcct gtcatccttg ttttattaag ggggaaagag gtgtgaatag cagggcaaat 103620
gttttgctta actcattgat taatacctca agccaagatt cttttctgtt ttttaaaatc 103680
aatacataat agttgtacat atttactgta catatttata tttaggggt acatgtaata 103740 atttaataaa agcatacaac gtgtaaggat caaatcagag taactgggat atccatcacc 103800
tcaaacattt gtttggggaa cattccaaat cttctctttt agctattttg aaatataaag 103860
taaattattg ttaactatag tcatcctgtt gtgctactga acactaaaac ttatttcttc 103920
taactgtatt tttgcacccg tcaaccattc ccgcttcatc cccatcacca ctatctttcc 103980
cggtcactgg taaccgccaa gccaagaatt ttggctattt tactatttag ttcatgttta 104040
cttaagcaga cagaggtgac aaaactggct ttttttttt tttttacat aaaagctat 104100 taaaaagcac ctaggggct gggtgcgatg gctcacgcct gtaatcccag cactttggga 104160
agcccaggtg ggtggatcag ttgaggtcag gagttcgaga ccagcctggc cagcatagca 104220
aaaccccatc tctactaaaa ttacaaaaat tagccgggca tggtggtatg aatctgtatt 104280
cctagctact tgggaggctg gcactgagaa tcacttgaac ccgggaggcg gaggttgcag 104340
tgagccgaga tggcaccatt gcactccagc ctgggtgaca gagcaagact ttgtctcaat 104400
taaaaaaaaa aaaaaaaaa aaacacaag agggtttgtg agtcttaaag tgtcagatga 104460
cagaagaaaa ctgtgtctac ctagtattta atttccattt tctgttaggg gtgcccttgt 104520
tttgacaggg ctaattgatc tcattgctcc ttggcaattc ccacagagat gatcttctga 104580
agagtgttgc ctcatacctt tatttctctt aattcaggtt tcaggaactt acacctggat 104640
gaccaaatga ccctactgca gtactcctgg atgtttctta tggcatttgc tctggggtgg 104700
agatcatata gacaatcaag tgcaaacctg ctgtgttttg ctcctgatct gattattaat 104760
gagtaagttg tatgtgtgtc attttccctg tattcatagg gtatctttaa ccagctgatg 104820
ttttcctgat tgactgctat tgtgataatt caggactgaa acaatcctac taggtatcta 104880
ggatctaggc aaactggaaa tagagttatg agtgcttggg gcaggacaag tgtaatgtaa 104940
agcaaatgta catgtggcat tattactgtc ccaggacatg tttgaggata tttaacagca 105000
tatctgaggt tagtaaagtc tgtcgcaagc aacaaggaat cttactgtga tatcatttac 105060
ataaccctat tccagaaaga aaaggagca tggtaaaact catgtggatt cagtggggac 105120
aattgtagat gaggatatct aggctgatgg ggtgggacat atggacccag acacaagagg 105180
tatctctttg catggcaagg ctcacccagt gtctgtggtt taagaatatg ggaacaaatt 105240
tgttttgttt aactgagaga agaccaagcc tttaagattt tataaatcag ctattctctt 105300
atcctctaag cttattcctg tgtctgcgaa atacttcagg tgtccatttc ccttacctc 105360 attgcagttg tttcctcact cgttttctcc ctccagtgta acgttcatca tgttggctaa 105420
tgtttgcttc ctcaagcaca gtctgactgc atcacatatc tccccagtac acagattgtc 105480
ttcagtatct tcccactgac cctccagtac atattctgca tgatttcaga cttttccagaa 105540 tctgacctca cttcctctcc cattgttttc cttcacacac tcttcattcc catccatcct 105600
ttccagcata ctcttagact cttggtgttc acatcaccag atacacagca gagaagtcac 105660
atcctagtta ctctcacttt ctaccttgta ttactacttt tcgtaccct agcttattgc 105720 tattagtaca atgtaaacag ggagttcaca cacacatacc cctggtctaa gaagaataaa 105780
```

```
aaatgaagga gatttctgtt tgtatagaaa acagaagtca ccttgacttt tattgccaaa   105840
aagaggactg ttcaaactac tgcatcacaa tgtaacaaga ttaggtagtt ggatccaatt   105900
ttaaattaac tggtaaatat atttagtttc tggggaaact gaagacatta ttactcatca   105960
taatcctacc atgctgttta aaaaatacca tgttggcagt atttgttttt tagtcacttt   106020
ctaatatgta atttgaaggc atttaagtgg aattaaaagc ataaacagat ttgtatgaaa   106080
caccaactta tcctggttta taaaactaac ctaatttagg gttttttatta ttagggcatt   106140 cagatttagc tttaagcagt cacagcaaaa tctaatcatg ccacatacat tccttacata   106200
aagtgggatt tataatttt tttcctcaac agatttacat tagtttcatt ttcattaagg   106260
gatatgtact tcctattctt gtgttctcat gctgctgcct aaaagatggg cagtcctcca   106320
cctttttctt ttcttttttt tttttttttt ttttgagacg agtcttactc tgtcacccag   106380
gctcaagtgc agtggtgtga tcttggctca tgcaacctc tgcctccagg gttcaagtga   106440
ttctctgcct cagcctcccg aatagctggg attacaggcg cactccacca cacttggcta   106500
attttttgta tttttagtag agacgggtt ttgccatatt ggccaggctg gtcttgaact   106560
cctgacctca gtgatccac ccactttggc ctcccaaagt gctgggatta caggtgtgag   106620
ccaccgcacc cagccctcca ccctttttc ttagcccact atgtttccat actgctctgg   106680
tgtctgtgac aggcagatat tgcatatcag aaagtatgca ttcaagttct gaccctctat   106740
agagctgtca aacagtctct catggttgcc cttaggtcag aacgttgtgg gggaaaaaaa   106800
aattgttgtt gtttttacag ccaacaagaa tgagttttta cttattctac tacactataa   106860
ctttgttgaa attttcagtt atatgagtat aaccatgtac aagaaactaa aggaaaaaaa   106920
ggtgcctccc agaaaaggag tgctttacct actattaagg actagggagg tgcctcttcg   106980
gtaagagcag atttaaatt tgaagagcct ctgatcactt tggcagcata taagtcatgt   107040
ctaatttatt ttatataaag gaataaacca catattcagt agagaaaat aataacctt   107100 ctgttgttaa gtccaagacg actttctgtc agaaacttaa aaaaaaaaa aaatcttgaa   107160 gcatttaaaa agctgtgaac tgggcccagt ttcaggctct tagtgtcatt tcacaagtca   107220
ggaaacttta gagacctatt tgaaaatcat aggtatgtaa tgacttcaga atcataagca   107280
agaattggtt tagtacctt agtttaaaga atattaaggc atatgcctgt cagaggcaga   107340
ttttgagcat cagaagtcta gaatcaagtt ctaggtctcg ccctctgcat aactgtgaac   107400
agtgtcacac atttttgtct ttaggatgga ctgctgtgaa aaaatttacc tttaaaaatc   107460
aagtgtgtag gacctaaaac tgtcgtctaa ttgaccgtat tcaaatgata aaccttgatt   107520
taaatgagca actagtaata agttctataa gaattctaac actttaatta aataataaaa   107580
taatacatgg catgcatgat agaaaataat atctccactg ttacattaga ttattcatta   107640
gtctatttaa acagccaaga tgcaggaagt ttaaggaaag ttctccaaaa ttctgatttt   107700
atagggaatt agcaataata ttattgcagt agttgttttt ctttatgagt tcatagtttt   107760
gcaaaacaaa acaaaaatgt gcttttggg gggaagtagc agtatttcta actaatacc   107820 tgctatttat ctttcacagg cagagaatga ctctaccctg catgtacgac caatgtaaac   107880
acatgctgta tgtttcctct gagttacaca ggcttcaggt atcttatgaa gagtatctct   107940
gtatgaaaac cttactgctt ctctcttcag gttggtagaa caccttttca ccttatgtca   108000
aaagcatgaa atatgaaggc ctagaaacaa aggttaattt atatacatag tactaataat   108060
tataccaagt ctactattat ttcctactag tcagatgatt tttatgaatg taaaatatta   108120
gaaaggcaca gtaagtgaca ccaagattaa taagacaaat aggtatggca gaaacagaga   108180
```

```
ggtatatgag ctgcataggg atctctgttg ataagaatct gtgtagactt ttttctcctt 108240
ccttcctttg atctttgatc atgggaagac atggaaaaag aaagctaact acagtgattt 108300
tgtccactac actgttattt ggttaaaaat tttagtttcc taatgagtat tagcatgtat 108360
gagaaattat gggagaaaaa ggcgcatcct agaaaaggtg tgcttaatta ctattgggga 108420
ttggttaaca tagcatggga gctggattgt cagagattca ttatctagaa aatggcaaca 108480
agagtttata aaacgaactt ctgtgagatt acttttttagc tagcaaagac aaagatgtcc 108540
ttcagtaggt gaagtgataa actatgatac atccagatga tggaatacta ttgaggacta 108600
aaaagaaata agctgtcaag ccatgaaaac acatggaggg acgttaaatg catattacta 108660
agtgaaaaaa gctaatctga aagggctaca tactgtgtga ttctaactat ataacattcc 108720
ataaaaggca aaactgtgaa gacagcaaaa aaaaatcagc ggttgccagg gtttagaagg 108780
aagggaggga taaatgtgca gagcacagag gattttttagg gcagtgaaaa tacttcgtat 108840
gatactacaa tggtggaaac atgtcattat acatttatcc aaacccaaag aatgtccacc 108900
accaagagtg aaccctcaac tatggacttt gggtgatgat gtgtgggaca ggagtgtatat 108960 gaaaaatctc tgtaccttcc tcccaatttt gctgtgaact taaaactgct ctaaaaaaag 109020
tcttttttaa aaaagctctc atgaactagt tggtattata aaccttaggc catttcaagt 109080
aaaaattaca tatcaatgtt tattaaatac tgagttaata gctgaatacc tctttcatat 109140
acaaataagt acatttgcaa ttttttaaaa agtcttaatt ccattagtaa ctgtggtttc 109200
atagttgcca aataactgta agctatggat gttgcacaag actgtgatt tattaatca 109260 tttcatatct atttaaacat ttccaaagcg cacattcatc ttaatgtttt cacactattt 109320
ttgctcaaca aaaagttatt ttatgttaat ggatataaga agtattaata atatttcagt 109380
caaggcaaga gaacccgata aagatcattg ctagagacgt ttaatgttac ctgtagcggt 109440
acacttgtta aagaagtgat taagcagtta cataaaattc tgatcatagc tttgattgat 109500
accatgaagg tataattcag tgcctggata ctaacaactt tacttgttta aaaaaaaaaa 109560 aaaagaatg gtttcaattg tatacatccc agactaattg agctatatga ttttttttcat 109620 tgtaaataat atcacgagtt cttcttgtta aaaaataata gaatcataag gatggaaata 109680
tataccttaa gatatagact tctactatga tagactactg gaataggtat ataacctccc 109740
accaaaaatg ctagactaaa aaaattaaga actaagtgaa ggcaggaacc tacagagata 109800
agtggaactc aagccaactt gctctttgac ggcatttgta gaacctggta aattagtaag 109860
tttagtaagt tggggttttt ttaagtttat aatctttttt aaaatgattt caataggttt 109920
ttggggaaca ggtagtggta ggttacatga ataagttctt tagtggtgat ttctgggatt 109980
ttggtgcacc catcacccga gcagtgtaca ctgtacccaa tgtgtagtct ttcatccctc 110040
atcccctccc caaccctagt ccacaaagtc cataatatca ttctcatgcc tttgcatctt 110100
catagtttag ctcccactta gaagtgagaa catgcaatat ttggtttccc attcctgggt 110160
tacttcactt acaataatgg tttccagttc catccaggtt gctgcaaatg ccattatttt 110220
gttccttttt gtggctgagt agtattccat ggtatatata taccacattt tctttatcca 110280
ctcgttgatt gatgggcatt tggactggtt ctgtatattt agtaagttta aaacaaggg 110340 atggaaatat aaatgcagtt gaaaaggcag tggatggatc taaaagcaga agaatacaat 110400 tgttttttaat gattgtgtat atgtttgtgt atataaacca caagggaaat ctgtaggtac 110460
tgaaaatcac aacaggaaaa tggcaacaaa gctatagaaa ctggaaaagc aatgactttt 110520
```

```
cttagatccc tcagagaatg gaggtcatag gacaaaccac cacttcaaaa tctagaagaa    110580
tagacaaata cagagaaaca gccaagatca gcttactggg aaaagatgcc actgaagcca    110640
ggaagactat ggcaatttgg gaaaagatgc cactgaagcc aggaagacta tggcaatttt    110700
gatgaattgc tggaggctga gtgaggacta gcttcagagt taaaaactcc cagggaccca    110760
gtcttagtgg gggtttcctg caatttcttg ggtttacccc acaaaatttc taacttccag    110820
aaactccaca aggttcttat ggtgaagatg caagaaaaat tccctccttt ttctggtagg    110880
agtagaggga aggtaaaatt tggaaatacg tagcagagtg ttcacaacaa aaggcctgcc    110940
ctgtaaggaa aactaattca acaggccctt atgtgacctg ggggaaaggc aaatagagga    111000
ttctagccct tccttagcct tcttgtctca tttctgaaag tcacagccca gggattcaga    111060
cccactaaaa aaaactgaga tttaatcata aagattaaaa aacaattccc ctccccctcc    111120
ccaacacctt accaccatat aaacagggct ccaggataaa ataacagtgg attacaactg    111180
agagagctgc aagacacaag ctgtttaagg agctcttagg aaacccaaaa acaacagaag    111240
aaaaagtaaa taaaaacaag gaaactagag gaaactgaag cctccagtac ctacaattat    111300
ggcaaacatt aaatacagcc cagctcctag ccagattagc atgaaacctc acactaaaag    111360
tctaattact tcagttttga tatatcaatc atgtccagct ttcagcaaaa aaactacaag    111420
gcatgctaaa aggcaagaaa aacccacggt ctgaagagac aaaacaagca tcagaagcag    111480
tcctcagata tgacacaaat atttcaatta tcagataggg aatttacaat acctatgatt    111540
agtaggttaa aggctccaat ggaaaaaagt agacaacatg caagaagtga tgtacgcaga    111600
gagatggaaa ctctaaaaat aaatgctaag gaatgctgta aggaaatgca gaatgatgtt    111660
gatgggctca tcagtagact gagcacagcc aagcaaagag tcagtgagct tgaagataga    111720
taggtcaaag gaaattcccc caaactcaaa tgcaatataa acatagtaga cattaatcca    111780
gctgtatcag taattacttt aaatttgaat gctctaagta caccaatcag ctatttttt    111840 aactaggagg tgaaaataaa gtttgccacc agatgctcac taaaaaatta ttagaggata    111900
tatcccagcc aggcgtggtg gctcacaccg gtaatcccaa cactttggga ggctgaggca    111960
ggcagatcac agagtcaaga gatcaagacc atcctggctt acgtggtaaa accccatctc    112020
tactagaaat acaaaactta gctgggggtg gtggtgcgcg cctgtagtcc cagctactca    112080
ggaggctgag gcaggagaat cacttgaacc tgggacgtag aggttgcaga gagccaagat    112140
agcaccactg cactccagcc tagtgacaga gggagactcc atcttagaaa aaaataata    112200 aaagtaatcc catctttaag aaggactgaa gaataacaaa agtggtaaat aatatagata    112260
catttaaact gacatttact atgtatataa aataacaaca gtaacaattt ccttgagggc    112320
taaaaagtag aactaaagta agtttcaagg atgacaacta gaaataggt atgcagggta    112380 tgcaaagtac caaccattg ggggaagaga atacctaaga aaaacaatcc aaagaatga    112440 aagacatgag aggagggaga aaaaaatgca taaacaaggg catgataaca ggaagtaaca    112500
gataaggtac attagtacag ctaaattcaa acacatcagt agtttagttt cattaaatat    112560
agagatgggg ccaggtgtag tggctcacac ctataatccc agcactttgg gaggctgtgg    112620
gcagatcact tgaggtcagg agttcgagac cagcctgacc aacatggcga acccccgact    112680
ctactaaaac tataaaaagc cgggtgtggt ggtgcatgcc tgttatccta gctactcggg    112740
aggctgaggc acaagaatca tttgaacctg ggagatggag gttgcagtga gccaagatcg    112800
tgccactctt ctccaaactg ggtgacagag ggacactgtc tcaaaaataa aataaatgta    112860
gagatggact gaatgctcca agctaatctg acaggatttt agaaataatc caaatttatg    112920
```

-continued

```
ctatttaaaa aaagctatat ctgaataaag atattgaaag gctgaagtaa aaggatctac 112980
tttgcatagt ataacccaag acatggccaa cttttttctgt aaagggccag atggtaaatg 113040
ttgttagctt tgcacagtct ctgtcacagc tactaaactc tgcccttgtg gcaggaacat 113100
agtcattgac ggtactcaaa tagaacaggc atggctgtgt tccaataaaa ctttatttac 113160
aaatacaggc tgcaagtagg atttggccca taggccaaag tttgctggcc cctatattga 113220
ccaaaacaaa accgaaggag ctacattatt accaagcaaa atagatgtta aggcaaaata 113280
ctccttaaag catttgttca ggaaaaataa ttgtaaatat atagtttcaa attacataat 113340
acaaaaattc atagaacaag aatacttaga taaatctagt aaaaataatg agattttact 113400
ataccttcct tacaaattaa gcagacaaaa aaataaggat atggatgtac atttcatctc 113460
tcttgggtca atactgaggt gtgagatcac tgggacatag gttgagtgtg tgtttaaatt 113520
tatttttaaa attgccaaac ttttccgcaa tgttaacat ttaccagaaa tgtatgagac 113580
ttcttaagat ccattctata tcctcctcag tacttggtac tgtcagcctc tttcatcgta 113640
ggtatactga tgattaaaaa tattaagcat cttttcatgg gcttattggc cacctatatt 113700
tcttatttgg tattgtgcct cttttaatct tttgcccatt ttttaactgg gttttaagaa 113760
ttgttcaaat attctcaatg tggccctttg ttaaatatat gttttgcatg ttttctttaa 113820
gtggattaca tttacagttt tcttaaaaaa atgtagagat gagcaaaagt gtataatttt 113880
gaagaaagct tcgtgtcttt gtttactaag aaagttttgc ttaatccagg gttaaaaga 113940 ttttctacta tttgtttct tatagaaatt ctgtagtttc agctcacatg cttaagtata 114000
tgatgcaagg taaggacaa ggttcatttt cttccccaaa atccatatct ggttgctcca 114060
gaacttgact ctcttttccc tattgagtta cttggcaatt ttgtagaaaa tcagttgttt 114120
gtatatgtgt gggtctactt tcagactctt tttcttaccc aacgatctgt atttcttacc 114180
caatgatctg tatgcctata ttcatattga taacaccctg tcttgattac tgttgcatta 114240
cagtaaatct tgaaatttgg taatatgaat tctccaaatc tgttgttctt ttccaaactg 114300
ttgttttgga tattctagtt tccttgcatt tccacttcct tttttttttt ttttttgag 114360 atggagtctc actattgttg cccaggctgg agtgcagtgg catgatcttg gctcatcgca 114420
gcctcagcct ccccagcagt gggattgcag gcacccacca tcatgcttgg ctaatttttg 114480 tattttagt agagacgggg tttcgccatg ttggccaggc tggtctcaaa ccctgacctc 114540
aggtgatcca cccacctcgg cctcccaaag tgctgggatt acaggcatga gccactgtgc 114600
ctggtcttcc acgtattttt taattagctt gacaatctct accaaaaagt cttttgggggc 114660 tgggtgtggt agttcatgcc tgtaattcca ccactttgag aggccaaggc aggcagatcg 114720
cttaagccca ggagtttgag accagcctgg gcaaaatgtc gaaaccctgt cactacacaa 114780
aatagaaaaa attagccagg catggtagct tgtgcctgta gtcccagcta cccaggaggc 114840
tgaggaggga ggtcaaggct gcagtgagcc atgatcatgc cagtgcactc tagcctgggc 114900
aacagagtga gactctgtct caaaaacaca gtctgataga atttttatta ggatagcctt 114960
gaatctatag atccatttga aaataattaa catcttaaat ttccaatttc tggccgggcg 115020
ctatggctca cgcctgtaat tccagcacgt gggaggccg aggtgggcag atcatcaagt 115080
caggagttcg agaccagcct gaccaacatg gtgaaaccct gtctctacta aaaatacaaa 115140
aaaattagcc aggcgtggtg gcacatgcct gtagtcccag ctactcagga ggctgaggca 115200
ggagaatcgc ttgaatctgg gaggcagagg ttgcagtaag ccgagattgt gccactgtac 115260
```

```
tccagcctgg gcaacagagt gaggctccgt ctccaaaaaa aaaaaaaaaa attccagttg   115320
ttgagaaaga ataggaattc cagctttgga ggagtgggga gaccatcaaa tcctctttcc   115380
aaaaatacta ctaaaatact actgagcaga gtatagttcc acaaatagtc ttctgtaaag   115440
agactcacag tacatatttg tctttgtagg ccatatagtc cctgttgcaa tttctcaatt   115500
ctacagctat aacaggaaag cagctatata cagtatgtga atgcttgtgt tctaatacaa   115560
atttatttgc aaaatcagga aaatggcttg aaatggttta agatctagtt ttctgactag   115620
atcatggtat ataatctttt ccatatatat tttgaatttg gtttgctaat attttgctga   115680 tcattttat atctctcttt atgaaggatg ctgatctaca actttctttt cttgtgatat   115740
ctttttctgg ctttgctacc agggtagtac tagcctctta aaatgagttg agaagtattt   115800
tctgttttct taaagagttt atagagtatt gatcttattt attctttaaa tatttgatac   115860
atgttaccag tgaagccatc tgggtctgtg ttttctttca gggaagattt ttaattattt   115920
gcttatttgt tatatagatc tattcagaat ttatattttt ccttgacata gttttgtaat   115980
ttgtgtgttt ctatgaaatg agccattttg tctgagttgt ctaacttggg cataaagttg   116040
tttgtaatcc tttaagtttt gtaggatcca tagaggtgtc ccctccatta tagattttca   116100
taatttgtgc ctgatcatct tttttttcatg gtcagtctag ttaaaaattt atcaatttg   116160 ttggtcttta caaagaacca attttagtt tcattgaaat ttttagtttc attgattttc   116220 tcttttgtt tcctatgtca ttgattatta tttcttcttt tctgcttgct tttcatttaa   116280
tttgttcctc tttttctagt ttaaggtaga agcttccatt gttagttgaa gaccttattt   116340
tcttatatag atgtttaaag ctatacattt tttgtatatt ttcattcatt tcatttccta   116400
atgtccttca tgatttttt cattgaccca tgtgtatgtc ttaattttta tatttggg   116460 gattttccat atctcttcct attcattct aatttaattc cactgaggta ggaggtacat   116520
tgaaggactc taatattgaa tgactccaat aagtcttctg agactttttt aggcacttgc   116580
atatggtcta tcctgagtgt tccatgagtg cttgaaaaaa aacttactgt gctcttgtta   116640
agtagagttt tatgaacgtc agttaggtca agttgattga tagactaatt caagttttct   116700
gtatctttgc tgatttcttg tctagttgtt ctagatccta caactttgtc tacatccttg   116760 ccagagctttg gtatggtttt tttattatcg ctatcctaga gagtatgtag ttgacccttg   116820
tgacttgcca tgcatttaat gactgcccat gttcatagca gcattattca taatagcaaa   116880
aaaaactttt atcatatgct tttgtgcctc aagatcatat atttttcgtt tttagtcact   116940
aatatggtat aatggtataa tatactgttt aatttctgag taattgacta gcctttcatt   117000
ccggggataa atcctatttg gttatgtat agtatcctttt ttacatatag ctgaattcat   117060
tgtactaaaa ttttggtatt tttgcatcta aatccatgag ggatatattc tatagctttg   117120
gtgttatgat aatatggtat tattcttttc ttaaacgttt ggtaaaactc agcagtgaag   117180
ctgtcttggt ttgtttggag cctttttttgt agaaaggtt tcaagtacaa gttcatcaaa   117240
tgtttactga taatatgttt attcttgagt gagctttgtt ggtttacatc tttgaaggaa   117300
tttaactgtt tccttcaaat gttgaattta ttggtataa gttaagttat tcataatatt   117360
cccataatat ccttctaatg gctccagtat ctctagtgtt attccctttc attcccgaca   117420 ttggtatta atattcctt gctttttttt tttttttta atcagtctgg ctaaaagttt   117480
ttcagtttta ccaatgttt catagaacca gcttggtctt gattttgttg ttgtttatgc   117540
atgttcttag ttattcgttt ctactcttta tcctttccat ttttcttgtg tttagggtag   117600
aagcatatat aattaattga gacctttctt ttctaatcaa agctttaat gctgtaaatt   117660
```

```
ttctaagcac tgtcttcatt gcatcccaca cattttgata tgctgtgttt tcagtactag 117720
agatttttaa ttttatgata ccttatttaa tcatgatgcc ttatttaatc tatagcttat 117780
taaatgtcaa attctaaaca tttgggtttt tctccagata tgtttgttac tgacttctat 117840
tttaatctca tttttgtcag acagcattca ttgtatgact taatcctcct aaatgtattc 117900
agacttgttt tatgttctag attaatgttc tgtgtatact tgaaaagaat gcaagttctt 117960
gggtagactg tttcagaaat gtcagtcaaa tttaagtctt gtttattctt attgattctg 118020
agacaaaggt gtttataatg ttagatttgt ctgctatatc tctgacattg ccaaatatcc 118080
ccttggaggc aaaatctccc cctcccttt gagaaccact gatctatgta gccttttttc 118140
tgggactaat ttagccttgc ttctgagatg tggccctag gtctctactg aatgcccggc 118200
atatttaatt agatctttct ttcctctatg gcctcaaggg atttcaccct aagtatgcac 118260
aaattttat tcagccgaag actgtacaga tttctggagg cctttctttg tgtacctcct 118320
tcgtttccag tagtctgacc cataaattgt acagatttct ggaggccttt ctttgtgtac 118380
ctccttcgtt tccagtagtc tgacccataa attgtacaga tttctggagg cctttctttg 118440
tgtacctcct tcgtttccag tagtctgacc cataaattaa agctgcttta gcctccccaa 118500
acttcaatct ctttctcctc aacccagcaa gattgctaga ccctgggttc cctttcccctt 118560
cactgcagta tgataattac tttcaagcac aaaggtttag aattaagatt tcttactcct 118620
gggctaggta tggcttaccg tatttgtttc tcttttccta gggatcataa tcatgtattg 118680
cttgttgtcc agttttccag taggagggga attccaggct gtacttactt cctgcagcca 118740
aaagaggaag taatgttagt gatttcaata ttaaaacatt aaaaaaaaat ttaagatgga 118800
tgaaattctt ttatatgcat attgaattgg gcttcaccat agttattttt agaattagga 118860
ctaaccggca gggaaaaaaa ctatacggca gggaaaaaaa ctataagcca tcgctgtttt 118920
acaatttgc ataattaga ttttctgtag tatagtaatg tgtaaaatta acccattgtt 118980
aatatagaat gccgttatca ctcctgatta agcggtcttc attttcatgt taatactgat 119040
gtcttgtaat gctttatgga atcaaacatt ttcatacata ttcattagtc taattctaat 119100
cataatccaa tgaaaagag caggaaagat gctcaaggag gttatattca agtccacatg 119160
gcaagtaaga aataagacta ctcggctggg catggtgact tactgcctga atcccagca 119220
ctttgggagg ccaaggtgag cggaattgct tgaacctggg aggcggaagt ggcagtgagc 119280
tgagatcatg ccaatgcact ccagcctagg caacacagca agactctgtc tcgggaaaaa 119340
aataataata ataagacttc tagaagctcc taaatccata gcttttcctc tataccagca 119400
tcttctaaaa atgtcagcag cagtgaagtt tcagtttggg aaataatgca tttcccctct 119460
ctggagagtg cacagttata tctccaagaa gtactgaaat tcagaagtct gcctaatatg 119520
tattaaacat ttagcttttc tcaaactttg accaccaaat cctttgtctc gctctaacta 119580
tagttaacac agaatcagtg ttcccaggag cacactgtga aaaatgtagc actctacaaa 119640
agtcctaatc tccacaggat taagtgaaac catgattaac cctctgttcc ttgtcccttat 119700
tagtaccatt ttctgaagag taatgtatcc ccccaaaact tttatactag tttcactaac 119760
cagaatccat gtacataagg aaggacagat atttgctccc tactaagaca tatctattag 119820
ctacattaaa aaaagtattg catgccgatt ttaaagttat aattaactgg tgatatcaca 119880
gatattccaa gatataattg ctggaataaa cactgttgtt gaagccttct atctatctca 119940
gtactagaat taaactcaag tgcagaatgg cagacaaagt taactaaaaa tcactgtatt 120000
```

-continued

```
atttcatttg gtcctccaaa tagctttgtg agctaaggag gagaaggtgt atcatcacca    120060
cttccatttt atagatgaga aatcaagtga tttactcaag gttaagtcct ccaattcttt    120120
gttatcctgc attttctctt ggctgtagtt taattaataa tcctaagaaa atgcttatat    120180
tttagagtgc agtaagagta cataaacaat gttaaatgcc catcttgcat gtataaaaag    120240
ttatagcaag aaatctggct gggaatggtg gctcacacct gtaatcctgg cactttggga    120300
ggccgaggca ggaggattgc ttgagcccag gagtttaaga ccagcctggg caacataggg    120360
agatcctgtc tctacaaaaa aatttagcca gacacagtgg cttgtgtcct agctactcag    120420
gaggctgagg tgggaggatc acttgagcca aggaggtcaa ggctccagtg agctatgatt    120480
atgccactca gacatggtgg cttgtgccta cagtcctagc tactcaggag gctgaggtgg    120540
gaggatcact tgagccaagg aggtcaaggc tccagtgagc tatgattatg ccactgcact    120600
ccagcctgga tgacacagtg agaccctatc tatctcaaaa aaaaaaaaa aagaaaagaa    120660 aagaaaaga aaatccttta actgacttca tcttaacctt ttagttccta aggacggtct    120720
gaagagccaa gagctatttg atgaaattag aatgacctac atcaaagagc taggaaaagc    120780
cattgtcaag agggaaggaa actccagcca gaactggcag cggttttatc aactgacaaa    120840
actcttggat tctatgcatg aagtaagtgt caaacataaa gccaaatata agagttttct    120900
gggacaaagt atgttttgat tagtgaatat aattatatac cagcagcgcc cccaccccg    120960 cccccagttt gtggatgttg gtgatagctt gagttcaact tatgaacttc agttttgtag    121020 acattttcc taaggccaat tatgaaatat cctttcacct agtcatgtgt atataaaatc    121080
accatgttat tacagaattt agtaatactg ttttttaaaa gtatgattaa tccattaaat    121140
tagaataatg cacccttcat atattatggt actacagtga ttcatgaaat aattctatat    121200
aattctacat acaatcaaag aaatataaaa tgtgttttgt acggaagtgc ttatttttca    121260
tctggggaat tccagtgaga ttggtatatt ctaggccaga taattttttc aaaatagagg    121320
acaacaaaca tgagatgttc ccactgacca atttggaagc ctgatcatta ccatatcttc    121380
tcttgcaggt ggttgaaaat ctccttaact attgcttcca acatttttg gataagacca    121440 tgagtattga attccccgag atgttagctg aaatcatcac caatcagata ccaaaatatt    121500
caaatggaaa tatcaaaaaa cttctgtttc atcaaaagtg actgccttaa taagaatggt    121560
tgccttaaag aaagtcgaat taatagcttt tattgtataa actatcagtt tgtcctgtag    121620
aggttttgtt gttttatttt ttattgtttt catctgttgt tttgttttaa atacgcacta    121680
catgtggttt atagagggcc aagacttggc aacagaagca gttgagtcgt catcacttt    121740 cagtgatggg agagtagatg gtgaaattta ttagttaata tatcccagaa attagaaacc    121800
ttaatatgtg gacgtaatct ccacagtcaa agaaggatgg cacctaaacc accagtgccc    121860
aaagtctgtg tgatgaactt tctcttcata cttttttca cagttggctg gatgaaattt    121920
tctagacttt ctgttggtgt atccccccc tgtatagtta ggatagcatt tttgatttat    121980
gcatggaaac ctgaaaaaaa gtttacaagt gtatatcaga aagggaagt tgtgcctttt    122040 atagctatta ctgtctggtt ttaacaattt cctttatatt tagtgaacta cgcttgctca    122100
ttttttctta cataattttt tattcaagtt attgtacagc tgtttaagat gggcagctag    122160
ttcgtagctt tcccaaataa actctaaaca ttaatcaatc atctgtgtga aaatgggttg    122220
gtgcttctaa cctgatggca cttagctatc agaagaccac aaaaattgac tcaaatctcc    122280
agtattcttg tcaaaaaaaa aaaaaaaaaa gctcatatttt tgtatatatc tgcttcagtg    122340
gagaattata taggttgtgc aaattaacag tcctaactgg tatagagcac ctagtccagt    122400
```

-continued

```
gacctgctgg gtaaactgtg gatgatggtt gcaaaagact aatttaaaaa ataactacca    122460
agaggccctg tctgtaccta acgccctatt tttgcaatgg ctatatggca agaaagctgg    122520
taaactattt gtcttccagg accttttgaa gtagtttgta taacttctta aaagttgtga    122580
ttccagataa ccagctgtaa cacagctgag agactttaa tcagacaaag taattcctct     122640
cactaaactt tacccaaaaa ctaaatctct aatatggcaa aaatggctag acacccattt    122700
tcacattccc atctgtcacc aattggttaa tctttcctga tggtacagga agctcagct     122760 actgattttt gtgatttaga actgtatgtc agacatccat gtttgtaaaa ctacacatcc    122820
ctaatgtgtg ccatagagtt taacacaagt cctgtgaatt tcttcactgt tgaaaattat    122880
tttaaacaaa atagaagctg tagtagccct ttctgtgtgc accttaccaa ctttctgtaa    122940
actcaaaact taacatattt actaagccac aagaaatttg atttctattc aaggtggcca    123000
aattatttgt gtaatagaaa actgaaaatc taatattaaa aatatggaac ttctaatata    123060
tttttatatt tagttatagt ttcagatata tatcatattg gtattcacta atctgggaag    123120
ggaagggcta ctgcagcttt acatgcaatt tattaaaatg attgtaaaat agcttgtata    123180
gtgtaaaata agaatgattt ttagatgaga ttgttttatc atgacatgtt atatattttt    123240
tgtaggggtc aaagaaatgc tgatggataa cctatatgat ttatagtttg tacatgcatt    123300
catacaggca gcgatggtct cagaaaccaa acagtttgct ctaggggaag agggagatgg    123360
agactggtcc tgtgtgcagt gaaggttgct gaggctctga cccagtgaga ttacagagga    123420
agttatcctc tgcctcccat tctgaccacc cttctcattc caacagtgag tctgtcagcg    123480
caggtttagt ttactcaatc tccccttgca ctaaagtatg taaagtatgt aaacaggaga    123540
caggaaggtg gtgcttacat ccttaaaggc accatctaat agcgggttac tttcacatac    123600
agccctcccc cagcagttga atgcaacag aagcttcaga agtttggcaa tagtttgcat     123660
agaggtacca gcaatatgta aatagtgcag aatctcatag gttgccaata atacactaat    123720
tcctttctat cctacaacaa gagtttattt ccaaataaaa tgaggacatg ttttgtttt     123780 ctttgaatgc tttttgaatg ttatttgtta ttttcagtat tttggagaaa ttatttaata    123840
aaaaaacaat catttgcttt ttgaatgctc tctaaaaggg aatgtaatat tttaagatgg    123900
tgtgtaaccc ggctggataa attttttggtg cctaagaaaa ctgcttgaat attcttatca    123960
atgacagtgt taagtttcaa aaagagcttc taaaacgtag attatcattc ctttatagaa    124020
tgttatgtgg ttaaaaccag aaagcacatc tcacacatta atctgatttt catcccaaca    124080
atcttggcgc tcaaaaaata gaactcaatg agaaaaagaa gattatgtgc acttcgttgt    124140
caataataag tcaactgatg ctcatcgaca actataggag gcttttcatt aaatgggaaa    124200
agaagctgtg ccctttagg atacgtgggg gaaaagaaag tcatcttaat tatgtttaat     124260
tgtggattta agtgctatat ggtggtgctg tttgaaagca gatttatttc ctatgtatgt    124320
gttatctggc catcccaacc caaactgttg aagtttgtag taacttcagt gagagttggt    124380
tactcacaac aaatcctgaa aagtattttt agtgtttgta ggtattctgt gggatactat    124440
acaagcagaa ctgaggcact taggacataa cactttggg gtatatatat ccaaatgcct     124500
aaaactatgg gaggaaacct tggccacccc aaaaggaaaa ctaacatgat ttgtgtctat    124560
gaagtgctgg ataattagca tgggatgagc tctgggcatg ccatgaagga aagccacgct    124620
cccttcagaa ttcagaggca gggagcaatt ccagtttcac ctaagtctca aattttagt     124680 tcccttttaa aaaccctgaa aactacatca ccatggaatg aaaaatattg ttatacaata    124740
```

```
cattgatctg tcaaacttcc agaaccatgg tagccttcag tgagatttcc atcttggctg  124800
gtcactccct gactgtagct gtaggtgaat gtgtttttgt gtgtgtgtgt ctggtttag   124860
tgtcagaagg gaaataaaag tgtaaggagg acactttaaa ccctttgggt ggagtttcgt  124920
aatttcccag actattttca agcaacctgg tccacccagg attagtgacc aggttttcag  124980
gaaaggattt gcttctctct agaaaatgtc tgaaaggatt ttattttctg atgaaaggct  125040
gtatgaaaat accctcctca aataacttgc ttaactacat atagattcaa gtgtgtcaat  125100
attctatttt gtatattaaa tgctatataa tggggacaaa tctatattat actgtgtatg  125160
gcattattaa gaagcttttt cattatttt tatcacagta attttaaaat gtgtaaaaat  125220
taaaaccagt gactcctgtt taaaaataaa agttgtagtt ttttattcat gctgaataat  125280
aatctgtagt taaaaaaaaa gtgtctttt acctacgcag tgaaatgtca gactgtaaaa  125340
ccttgtgtgg aaatgtttaa ctttatttt ttcatttaaa tttgctgttc tggtattacc  125400
aaaccacaca tttgtaccga attggcagta aatgttagcc atttacagca atgccaaata  125460
tggagaaaca tcataataaa aaaatctgct ttttcattat gtgactccaa catgcttttg  125520
tagaacttgt acagttccga ttgtccaatc tgatttttgt ttactgaaag tagagttacc  125580
cctgcttcag gaac                                                   125594
```

METHODS FOR DIAGNOSING GLAUCOMA AND DISCOVERING ANTI-GLAUCOMA DRUGS

This application is a continuation-in-part of U.S. application Ser. No. 09/308,295, filed May 17, 1999, now abandoned, which is a 371 application of PCT/US97/21054, filed Nov. 14, 1997. Priority is claimed from the provisional application, U.S. patent application Ser. No. 60/033,227 filed Dec. 5, 1996.

BACKGROUND OF THE INVENTION

1. Field of the Invention

The present invention relates to the field of glaucoma diagnosis and treatment. More specifically, the present invention provides methods for diagnosis of glaucoma by measuring the amount of GRβ present in the trabecular meshwork of a patient's eye.

2. Description of the Related Art

Glaucoma is usually diagnosed by monitoring a patient's visual field loss, changes in the appearance of their optic disc, and their intraocular pressure. Glaucoma is currently treated using one or more of three strategies to lower the elevated intraocular pressure associated with the disease: with pharmaceuticals (such as beta-blockers, carbonic anhydrase inhibitors, miotics or prostaglandins), with laser trabeculoplasty, and/or with glaucoma filtration surgery. All of these therapies indirectly lower intraocular pressure but do not address the underlying disease process occurring in the trabecular meshwork. It would be advantageous to be able to diagnose glaucoma before a patient begins experiencing a loss in their visual field and deterioration of their optic disc.

There is a large body of evidence suggesting that glucocorticoids are involved in the generation of ocular hypertension and glaucoma (Clark 1995). The human glucocorticoid receptor (hGR) and its isoforms, hGRα (SEQ ID NO:3) and hGRβ (SEQ ID NO:1), are described in Encio and Detera-Wadleigh (1991) (See also FIG. 1). Several investigators have shown that the human trabecular meshwork (TM) contains the classical glucocorticoid receptor (hGRα) (Weinreb et al. 1981; Hernandez et al. 1983). Recently, the expression of an alternatively spliced form of the human glucocorticoid receptor (hGRβ) was discovered in non-ocular tissues and cells (Bamberger et al. 1995; Oakley et al. 1996). This alternatively spliced form of hGR is expressed as a protein (SEQ ID NO:2) which no longer binds glucocorticoids, but is able to interfere with the activated form of the normal glucocorticoid receptor and block or alter physiological functions of the glucocorticoid receptor.

SUMMARY OF THE INVENTION

The present invention is directed to methods for diagnosing glaucoma by testing a person for aberrant hGRβ expression. In preferred embodiments, a decrease in hGRβ expression in the trabecular meshwork of glaucomatous eyes as compared to hGRβ expression in non-glaucomatous eyes. Also set forth are methods for screening for therapeutic agents useful for treating glaucoma.

BRIEF DESCRIPTION OF THE DRAWINGS

The following drawing forms part of the present specification and is included to further demonstrate certain aspects of the present invention. The invention may be better understood by reference to this drawing in combination with the detailed description of specific embodiments presented herein.

DESCRIPTION OF PREFERRED EMBODIMENTS

Figure 1:
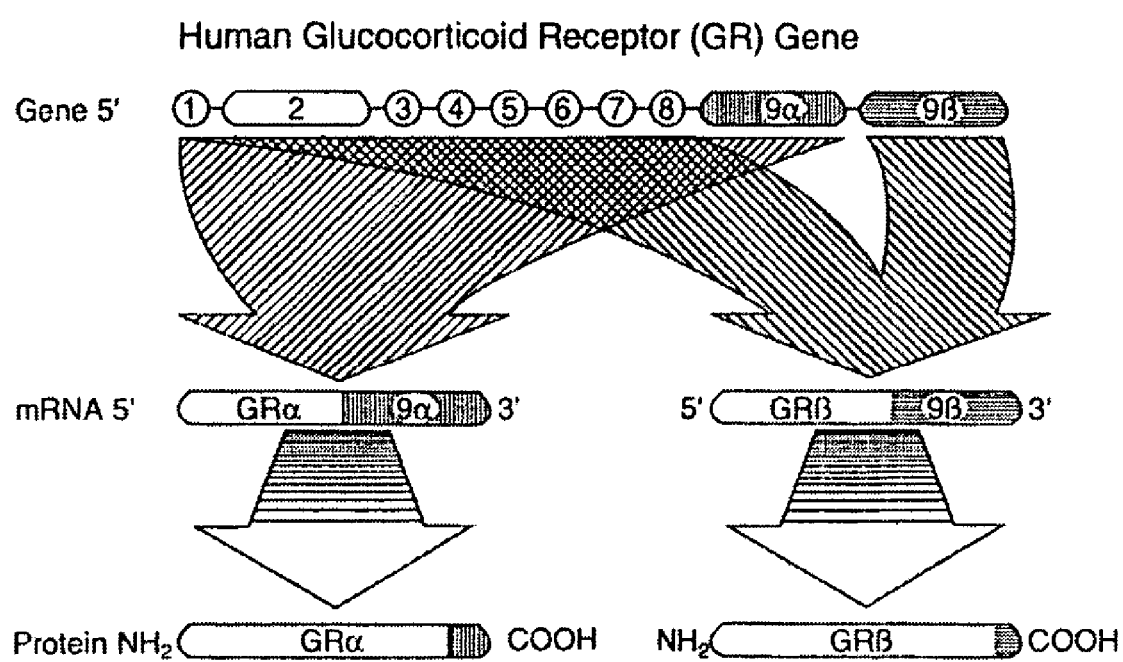
FIG. 1. Illustrates the alternative splice forms of the human glucocorticoid receptor (hGR) gene.
Figure 2:
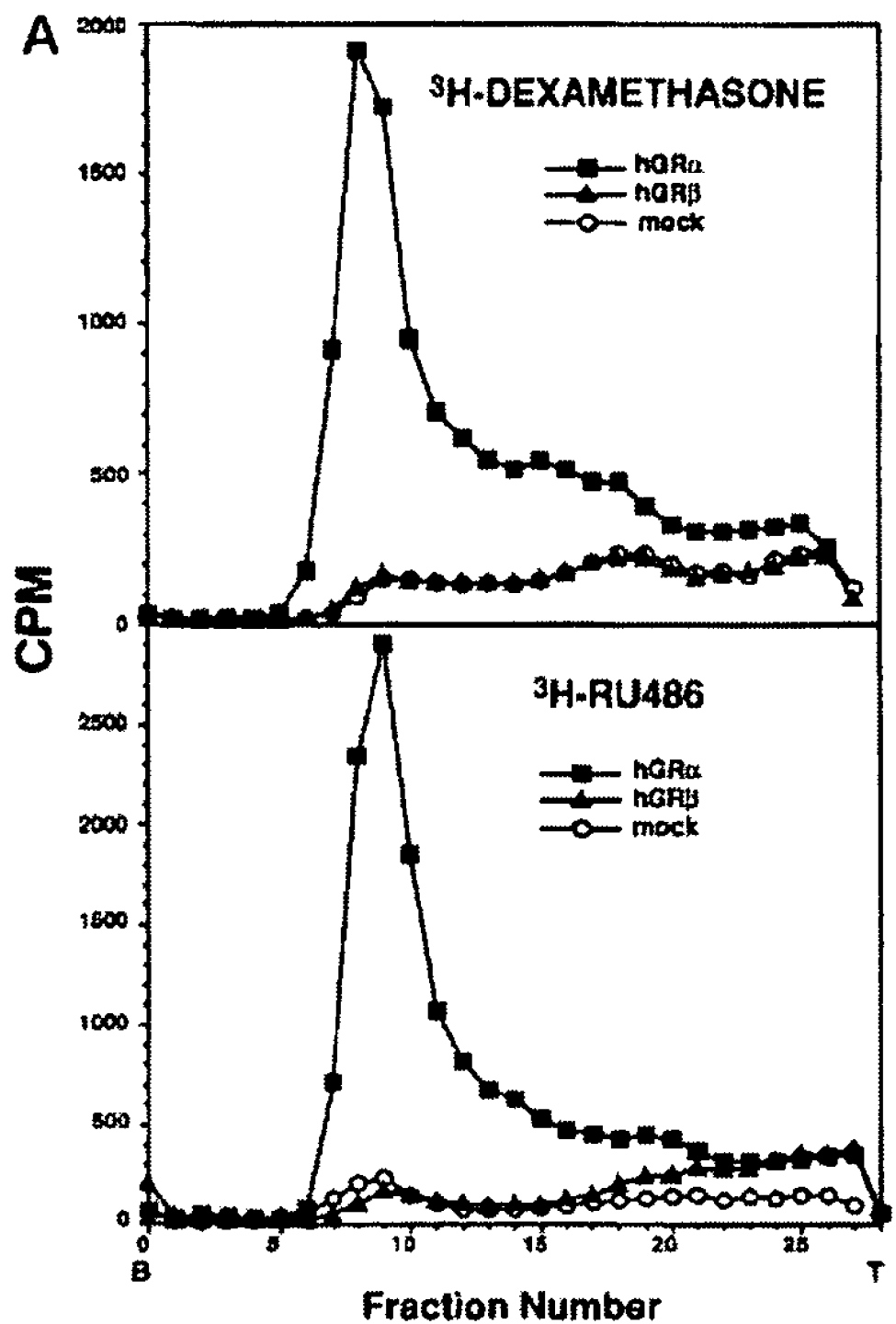
FIG. 2. Illustrates binding of glucocorticoids to GRα and failure of glucocorticoids to bind to GRβ.

Surprisingly, it has been found that cultured human trabecular meshwork cell lines express the proteins from both an alternate splice form of the human glucocorticoid receptor (GRβ; SEQ ID NO:1), as well as the normal glucocorticoid receptor (GRα; SEQ ID NO:3). Glaucomatous TM cells have less GRβ protein and therefore are more susceptible to endogenous and exogenous glucocorticoids. It is believed that the elevated intraocular pressure associated with primary open-angle glaucoma may be due to the aberrant expression of GRβ in the trabecular meshwork. Therefore, determining that an individual abnormally expresses GRβ in their trabecular meshwork or other tissues can lead to a diagnosis of glaucoma.

The present invention further provides a method for determining whether a candidate substance has therapeutic value in treating glaucoma by determining whether the candidate substance interacts with the GRβ protein (SEQ ID NO:2) or alters the expression of GRβ (SEQ ID NO:1). This can be done using ligand binding assays or GRβ functional assays.

Diagnosing aberrant GRβ expression or defects in the GR gene which encodes GRβ can be done by using procedures well known to those skilled in the art (Caskey 1993). For example, subjects could be screened for the presence of a genetic defect in GRβ by analyzing the DNA derived from peripheral blood leukocytes. Types of DNA analyses could include, but would not be limited to: restriction fragment length polymorphisms (RFLP), single-stranded conformation polymorphisms (SSCP), polymerase chain reaction (PCR), denaturing gradient gel electrophoresis, allele specific oligonucleotide ligation assay, and allele specific hybridization assay. In addition, trabecular meshwork, or other relevant cells from subjects could be analyzed for GRβ expression by a number of techniques such as reverse-transcription polymerase chain reaction (RT-PCR), immunoassays, GR functional assays, etc.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Effect of GRβ Transfection on DEX-Induced Myocilin Expression in TM Cells

GRα and GRβ expression vectors and specific antibodies were generated. The expression and localization of GRα and GRβ in normal and glaucomatous TM cell lines was examined in cells containing dexamethasone (DEX) and in cells lacking DEX.

It was found that GRβ is expressed at higher levels in normal (non-glaucomatous) TM cells. It exists in both the cytoplasm and in nucleus (IF) and is more concentrated in the nucleus. In glaucomatous TM cells, the amount of GRβ is relatively lower than in normal TM cells. It was also noted that GRβ is evenly distributed in the cytoplasm and nucleus of glaucomatous TM cells.

Treatment with DEX caused GRα nuclear translocation into the nucleus. DEX time-dependently down-regulated GRα in both normal and glaucomatous TM cells. Western blotting detected GRβ doublets present in both cytoplasm and nuclear region. Three day DEX treatment increased nuclear short form of GRβ in normal TM cell lines, but not in glaucomatous TM cell lines. Both GRα and GRβ co-precipitate with Hsp90. It was also found that GRβ blocks DEX induction of MYOC.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Publications

Bamberger, C M, Bamberger, A-M, de Castro, M, Chrousos, GP, "*Glucocorticoid Receptor β, a Potential Endogenous Inhibitor of Glucocorticoid Action in Humans*" J. CLIN. INVEST. 95:2435-2441 (1995).

Caskey, C T, "*Molecular Medicine. A Spin-off from the Helix*" JAMA 269(15):1986-1992 (1993).

Clark, A F, "*Steroids, Ocular Hypertension and Glaucoma*" J. GLAUCOMA 4:354-369 (1995).

Encio, I J and Detera-Wadleigh, S D, "*The Genomic Structure of the Human Glucocorticoid Receptor*" J. BIOL. CHEM. 266(11):7182-7188 (1991).

Hernandez, M R, Wenk, E J, Weinstein, B I, Abumohor, P, Podos, S M, Dunn, M W, Southren, A L, "*Glucocorticoid Target Cells in Human Outflow Pathway: Autopsy and Surgical Specimens*" INVEST. OPHTHALMOL. VIS. SCI. 24:1612-1616 (1983).

Oakley, R H, Sar, M, Cidlowski, J A, "*The Human Glucocorticoid Receptor β Isoform*" J. BIOL. CHEM. 271(16): 9550-9559 (1996).

Weinreb, R N, Bloom, E, Baxter, J D, Avarado, J, Lan, N, O'Donnell, J, Polansky, J R, "*Detection of Glucocorticoid Receptors in Cultured Human Trabecular Cells*" INVEST. OPHTHALMOL. VIS. SCI. 21(3):403-407 (1981).

We claim:

1. A method for diagnosing glaucoma in a patient, said method comprising the steps:
   (a) obtaining a biological sample from the trabecular meshwork of said patient; and
   (b) analyzing said sample for expression of GRβ (SEQ ID NO:1);
   wherein a decrease in expression of GRβ as compared to expression of GRβ in a patient not suffering from glaucoma indicates a diagnosis of glaucoma.

* * * * *